United States Patent
Chen et al.

(10) Patent No.: US 10,328,182 B2
(45) Date of Patent: Jun. 25, 2019

(54) COMPOSITIONS AND METHODS FOR REDUCING NEOINTIMA FORMATION

(71) Applicant: University of Georgia Research Foundation, Inc., Athens, GA (US)

(72) Inventors: Shiyou Chen, Bogart, GA (US); Rui Tang, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 284 days.

(21) Appl. No.: 14/942,139

(22) Filed: Nov. 16, 2015

(65) Prior Publication Data

US 2016/0058923 A1    Mar. 3, 2016

Related U.S. Application Data

(63) Continuation-in-part of application No. PCT/US2014/037955, filed on May 14, 2014.
(Continued)

(51) Int. Cl.
*A61K 48/00* (2006.01)
*C07H 21/02* (2006.01)
(Continued)

(52) U.S. Cl.
CPC .............. *A61L 31/16* (2013.01); *A61K 31/00* (2013.01); *A61K 31/198* (2013.01); *A61K 31/42* (2013.01);
(Continued)

(58) Field of Classification Search
CPC .. C12N 15/1137; A61K 31/00; A61K 31/513; A61K 31/7072; A61L 31/16;
(Continued)

(56) References Cited

U.S. PATENT DOCUMENTS 3,856,807 A    12/1974    Hanka
3,878,047 A    4/1975    Hanka
(Continued)

FOREIGN PATENT DOCUMENTS

WO    9831375    7/1998
WO    9851812    11/1998
(Continued)

OTHER PUBLICATIONS

Rui Tang (FASEB Journal, Apr. 1, 2013 vol. 27, p. 1 of 1), downloaded from http://www.fasebj.org/doi/abs/10.1096/fasebj.27.1_supplement.1035.4?legid=faseb%3B2 on Mar. 13, 2018.*
(Continued)

*Primary Examiner* — Terra C Gibbs
(74) *Attorney, Agent, or Firm* — Pabst Patent Group LLP

(57) ABSTRACT

Compositions, devices, grafts and methods for reducing or preventing anti-neointima following cardiovascular injuries and interventions are disclosed. The compositions, devices, and grafts typically include an effective amount of a CTP synthase 1 inhibitor to reduce proliferation of vascular smooth muscle cells, without substantial reducing the proliferation of endothelial cells. Methods of reducing neointima formation, accelerating re-endothelialization, and reducing restenosis in a subject using the compositions, devices, and grafts are also disclosed.

20 Claims, 16 Drawing Sheets
Specification includes a Sequence Listing.

Related U.S. Application Data

(60) Provisional application No. 61/823,163, filed on May 14, 2013.

(51) Int. Cl.

| | | |
|---|---|---|
| *C07H 21/04* | (2006.01) | |
| *A61L 31/16* | (2006.01) | |
| *A61L 27/54* | (2006.01) | |
| *A61K 45/06* | (2006.01) | |
| *A61K 31/00* | (2006.01) | |
| *A61K 31/198* | (2006.01) | |
| *A61K 31/42* | (2006.01) | |
| *A61K 31/7068* | (2006.01) | |
| *A61K 31/7072* | (2006.01) | |
| *C12N 15/113* | (2010.01) | |
| *A61L 27/50* | (2006.01) | |
| *A61K 35/74* | (2015.01) | |
| *A61K 31/4412* | (2006.01) | |
| *A61L 31/08* | (2006.01) | |

(52) U.S. Cl.
CPC ...... *A61K 31/4412* (2013.01); *A61K 31/7068* (2013.01); *A61K 31/7072* (2013.01); *A61K 35/74* (2013.01); *A61K 45/06* (2013.01); *A61L 27/507* (2013.01); *A61L 27/54* (2013.01); *A61L 31/08* (2013.01); *C12N 15/1137* (2013.01); *C12Y 603/04002* (2013.01); *A61L 2300/416* (2013.01); *A61L 2300/434* (2013.01); *C12N 2310/11* (2013.01); *C12N 2310/12* (2013.01); *C12N 2310/14* (2013.01); *C12N 2310/141* (2013.01); *C12N 2310/16* (2013.01); *C12N 2310/531* (2013.01)

(58) Field of Classification Search
CPC .... A61L 2300/416; A61L 27/54; A61L 31/08; C12Y 603/04002; A61P 43/00
See application file for complete search history.

(56) References Cited

U.S. PATENT DOCUMENTS

| | | | |
|---|---|---|---|
| 5,059,211 A | 10/1991 | Stack | |
| 5,087,639 A | 2/1992 | McGovren | |
| 5,306,286 A | 4/1994 | Stack et al. | |
| 5,356,802 A | 10/1994 | Chandrasegaran | |
| 5,436,150 A | 7/1995 | Chandrasegaran | |
| 5,487,994 A | 1/1996 | Chandrasegaran | |
| 5,891,108 A | 4/1999 | Leone | |
| 5,935,506 A | 8/1999 | Schmitz | |
| 6,045,568 A | 4/2000 | Igaki | |
| 6,140,081 A | 10/2000 | Barbas | |
| 6,453,242 B1 | 9/2002 | Eisenberg | |
| 6,534,261 B1 | 3/2003 | Cox, III | |
| 6,610,512 B1 | 8/2003 | Barbas | |
| 6,746,838 B1 | 6/2004 | Choo | |
| 6,866,997 B1 | 3/2005 | Choo | |
| 6,918,929 B2 | 7/2005 | Udipi | |
| 6,923,828 B1 | 8/2005 | Wiktor | |
| 6,945,992 B2 | 9/2005 | Goodson, IV | |
| 6,986,785 B2 | 1/2006 | OShaughnessy | |
| 7,060,090 B2 | 6/2006 | Thornton | |
| 7,067,617 B2 | 6/2006 | Barbas, III | |
| 7,144,419 B2 | 12/2006 | Cheng | |
| 7,163,555 B2 | 1/2007 | Dinh | |
| 7,323,008 B2 | 1/2008 | Kantor | |
| 7,534,448 B2 | 5/2009 | Saltzman | |
| 7,618,448 B2 | 11/2009 | Schmitz | |
| 7,651,527 B2 | 1/2010 | Krivoruchko | |
| 7,665,034 B2 | 2/2010 | Mitchell | |
| 7,678,141 B2 | 3/2010 | Greenan | |
| 7,744,645 B2 | 6/2010 | Thornton | |
| 7,942,917 B2 | 5/2011 | Nowak, Jr. | |
| 8,001,925 B2 | 8/2011 | Kantor | |
| 8,034,099 B2 | 10/2011 | Pellegrini | |
| 8,048,149 B2 | 11/2011 | Yang | |
| 8,066,760 B2 | 11/2011 | Mitchell | |
| 8,100,960 B2 | 1/2012 | Bruszewski | |
| 8,157,855 B2 | 4/2012 | Eidenschink | |
| 8,182,524 B2 | 5/2012 | Spiridigliozzi | |
| 8,187,284 B2 | 5/2012 | Jordan | |
| 8,187,322 B2 | 5/2012 | Smith | |
| 8,172,893 B2 | 6/2012 | Moore | |
| 8,197,528 B2 | 6/2012 | Colgan | |
| 8,206,432 B2 | 6/2012 | Kveen | |
| 8,221,490 B2 | 7/2012 | Keeen | |
| 8,231,669 B2 | 7/2012 | Miller | |
| 8,236,044 B2 | 8/2012 | Robaina | |
| 8,242,120 B2 | 8/2012 | Chu | |
| 8,252,048 B2 | 8/2012 | Smith | |
| 8,252,065 B2 | 8/2012 | Ward | |
| 8,257,431 B2 | 9/2012 | Henderson | |
| 8,267,425 B2 | 9/2012 | Davidson | |
| 8,292,945 B2 | 10/2012 | Welsh | |
| 8,298,278 B2 | 10/2012 | Gregorich | |
| 8,298,280 B2 | 10/2012 | Yadin | |
| 8,348,991 B2 | 1/2013 | Weber | |
| 8,348,992 B2 | 1/2013 | Brown | |
| 8,348,993 B2 | 1/2013 | Tischler | |
| 8,353,952 B2 | 1/2013 | Thompson | |
| 8,359,998 B2 | 1/2013 | Shekalim | |
| 8,361,140 B2 | 1/2013 | Meyer | |
| 8,372,134 B2 | 2/2013 | Schlick | |
| 8,372,138 B2 | 2/2013 | Jordan | |
| 8,377,112 B2 | 2/2013 | Griffin | |
| 8,388,676 B2 | 3/2013 | Stinson | |
| 8,398,695 B2 | 3/2013 | Chalekian | |
| 8,414,637 B2 | 4/2013 | Chouinard | |
| 8,414,639 B2 | 4/2013 | Tischler | |
| 8,414,656 B2 | 4/2013 | Davoudi | |
| 2002/0165356 A1 | 11/2002 | Barbas | |
| 2002/0168320 A1 | 11/2002 | Lanza | |
| 2003/0086867 A1 | 5/2003 | Lanza | |
| 2003/0129136 A1 | 7/2003 | Lanza | |
| 2004/0058951 A1 | 3/2004 | Lanza | |
| 2004/0115192 A1 | 6/2004 | Lanza | |
| 2004/0197892 A1 | 10/2004 | Moore | |
| 2006/0002971 A1 | 1/2006 | Saltzman | |
| 2006/0147380 A1 | 7/2006 | Lanza | |
| 2006/0239919 A1 | 10/2006 | Wickline | |
| 2007/0140965 A1 | 6/2007 | Lanza | |
| 2007/0154989 A1 | 7/2007 | Barbas | |
| 2007/0202040 A1 | 8/2007 | Lanza | |
| 2007/0213269 A1 | 9/2007 | Barbas | |
| 2007/0258908 A1 | 11/2007 | Lanza | |
| 2008/0175792 A1 | 7/2008 | Lanza | |
| 2008/0247943 A1 | 10/2008 | Lanza | |
| 2009/0105186 A1 | 4/2009 | Matthes | |
| 2009/0270431 A1 | 10/2009 | Chu | |
| 2009/0324682 A1 | 12/2009 | Popowski | |
| 2010/0151436 A1 | 6/2010 | Fong | |
| 2011/0145940 A1 | 6/2011 | Voytas | |
| 2013/0064765 A1 | 3/2013 | Myerson | |

FOREIGN PATENT DOCUMENTS

| | | | |
|---|---|---|---|
| WO | 9853059 | 11/1998 | |
| WO | 9935236 | 7/1999 | |
| WO | 0056376 | 9/2000 | |
| WO | 0180809 | 11/2001 | |
| WO | 02443210 | 6/2002 | |
| WO | 2003016496 | 2/2003 | |
| WO | WO-03024455 A2 * | 3/2003 | ........... A61K 9/0024 |
| WO | 03059408 | 7/2003 | |
| WO | 2004084796 | 10/2004 | |
| WO | 2011070152 | 6/2011 | |
| WO | 2011072246 | 6/2011 | |

(56) References Cited

FOREIGN PATENT DOCUMENTS

| WO | 2013176772 | 11/2013 |
|---|---|---|
| WO | 2014018423 | 1/2014 |

OTHER PUBLICATIONS

Tang et al. (Arterioscler Thromb Vasc Biol, 2013, vol. 33:2336-2344).*
McDowell et al. (Vascular Cell, 2011 vol. 3, pp. 1-5).*
Agrawal, et al., "Cell-cycle kinetics and VSV-G pseudotyped retrovirus-mediated gene transfer in blood-derived CD34+ cells", Exper. Hematol., 24:738-747 (1996).
Ahluwalia, et al, "Metabolism and action of amino acid analog anti-cancer agents", Pharmac. Ther., 42(16):243-271 (1990).
Anderson, et al., "Potential signalling roles for UTP and UDP: sources, regulation and release of euracil nucleotides", Trends Pharmacol. Sci., 18:387-392 (1997).
Anderson, et al., "Restenosis after coronary angioplasty", J Interv. Cardiol., 6:187-202 (1993).
Arita, et al., "Adipocyte-derived plasma protein adiponectin acts as a platelet-derived growth factor-BB-binding protein and regulates growth factor-induced common postreceptor signal in vascular smooth muscle cell", Circulation., 105:2893-8 (2002).
Bauters and Isner, "The biology of restenosis", Prog Cardiovasc Dis 40:107-16 (1997).
Bearne, et al., "Inhibition of *Escherichia coli* CTP synthase by glutamate gamma-semialdehyde and the role of the allosteric effector GTP in glutamine hydrolysis", Biochem, J., 356:223-32 (2001).
Bennett and O'Sullivan, "Mechanisms of angioplasty and stent restenosis: implications for design of rational therapy", Pharmacol Ther, 91:149-66 (2001).
Berg, et al., "Evidence for transformation-related increase in CTP synthetase activity in situ in human lymphoblastic leukemia", Eur. J. Biochem., 216:161-7 (1993).
Brockman, et al., "{The mechanism of action of 3-deazauridine in tumor cells sensitive and resistant to arabinosylcytosine", Ann. N Y. Acad. Sci., 225:501-521 (1975).
Carcamo, et al., "Induction of cytoplasmic rods and rings structures by inhibftion of the CTP and GTP synthetic pathway in mammalian cells", PLoS ONE, 6(12): e29690, doi:10.1371/journal.pone.0029690 (2011).
Cermak, et al, "Efficient design and assembly of custom TALEN and other TAL effector-based constructs for DNA targeting", Nucl. Acids Res., 39(12): e82 1-11 (2011).
Clowes, et al., "Significance of quiescent smooth muscle migration in the injured rat carotid artery", Circ. Res., 56:139-45 (1986).
Cong, et al., "Multiplex genome engineering using CRISPR/Cas systems", Science, 15:339(6121):819-23 (2013).
Conti, et al, "Synthesis and in vitro/in vivo evaluation of the antitrypanosomal activity of 3-bromoacivicin, a potent CTP synthetase inhibitor", ChemMedChem, 6(2): 329-33 (2011).
Conti, et al., "Synthesis and biological evaluation of new amino acids structurally related to the antitumor agent acivicin", Farmaco, 58(9):683-90 (2003).
Cotran, et al., "Cytokine-endothelial interactions in inflammation, immunity, and vascular injury", J Am Soc Nephrol., 1:225-235 (1990).
Cyrus, et al., "Intramural delivery of rapamycin with alphavbeta3-targeted paramagnetic nanoparticles inhibits stenosis after balloon injury", Arterioscler Throat Vasc Biol, 28:820-6 (2008).
Dawson, et al., "CD36 mediates the In vitro inhibitory effects of thrombospondin-1 on endothelial cells", J Cell Biol., 138:707-717 (1997).
De Clercq, et al., "Broad-spectrum antiviral and cytocidal activity of cyclopentenylcytosine, a carbocyclic nucleoside targeted at CTP synthetase", Biochem. Pharmacol., 41:1821-9 (1991).
Derossi, et al., "The third helix of the Antennapedia homeodomain translocates through biological membranes", J Biol Chem. 269(14):10444-50 (1994).

Dhanabal, et al., "Endostatin induces endothelial cell apoptosis", J. Biol. Chem., 274:11721-11726 (1999).
Dollery, et al., "In vivo adenoviral gene transfer of TIMP-1 after vascular injury reduces neointimal formation", Ann. N. Y. Acad. Sci., 878:742-743 (1999).
Elbashir, et al., "Duplexes of 21-nucleotide RNAs mediate RNA interference in cultured mammalian cells", Nature, 411:494-8 (2001).
Elezi, et al., "Vessel size and long-term outcome after coronary stent placement", Circulation, 98:1875-80 (1998).
Epstein, et al., "Cytotoxic effects of a recembinantchimeric toxin on rapidly proliferating vascular smooth muscle cells", Circulation, 84:778-87 (1991).
Farb, et al., "Morphological predictors of restenosis after coronary stenting in humans", Circulation, 105:2974-80 (2002).
Fingerle, et al., "Role of platelets in smooth muscle cell proliferation and migration after vascular injury in rat carotid artery", PNAS, 86:8412-6 (1989).
Finn, et al., "Pathological correlates of late drug-eluting stent thrombosis: strut coverage as a marker of endothelialization", Circulation., 115:2435-41 (2007).
Fischman, et al., "A randomized comparison of coronary-stent placement and balloon angioplasty in the treatment of coronary artery disease. Stent Restenosis Study Investigators", N Engl J Med, 331:496-501 (1994).
Frankel and Pabo, "Cellular uptake of the tat protein from human immunodeficiency virus", Cell, 55(6):1189-93 (1988).
Gao, et al., "Potentiation of the anti-HIV activity of zalcitabine and lamivudine by a CTP synthase inhibitor, 3-deazauridine", Nucleosides, Nucleotides Nucleic Acids, 19:371-7 (2000).
Georges-Courbot, et al., "Poly(I)-poly(C12U) but not ribavirin prevents death in a hamster model of Nipah virus infection", Agents Chemother., 50:1768-72 (2006).
Goldschmidt-Cleront and Moldovan, "Stress, superoxide, and signal transduction", Gene Expr 7:255-60 (1999).
Goodman, et al., "Recombinant adeno-associated virus-mediated gene transfer into hematopoietic progenitor cells", Blood 84:1492-1500 (1994).
Hagensen, et al., "Circulating endothelial progenitor cells do not contribute to regeneration of endothelium after murine arterial injury", Cardiovasc Res., 93:223-31 (2012).
Heckenkamp, et al., "Vascular restenosis. Basic science and clinical implications", J Cardiovasc. Surg. (Torino), 43:349-357 (2002).
Hidalgo, et al., "A Phase I and pharmacological study of the glutamine antagonist acivicin with the amino acid solution aminosyn in patients with advanced solid malignancies", Clin Cancer Res., 4(11):2763-70 (199B).
Hillaireau, et al., "Polymer-based nanoparticles for the delivery of nucleoside analogues", J. Nanosci. Nanotechnol., 6(9-10):2608-17 (2006).
Hofer, et al., "Trypanosoma brucei CTP synthetase: a target for the treatment of African sleeping sickness", PNAS, 98(11):6412-6 (2001).
Hofma, et al., "Indication of long-term endothelial dysfunction after sirolimus-eluting stent implantation", Eur. Heart J, 27:166-170 (2006).
Indolfi, et al., "Molecular mechanisms of in-stent restenosis and approach to therapy with eluting stents", Trends Cardiovasc Med., 13:142-8 (2003).
Inoue, et al., "Vascular inflammation and repair implications for re-endothelialization, restenosis, and stent thrombosis", JACC: Cardiovasc Interv., 4(10):1057-66 (2011).
Iyengar, et al., "Aspartate-107 and leucine-109 facilitate efficient coupling of glutamine hydrolysis to CTP synthesis by *Escherichia coli* CTP synthase", Biochem. J., 369:497-507 (2005).
Jinek, et al., "A programmable dual-RNA-guided DNA endonuclease in adaptive bacterial immunity", Science, 337(6096):816-21 (2012).
Jovinge, et al., "Tumor necrosis factor-alpha activates smooth muscle cell migration in culture and is expressed in the balloon-injured rat aorta", Arterloscler. Thromb. Vass. Biol., 17:490-7 (1997).
Julander, et al., "Treatment of Venezuelan equine encephalitis virus infection with (-)-carbodine", Antiviral Res., 80(3):309-15 (2008).

(56) References Cited

OTHER PUBLICATIONS

Kabouridis, "Biological applications of protein transduction technology",Trends Biotechnol, (11):498-503 (2003).
Kim, et al., "Chimeric restriction endonuclease", PNAS, 91:883-7 (1994a).
Kim, et al., "The long isoform of the rat thyrotropin-releasing hormone receptor down-regulates Gq proteins", J. Biol. Chem. 269(31):19933-40 (1994b).
Kinlay, et al., "Endothelial function and coronary artery disease", Curr. Opin. Lipidol., 12:383-9 (2001).
Laaksovirta, et al., "Encrustation and strength retention properties of the self-expandable, biodegradable, self-reinforced L-lactide-glycolic acid co-polymer 80:20 spiral urethral stent in vitro", J Urol., 170(2 Pt 1):466-71 (2003).
Lalut, et al., "Synthesis of C3-arylated-3-deazauridine derivatives with potent anti-HSV-1 activities", Bioorg. Med. Chem. Lett., 22(24):7461-4 (2012).
Lanza, et al., "In vivo molecular imaging of stretch-induced tissue factor in carotid arteries with ligand-targeted nanoparticles", J. Am. Soc. Echo., 13:608-14 (2000).
Lanza, et al., "Targeted antiproliferative drug delivery to vascular smooth muscle cells with a magnetic resonance imaging nanoparticle contrast agent: implications for rational therapy of restenosis", Circulation, 106:2842-7 (2002).
Legraverend, et al., "Synthesis and Biological Evaluation of 3-Deazacytidine and 3-Deazauridine Derivatives", Nucleosides and Nucleotides, 5(2):125-34 (1986).
Li, et al., "Alteration of the cleavage distance of Fok I restriction endonuclease by insertion mutagenesis", PNAS,, 90:2764-8 (1993).
Li, et al., "Functional domains in Fok I restriction endonuclease", PNAS, 89(10):4275-9 (1992).
Libby and Tanaka, "The molecular bases of restenosis", Prog Cardiovasc Dis 40:97-106 (1997).
Long, et al., "The subunit structure and subunit interactions of cytidine triphosphate synthetase", J. Biol. Chem., 245:80-7 (1970).
Malmquist, et al., Proc. West. Pharmacal. Soc., 2001:57-60 (1998).
McNamara, et al., "Synthesis, antitumor activity, and antiviral activity of 3-substituted 3-deazacytidines and 3-substituted 3-deazauridines", JBC, 33(7):2006-11 (1990).
McPartland, et al., "Cytidine 5'-triphosphate synthetase as a target for inhibition by the antitumor agent 3-deazauridine", Cancer Res., 34: 3107-3111 (1974).
Miller, et al., "A TALE nuclease architecture for efficient genome editing", Nature Biotechnol., 29: 143-8 (2011).
Miller, et al., "Redesign of retrovirus packaging cell lines to avoid recombination leading to helper virus production", Mol. Cell. Biol. 6:2895-902 (1986).
Mitani, et al., "Transduction of human bone marrow by adenoviral vector", Hum. Gene Ther., 5:941-8 (1994).
Momparler, et al., "Synergistic action of 5-azo-2'-deoxycytidine and 3-deazauridine on L1210 leukemic cells and EMT6 tumor cells", Cancer Res., 39 (10):3822-7 (1979).
Morishita, et al., "A gene therapy strategy using a transcription factor decoy of the E2F binding site inhibits smooth muscle proliferation in vivo", PNAS, , 92:5855-9 (1995).
Moyer, et al., "Antitumor activity and biochemical effects of cyclopentenyl cytosine in mice", Cancer Res., 46:3325-9 (1986).
Murakami, et al., "Activated protein C prevents LPS-induced pulmonary vascular injury by inhibiting cytokine production", Am J Physiol.., 272:L197-L202 (1997).
Naidini, et al., "In vivo gene delivery and table transduction of nondividing cells by a lentiviral vector", Science, 272:263-7 (1996).
Noda-Heiny and Sobel, "Vascular smooth muscle cell migration mediated by thrombin and urokinase receptor", Am J Physiol 268:C1195-1201(1995).
Ostrander, et al., "Effect of CTP synthetase regblation by CTP on synthesis in *Saccharomyces cerevisae*", J. Biol. Chem., 273:18992-19001 (1998).

Pastan, et al., "A retrovirus carrying an MDR1 cDNA confers multidrug resistance and polarized expression of P-glycoprotein in MDCK cells", PNAS,. 85:4486-90 (1988).
Payne, et al., "Uridine kinase from Ehrlich ascites carcinoma. Purification and properties of homogeneous enzyme", J. Biol. Chem., 260:10242-7 (1985).
Pouti, et al., "Phase I clinical trial of continuous infusion cyclopentenyl cytosine", Cancer Chemother. Pharmacol., 36:513-23 (1995).
Postel, et al., "Double knockout Nme1/Nme2 mouse model suggests a critical role for NDP kinases in erythroid development", Mol. Cell. Biochem., 329:45-50 (2009).
Salu, et al., "Drug-eluting stents: a new treatment in the prevention of restenosis. Part I: Experimental studies", Acta Cardiol, 59(1):51-61 (2004).
Sandeck, et al., "Genome-wide profile of pleural mesothelioma versus parietal and visceral pleura: the emerging gene portrait of the mesothelioma phenotype", PLoS One., 4 (8): e6554 (2009).
Schimmel, et al., "Cyclopentenyl cytosine (CPEC): an overview of its in vitro and in vivo activity", Curr. Cancer Drug Targets.; 7:504-9 (2007).
Schimmel, et al., "Formulation, quality control and shelf life of the experimental cytostatic drug cyclopentenyl cytosine", Drug Dev. Ind. Pharm., 32(4):497-503 (2006).
Schwartzenberger, et al., "Targeted gene transfer to human hematopoietic progenitor cell lines through the c-kit receptor", Blood, 87:472-8 (1996).
Shannon, et al., "Evaluation of carbocyclic analog of cytidine, and related carbocyclic analogs of pyrimidine nucleosides for antiviral activity against human influenza Type A viruses", Antimicrob Agents Chemother., 20(6):769-76 (1981).
Shealy, et al., "9-[$2$-DL-2a,3a-Dihydroxy-$4^2$-(hydroxymethyl)-cyclopentyl] adenine, the Carbocyclic Analog of Adenosine1,2", J. Am. Chem. Soc., 88:3885-7 (1966).
Sill, et al., "Cell division cycle 7 is a novel regulator of transforming growth factor-2-induced smooth muscle cell differentiation", J. Biol. Chem., 287:6860-7 (2012).
Shi et al., "Response gene to complement 32 promotes vascular lesion formation through stimulation of smooth muscle cell proliferation and migration", Arterioscler. Thromb. Vasc. Biol., 31:e19-e26 (2011).
Sousa, et al., "New frontiers in cardiology: drug-eluting stents: Part II". Circulation, 107:2383-9 (2003b).
Sousa, et al., "New frontiers in cardiology: drug-eluting stents: Part I". Circulation, 107:2274-9 (2003a).
Sousa, et al., "Sirolimus-eluting stent for the treatment of in-stent restenosis: a quantitative coronary angiography and three-ditensional intravascular ultrasound study", Circulation, 107(1):24-7 (2003d).
Sousa, et al., "Two-year angiographic and intravascular ultrasound follow-up after implantation of sirolimus-eluting stents in human coronary arteries". Circulation, 107 (3):381-3 (2003c).
Stouffer, et al., "Beta3 integrins are upregulated after vascular injury and modulate thrombospondin- and thrombin-induced proliferation of cultured smooth muscle cells", Circulation, 97:907-15 (1998).
Sullivan, et al., "Pharmacokinetic and phase I study of intravenous DON (6-diazo-5-oxo-L-norieucine) in children", Cancer Chemother Pharmacol., 21(1):78-84 (1988).
Tanguay, et al., "Current status of biodegradable stents", Cardiology Clinics, 12:699-713 (1994).
Tulis, "Rat carotid artery balloon injury model.", Methods Mol. Med., 139:1-30 (2007).vbTab.
Ueda, et al., "Smooth muscle cell de-differentiation is a fundamental change preceding wound healing after percutaneous transluminal coronary angioplasty in humans", Coron Artery Dis 6:71-81 (1995).
Ui-Tei, et al., "Sensitive assay of RNA interference in *Drosophila* and Chinese hamster cultured cells using firefly luciferase gene as target", FEBS Lett., 479:79-82 (2000).
Van Der Giessen, et al., "Marked Inflammatory Sequelae to Implantation of Biodegradable and Nonbiodegradable Polymers in Porcine Coronary Arteries",, Circulation, 94:1690-1697 (1996).
Vinogradov, et al, "Polyplex Nanogel formulations for drug delivery of cytotoxic nucleoside analogs", J. Control Release, 107(1):143-57 (2005).

(56) References Cited

OTHER PUBLICATIONS

Vinogradov, "Polymeric nanogel formulations of nucleoside analogs", Expert Opin Drug Deliv. 4(1): 5-17 (2007).
Werner, et al., "Intravenous transfusion of endothelial progenitor cells reduces neointima formation after vascular injury", Circ. Res., 93:e17-e24 (2003).
Wickline, et al., "Applications of nanotechnology to atherosclerosis, thrombosis, and vascular biology", Arterioscler Thromb Vasc Biol., 26:435-441 (2006).
Schimmel et al., "Absence of cardiotoxicity of the experimental cytotoxic drug cyclopentenyl cystosine (CPEC) in rats," 79(5):268-276 (2005) (Abstract).
Schimmel et al., "Cyclopentenyl Cytostine (CPEC): an overview of it's in vitro and in vivo activity," 7:15-30 (2007).
Tanaka et al., "Blockade of cytidine triphosphate synthase regulates smooth muscle cell and endothelial cell proliferation differentially," Arteriosclerosis, Thrombosis, and Vascular Biology, 33(10):2286-2287 (2013).
Tang et al., "Smooth muscle-specific drug targets for next-generation drug-eluting stent," 12(1):21-23 (2014).
International Search Report for PCT/US2014/037955 dated Dec. 23, 2014.

\* cited by examiner

COMPOSITIONS AND METHODS FOR REDUCING NEOINTIMA FORMATION

CROSS-REFERENCE TO RELATED APPLICATIONS

This application is a continuation-in-part of International Application No. PCT/US2014/037955 filed May 14, 2014, which claims benefit of U.S. Provisional Application No. 61/823,163, filed May 14, 2013, and the contents of each of which are incorporated by reference herein in its entireties.

STATEMENT REGARDING FEDERALLY SPONSORED RESEARCH OR DEVELOPMENT

This invention was made with Government Support under Agreement HL107526 awarded by the National Institutes of Health. The Government has certain rights in the invention.

REFERENCE TO SEQUENCE LISTING

The Sequence Listing submitted as a text file named "UGA_2021_PCT_ST25.txt," created on May 13, 2014, and having a size of 14,231 bytes is hereby incorporated by reference pursuant to 37 C.F.R. § 1.52(e)(5).

FIELD OF THE INVENTION

The field of the invention is generally related to compositions, devices, and methods for enhancing recovery from vascular injury or surgery, and reducing morbidity and mortality associated with neointima and restenosis.

BACKGROUND OF THE INVENTION

Neointimal hyperplasia is one of the major obstacles limiting the long-term clinical efficiency of cardiovascular intervention including angioplasty, bypass, and transplantation arteriopathy, etc., (Degertekin, et al., *Circulation.*, 106: 1610-1613 (2002)). Neointima formation also contributes to the development and progression of several proliferative cardiovascular diseases such as atherosclerosis, hypertension, and diabetic vascular complications (Frank, et al., *Curr. Opin. Lipidol.*, 15:523 (2004)). Under pathological conditions, vascular injury causes denudation of endothelial layer, which triggers a series of acute and chronic inflammatory responses characterized by the production of various different growth factors or inflammatory cytokines (Murakami, et al., *Am J Physiol Lung Cell Mol Physiol.*, 272: L197-L202 (1997); Cotran, et al., *J Am Soc Nephrol.*, 1:225-235 (1990)). Media layer smooth muscle cell (SMC) proliferation and migration in response to the injury-induced factors (such as platelet-derived growth factor, or PDGF) are essential events contributing to subsequent neointimal thickening (Fingerle, et al., *Proc Natl Acad Sci.*, 86:8412 (1989); Clowes, et a., *Circ. Res.*, 56:139-145 (1985)) which eventually leads to vessel narrowing. Re-endothelialization halts neointima formation and initiates the successful vascular repair (Bauters, et al., *Prog. Cardiovasc. Dis.*, 40:107-116 (1997); Kinlay, et al., *Curr. Opin. Lipidol.*, 12:383 (2001)). However, currently available anti-neointimal drugs indiscriminately block the proliferation of both SMCs and endothelial cells (EC), leading to impaired re-endothelialization and prolonged wound healing process. There remains a need to develop an anti-proliferation strategy that is SMC-sensitive.

Therefore, it is an object of the invention to provide compositions, devices, grafts, and methods of use thereof for reducing or preventing smooth muscle cell proliferation in a subject.

It is a further object of the invention to provide compositions, devices, grafts, and methods of use thereof for promoting or enhancing re-endothelialization in a subject.

It is also an object of the invention to provide compositions, methods, and devices for reducing or preventing neointima formation, restenosis, or a combination thereof in a subject.

SUMMARY OF THE INVENTION

Compositions, devices, grafts, and methods for reducing or preventing anti-neointima following cardiovascular injuries and interventions are disclosed. The compositions, devices, grafts, and methods are effective to reduce proliferation of vascular smooth muscle cells, without substantially reducing the proliferation of endothelial cells. Accordingly, re-endothelialization is accelerated in treated subjects.

The compositions typically include one or more cytidine-5'-triphosphate synthase 1 (also referred to as CTP synthase 1 and CTPS1) inhibitors in an amount effective to reduce proliferation of vascular smooth muscle cells (VSMC) in a subject. Preferably, the CTPS1 inhibitor reduces VSMC proliferation to a greater degree than the inhibitor reduces endothelial cell proliferation in the subject. In some embodiments, the composition does not substantially reduce the proliferation of endothelial cells in the subject. The compositions can include an effective amount of CTPS1 inhibitor to reduce neointima formation, permit or promote re-endothelialization, or a combination thereof at a site of vascular injury, a site of surgery, or a site of implantation of a vascular implant in the subject.

Disclosed CTPS1 inhibitors include nucleoside analogs such as cyclopentenyl cytosine, 3-deazauridine (3-DU), carbodine; glutamine analogs such as 6-diazo-5-oxo-L-norleucin (DON), and acivicin; functional nucleic acids designed to reduce expression of the CTPS1 gene or a gene product thereof; and polypeptides that reduces expression of the CTPS1 gene or a gene product thereof. In some embodiments the CTPS1 inhibitor is an antisense molecule, siRNA, miRNA, aptamers, ribozymes, triplex forming molecules, RNAi, or external guide sequences that target SEQ ID NO:1, or a gene editing composition such as CRISPR/Cas, zinc finger nuclease, or TALEN compositions that target the CTPS1 gene and reduce or otherwise modify its expression.

In some embodiments, the composition includes a delivery vehicle for delivering the CTPS1 inhibitor to vascular smooth muscle cells. The delivery vehicle can be, for example, nanoparticles, microparticles, micelles, synthetic lipoprotein particles, liposomes, or carbon nanotubes.

The composition can include a targeting signal for enhancing delivery of the CTPS1 inhibitor to vascular smooth muscle cells. The targeting signal can facilitate binding of the composition to smooth muscle cells by targeting a cell surface ligand such as Tissue Factor or $\alpha_v\beta_3$ integrin; or the targeting signal can target the compositions to the vicinity of vascular injuries by binding to a marker of clots or thrombosis such as fibrin, gpIIb/IIIa, tissue factor/VIIA complex, activated clotting factor Xa, activated clotting factor IXa, or the fibrin condensation product d-dimer. The targeting signal can be operably linked to the CTPS1 inhibitor or to the delivery vehicle.

Medical devices that are coated with or otherwise incorporate a composition including a CTPS1 inhibitor are also disclosed. Disclosed devices include, but are not limited to, implants, needles, cannulas, catheters, shunts, stents, balloons, and valves. In preferred embodiments, the device is a stent, for example, a drug eluting stent that elutes a composition including a CTPS1 inhibitor. The CTPS1 inhibitor can increase re-endothelialization at the site of intervention and reduce or prevent stenosis or restenosis.

Vascular grafts that are coated with or otherwise incorporate a composition including a CTPS1 inhibitor are also disclosed. The vascular graft can be autologous, preserved autologous, allogeneic, xenogenic or synthetic. Ex vivo treatment of the graft with a CTPS1 inhibitor prior to implantation can increase re-endothelialization at the site of surgery and reduce or prevent stenosis or restenosis.

Methods of reducing proliferation of vascular smooth muscle cells, methods of reducing or preventing neointima formation, and methods for promoting re-endothelialization in a subject are also disclosed. The methods typically include administering to the subject a composition, device, or graft that includes an effective amount of CTPS1 inhibitor to reduce proliferation of smooth muscle cells. The subject can have restenosis or another vascular proliferation disorder, or have been identified as being at risk for restenosis or another vascular proliferation disorder. In some embodiments, the subject has undergone, is undergoing, or will undergo vascular trauma, angioplasty, vascular surgery, or transplantation arteriopathy.

Some methods include co-administering to the subject one or more additional therapeutic agents. The additional therapeutic agents can be additional anti-neointima agents, chemotherapeutic agents, antibodies, antibiotics, antivirals, steroidal and non-steroidal anti-inflammatories, conventional immunotherapeutic agents, immunosuppressants, cytokines, chemokines, and growth factors.

In some embodiments, the methods include co-administering to the subject cytidine or a cytidine analog.

DETAILED DESCRIPTION OF THE INVENTION

I. Definitions

Figure 1A:
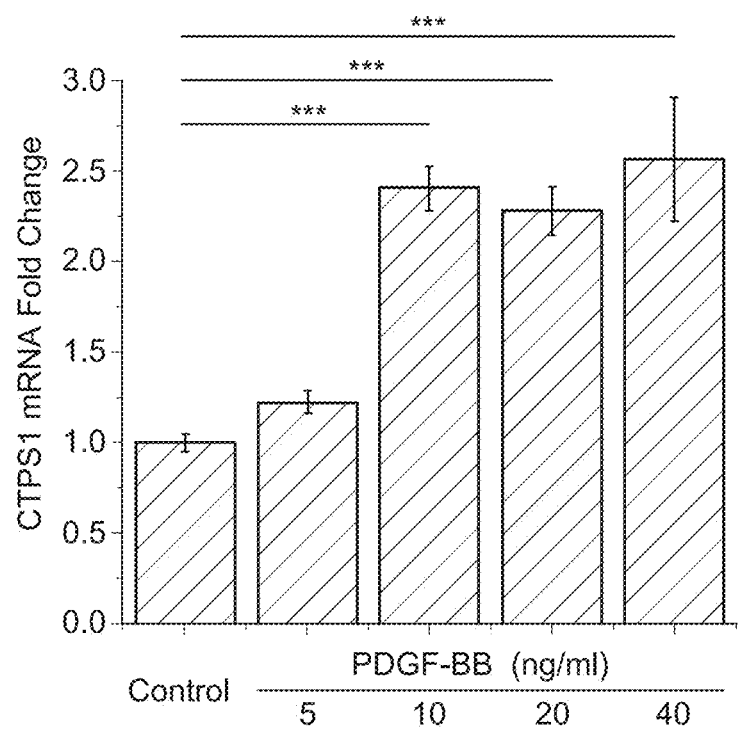
FIG. 1A is a bar graph showing CTPS1 mRNA expression (fold change) in control, and PDGF-BB treated (5 ng/ml, 10 ng/ml, 20 ng/ml or 40 ng/ml) proliferating smooth muscle cells (SMC).

"Identity," as known in the art, is a relationship between two or more polypeptide sequences, as determined by comparing the sequences. In the art, "identity" also means the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988). Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

"Pharmaceutically acceptable carrier" encompasses any of the standard pharmaceutical carriers, such as a phosphate buffered saline solution, water and emulsions such as an oil/water or water/oil emulsion, and various types of wetting agents.

"Inhibit" or other forms of the word such as "inhibiting" or "inhibition" means to hinder or restrain a particular characteristic. It is understood that this is typically in relation to some standard or expected value, in other words it is relative, but that it is not always necessary for the standard or relative value to be referred to. For example, "inhibits CTP synthase 1" means hindering or restraining the activity of the enzyme relative to a standard or a control. "Inhibits CTP synthase 1" can also mean to hinder or restrain the synthesis or expression of the enzyme relative to a standard or control.

"Treatment" or "treating" means to administer a composition to a subject or a system with an undesired condition (e.g., restenosis or other vascular proliferative disorder). The condition can include a disease. "Prevention" or "preventing" means to administer a composition to a subject or a system at risk for the condition. The condition can include a predisposition to a disease. The effect of the administration of the composition to the subject (either treating and/or preventing) can be, but is not limited to, the cessation of a particular symptom of a condition, a reduction or prevention of the symptoms of a condition, a reduction in the severity of the condition, the complete ablation of the condition, a stabilization or delay of the development or progression of a particular event or characteristic, or minimization of the chances that a particular event or characteristic will occur. It is understood that where treat or prevent are used, unless specifically indicated otherwise, the use of the other word is also expressly disclosed.

"Subject," "individual," and "patient" refer to any individual who is the target of treatment using the disclosed compositions. The subject can be a vertebrate, for example, a mammal Thus, the subject can be a human. The subjects can be symptomatic or asymptomatic. The term does not denote a particular age or sex. Thus, adult and newborn subjects, whether male or female, are intended to be covered. A subject can include a control subject or a test subject.

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

"Localization Signal or Sequence or Domain or Ligand" or "Targeting Signal or Sequence or Domain or Ligand" are used interchangeably and refer to a signal that directs a molecule to a specific cell, tissue, organelle, or intracellular region. The signal can be polynucleotide, polypeptide, or carbohydrate moiety or can be an organic or inorganic compound sufficient to direct an attached molecule to a desired location.

A "graft" is a tissue for transplantation. This may be in the form of cells or non-dissociated tissue. It may or may not have been treated prior to implantation to sterilize, modify, or cleanse the graft. Grafts include autograft, allograft, and synthetic tissues and organs, tissues produced by tissue engineering and non-biological medical devices by attachment of specific ligands (i.e. counter ligands attached to each surface) or by electrostatic or other non-covalent means.

"Microparticles" refers to particles having a diameter between one micron and 1000 microns, typically less than 400 microns, more typically less than 100 microns, most preferably for the uses described herein in the range of less than 10 microns in diameter. Microparticles include microcapsules and microspheres unless otherwise specified.

"Nanoparticles" refer to particles having a diameter of less than one micron, more typically between 50 and 1000 nanometers, preferably in the range of 100 to 300 nanometers.

"Implantation" refers to placement of a graft within the body. This may be by surgical means or minimally invasive means such as a catheter or by injection or infusion into a tissue.

II. Compositions for Reducing or Preventing Neointima Formation

Drug-eluting stents (DES) are a common treatment for coronary artery diseases. However, anti-proliferative drugs currently used in the clinic such as sirolimus-(Cypher) and paclitaxel-(Taxus) have side effects causing defective re-endothelialization and increasing risk of late thrombosis. It has been discovered that blockade of CTPS1 function reduces smooth muscle cell (SMC) proliferation and accelerates re-endothelialization.

Proliferative SMCs are known to produce various paracrine factors such as endostatin and thrombospondin to inhibit endothelial cell proliferation. Therefore, reduction of proliferating SMCs also benefits re-endothelialization as long as endothelial cell proliferation is not also inhibited. It has been discovered that this can be achieved by activating the CTP salvage pathway. Salvage pathway enzymes such as NME2 appear to be expressed at a relatively low level in normal endothelial cell growth conditions. However, when CTPS activity is blocked, NME2 is dramatically induced in endothelial cells while neointima proliferating SMCs are significantly reduced. The combined effect of blocking CTPS1 on inhibiting SMC proliferation while sustaining endothelial cell proliferation results in the accelerated re-endothelialization in endothelial cell-denuded vessels.

Compositions for preventing or reducing neointima formation and promoting re-endothelialization by blocking CTPS1 activity during vascular remodeling are disclosed.

A. CTPS Inhibitors

The compositions disclosed herein typically include an inhibitor of cytidine-5'-triphosphate synthase 1 (CTPS1) that blocks, reduces, or inhibits expression, activity, or bioavailability of CTPS1. CTP synthase 1 (also referred to as CTP synthetase and CTPS1) is a metabolic enzyme that catalyzes CTP biosynthesis from UTP, ATP and glutamine, an essential step for DNA and RNA synthesis during cell proliferation (Ostrander, *J. Biol. Chem.*, 273:18992-19001 (1998); Long, *J. Biol. Chem.*, 245:80-87 (1970)). The enzyme is important in the biosynthesis of phospholipids and nucleic acids, and plays a role in cell growth, development, and tumorigenesis.

It has been discovered that CTPS1 is induced smooth muscle cells (SMCs), but not endothelial cells (ECs) during vascular remodeling. Therefore, reducing CTPS1 function can suppresses SMC proliferation and neointima formation while promoting re-endothelialization in injured vessels. CTPS1 function can be reduced by blocking, reducing, or inhibiting CTPS1 gene expression or expression of a CTPS1 gene product. CTPS1 can also be reduced by blocking, reducing, or inhibiting activity of CTPS1 enzymatic activity. CTPS1 can also be reduced by reducing or inhibiting the bioavailability or bioactivity of CTPS1 for example by increasing turnover or degradation of CTPS1 mRNA or protein.

A number of compounds that block, reduce, or inhibit CTPS1 expression or activity, and dosages and formulations thereof are known in the art and discussed in more detail below. Some of the compounds have exhibited some toxicity to subjects in pre-clinical and clinical trials. It is believed, however, that the dosage for reducing neointima formation and promoting re-endothelialization can be lower than the dosages for treating cancer. As discussed in more detail below, in some embodiments the compositions are delivered locally to the site of treatment, which reduces toxicity associated with systemic delivery.

Classes of CTP synthase inhibitors discussed below include nucleoside analogues, glutamine analogs, and functional nucleic acids.

1. Nucleoside Analog Inhibitors of CTPS1

The CTPS1 inhibitor can be a nucleoside or nucleotide analog.

a. Cyclopentenyl Cytosine

In some embodiments the nucleoside or nucleotide analog is cyclopentenyl cytosine (CPEC), or a derivative, analogue or prodrug, or a pharmacologically active salt thereof. CPEC is an analogue of cytidine in which the ribose moiety is substituted by a carbocyclic sugar. CPEC has the structure:

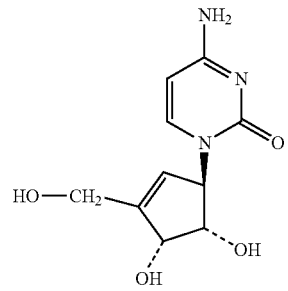 [SMILES: Nc1ccn([C@@H]2C=C(CO)[C@@H](O)[C@H]2O)c(=O)n1]

Cyclopentenyl cytosine (CPEC, or CPE-C) is converted to the active metabolite cyclopentenyl cytosine 5'-triphosphate (CPEC-TP); CPEC-TP competitively inhibits cytidine triphosphate (CTP) synthase, thereby depleting intracellular cytidine pools and inhibiting DNA and RNA synthesis. CPEC has been proposed as an anticancer and antiviral therapy. See, for example, Schimmel, et al., Cyclopentenyl Cytosine (Cpec): An Overview of its in vitro and in vivo activity," Chapter 2 in *Current Cancer Drug Targets* 7:325-334 (2007), which is specifically incorporated herein by reference in its entirety.

Other cyclopentenyl cytosine based analogs are also known in the art. See, for example, U.S. Published Application No. 2009/0270431, which is specifically incorporated by reference in its entirety and provides a hydroxyl protected cyclopentenyl cytosine analog, a protected-2'-fluoro-cyclopentenyl cytosine analog, and others.

CPEC has been the subject of clinical trials for the treatment of cancer. Formulations and dosages for treating human subjects are known in the art. See, for example, Politi, et al., *Cancer Chemother. Pharmacol.*, 36(6):513-23 (1995) and Schimmel, et al., *Drug Dev. Ind. Pharm.*, 32(4): 497-503 (2006), Tanaka and Sata, *Arterioscler Thromb Vasc Biol.*, 33(10):2286-7 (2013) all of which are specifically incorporated by reference in their entireties.

b. 3-Deazauridine (3-DU)

In some embodiments the nucleoside or nucleotide analog is 3-deazauridine (3-DU), or a derivative, analog or prodrug, or a pharmacologically active salt thereof 3-DU is a uridine analog having the structure:

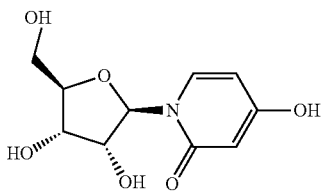 [SMILES: O=c1cc(O)ccn1[C@@H]1O[C@H](CO)[C@@H](O)[C@H]1O]

3-DU is not incorporated into nucleic acids. However, after its conversion to 3-deazauridine 5'-triphosphate, it produces a potent inhibition of CTP synthetase (McPartland, et al., *Cancer Res.*, 34: 3107-3111 (1974)). Inhibition of CTPS1 by the nucleotide form of 3-DU produces a marked depletion of the intracellular pool of CTP and dCTP (Brockman, *Ann. NY. Acad. Sci.*, 225:501-521 (1975), and has been tested as an anti-cancer and anti-viral therapy (Momparler, et al., *Cancer Res.*, 39(10):3822-7 (1979), Gao, et al., *Nucleosides, Nucleotides Nucleic Acids*, 19:371-377 (2000)).

Formulations and dosages including 3-DU are discussed in U.S. Pat. No. 3,836,645, and analogs thereof are discussed in Lalut, et al., *Bioorg. Med. Chem. Lett.*, 22(24):7461-4 (2012), WO/2011/070152, McNamara, et al., *JBC*, 33(7): 2006-11 (1990), and Legraverend, et al., *Nucleosides and Nucleotides*, 5(2):125-134 (1986), each of which is specifically incorporated by reference herein in its entirety.

c. Carbodine

In some embodiments the nucleoside or nucleotide analog is carbodine, or a derivative, analog or prodrug, or a pharmacologically active salt thereof. Carbodine is a nucleoside analog of cytidine. The structures for (−)-carbodine, (+)-carbodine are:

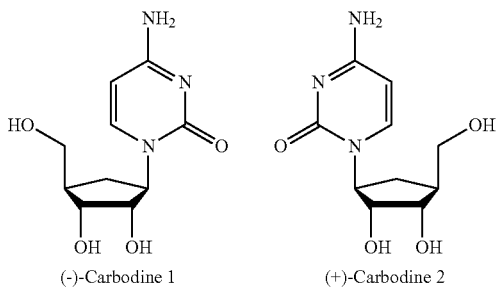

Carbodine is termed a "carbocyclic analog" which refers to nucleoside analogs in which the tetrahydrofuran ring of the parent nucleoside is replaced by the cyclopentane ring (Shealy, et al., *J. Am. Chem. Soc.*, 88:3885-3887 (1966)). Carbodine, related carbocyclic analogs, and formulations and dosages thereof are known in the art and have been tested for their antiviral activity. See, for example, Shannon, et al., *Antimicrobial Agents and Chemotherapy*, 20(6):769-776 (1981), Georges-Courbot, et al., *Agents Chemother.*, 50:1768-1772 (2006), Julander, et al., *Antiviral Res.*, 80(3): 309-15 (2008), and U.S. Pat. No. 8,242,120, each of which is specifically incorporated by reference herein in its entirety.

2. Glutamine Analog Inhibitors CTPS1

The CTPS1 inhibitor can be a glutamine analog or antagonist. Large neutral amino acid L-glutamine antagonists include 6-diazo-5-oxo-L-norleucine (L-DON), and L-[αS, 5S]-α-amino-3-chloro-4,5-dihydro-5-isoxazoleacetic acid, also known as acivicin, are described in Ahluwalia, G. S., et al, *Pharmac. Ther.*, 42(16):243-271 (1990), which is specifically incorporated by reference herein in its entirety.

a. 6-diazo-5-oxo-L-norleucin (DON)

In some embodiments the glutamine analog or antagonist is 6-diazo-5-oxo-L-norleucin (DON), or a derivative, analog or prodrug, or a pharmacologically active salt thereof. DON is a glutamine antagonist, which was isolated originally from Streptomyces in a sample of Peruvian soil. DON has the structure:

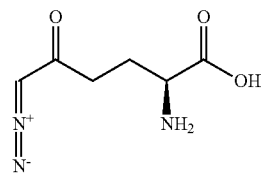 [SMILES: [N-]=[N+]=CC(=O)CC[C@H](N)C(=O)O]

Due to its similarity to glutamine, DON can enter catalytic centers of glutamine utilizing enzymes such as CTP synthase, and inhibits them by alkylation. DON has been the subject of limited clinical trials since 1957 for the treatment of cancer and more recently infectious diseases (see, for example, Catane, et al., *Cancer Treat. Rep.*, 63, 1033-1038 (1979); and Ahluwalia, et al. *Pharmacol. Ther.* 46, 243-271 (1990)). U.S. Pat. No. 2,965,634 describes norleucine derivatives, such as DON, and a process for the production thereof. Dosages and formulations are also known in the art. See, for example, Sullivan, et al., *Cancer Chemother Pharmacol.*, 21(1):78-84 (1988), Hofer, et al., PNAS, 98(11): 6412-6416 (2001), Carcamo, et al., *PLoS ONE*, 6(12): e29690. doi:10.1371/journal.pone.0029690 (2011), each of which is specifically incorporated by reference herein in its entirety. For example, for L-DON, the dosage can range from 0.1-1.1 mg/kg/day for oral administration and from 0.2-0.6 mg/kg/day for intramuscular or intravenous administration.

b. Acivicin

In some embodiments the glutamine analog or antagonist is L-[αS,5S]-α-amino-3-chloro-4,5-dihydro-5-isoxazoleacetic acid (acivicin), or a derivative, analog or prodrug, or a pharmacologically active salt thereof. Acivicin has the structure:

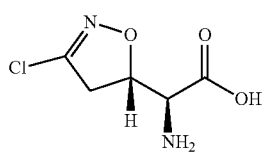 [SMILES: N[C@H](C(=O)O)[C@@H]1CC(Cl)=NO1]

3-bromoacivicin has a profile similar to that of acivicin in tests against a panel of tumor cell lines (Conti, et al., *Farmaco,* 58(9):683-90 (2003), and was found to be a CTP synthetase inhibitor three times as potent as its 3-chloro analog (Conti, et al, *Chem Med Chem,* 6(2): 329-333 (2011)), each of which are specifically incorporated by reference herein in its entirety.

Acivicin has been the subject of clinical trials for the treatment of cancer. Dosages and formulations are known in the art, see, for example, Hidalgo, *Clinical Cancer Research,* 4(11): 2763-2770 (1998), U.S. Pat. Nos. 3,856,807, 3,878,047, and 5,087,639 each of which is specifically incorporated by reference herein in its entirety. For example, for acivicin, the dosage can range from 12-25 mg/square meter of body surface per day and administration is carried out intravenously as a bolus injection or by continuous infusion. Acivicin is also described in U.S. Pat. No. 5,489,562.

3. Other Compounds that Inhibit CTPS1

Other suitable compounds are described in WO 2014/170435, and include, for example, gemcitabine (2',2'-difluorodeoxycytidine, dFdC), actinomycin D, cycloheximide, dibutyryl cyclic AMP, and 6-azauridine.

4. Functional Nucleic Acids Inhibitors of CTPS1

The CTPS1 inhibitor can be a functional nucleic acid. Functional nucleic acids are nucleic acid molecules that have a specific function, such as binding a target molecule or catalyzing a specific reaction. As discussed in more detail below, functional nucleic acid molecules can be divided into the following non-limiting categories: antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the polypeptide itself. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Therefore the compositions can include one or more functional nucleic acids designed to reduce expression of the CTPS1 gene, or a gene product thereof.

a. CTPS1 Sequences

In some embodiments, the composition includes a functional nucleic acid or polypeptide designed to target and reduce or inhibit expression or translation of CPTS1 mRNA; or to reduce or inhibit expression, reduce activity, or increase degradation of CPTS1 protein. In some embodiments, the composition includes a vector suitable for in vivo expression of the functional nucleic acid.

Nucleic acid and amino acid sequences for CTPS1 are known in the art. See, for example, NCBI Reference Sequence: NM_001905.2, *Homo sapiens CTP synthase* 1 (CTPS1), mRNA, which provides the nucleic acid sequence:

(SEQ ID NO: 1)

```
  1 tccctcgccc ggaggcagag atgcgctggc gcatcaccgc caggagccca cagtgaaaga
 61 ccatcggatg gaaggcgacg cccagaactc caggagaccg ctgtgggagg acgcgaggcc
121 aggtgacgaa taggccaggc gtgagttccc aaacagcctc ctcccctca agagagtaag
181 cttgggccac aggctgggac ggaagcagag gggcagacac gccaccaccc gcccggcctc
241 gaacctacgg cggcacagtt cagcggaggc ggcccagcgg tcctgtcccg cgcctgcgca
301 ctccaggccc cgccccgccc cgcgccctcc aggcccggcc cgccctccaa cctctgcgtg
361 cgcacagcct agagcccgcc tccgtgaaag actgccgggc gcatgcggtc ggggttgttc
421 actggctgtc cggggctccg cgcgcgtcgc cggcccagct ctgtcgctga cgggaggatc
481 tgaagccggc cgcaggtcaa agagtaaaat gaagtacatt ctggttactg gtggtgttat
541 atcaggaatt ggaaaaggaa tcattgccag cagtgtgggc acaatactca agtcatgtgg
601 tttacatgta acttcaatca aaattgaccc ctacattaac attgatgcag gaacattctc
661 tccttatgag catggtgagg tttttgtgct ggatgatggt ggggaagtag accttgacct
721 gggtaactat gagcggttcc ttgacatccg cctcaccaag gacaataatc tgaccactgg
781 aaagatatac cagtatgtca ttaacaagga acggaaagga gattacttgg ggaaaactgt
841 ccaagttgtc cctcatatca cagatgcaat ccaggagtgg gtgatgagac aggcgttaat
901 acctgtagat gaagatggcc tggaacctca agtgtgt tt attgagcttg gtgaaccgt
961 gggggacata gaaagcatgc cctttattga ggccttccgt cagttccaat tcaaggtcaa
```

-continued

```
1021 aagagagaac ttttgtaaca tccacgtcag tctagttccc cagccaagtt caacagggga 1081 acagaagact aaacctaccc agaatagtgt tcgggaactt agaggacttg ggctttcccc 1141 agatctggtt gtatgcaggt gctcaaatcc acttgacaca tcagtgaagg agaaaatatc 1201 aatgttctgc catgttgagc ctgaacaagt gatctgtgtc cacgatgtct catccatcta 1261 ccgagtcccc ttgttgttag aggagcaagg ggttgtagat tattttcttc gaagacttga 1321 ccttcctatt gagaggcagc caagaaaaat gctgatgaaa tggaaagaga tggctgacag 1381 atatgatcgc ttgctggaga cctgctctat tgcccttgtg ggcaaataca cgaagttctc 1441 agactcctat gcctctgtca ttaaggctct ggagcattct gcactggcca tcaaccacaa 1501 attggaaatc aagtacatag attctgcgga cttggagccc atcacctcgc aagaagagcc 1561 cgtgcgctac cacgaagctt ggcagaagct ctgtagtgct catggagtgc tggttccagg 1621 aggatttggt gttcgaggaa cagaaggaaa atccaagca attgcctggg ctcggaatca 1681 gaaaaagcct tttttgggcg tgtgcttagg gatgcagttg gcagtggttg aattctcaag 1741 aaacgtgctg ggatggcaag atgccaattc tacagagttt gaccctacga ccagtcatcc 1801 cgtggtcgta gacatgccag aacacaaccc agggcagatg ggcggaacca tgaggctggg 1861 caagaggaga accctgttcc agaccaagaa ctcagtcatg aggaaactct atggagacgc 1921 agactacttg gaagagaggc accgccaccg atttgaggtg aatccagtct ggaaaaagtg 1981 tttggaagaa caaggcttga agtttgttgg ccaagatgtt gaaggagaga gaatggaaat 2041 tgtggagtta gaagatcatc cctttttgt tggggttcag taccaccctg agttcctgtc 2101 caggcctatc aagccctccc caccatactt tggcctcctc ctggcctctg tggggcggct 2161 ctcacattac ctccagaaag gctgcaggct ctcacccagg gacacctata gtgacaggag 2221 tggaagcagc tcccctgact ctgaaatcac cgaactgaag tttccatcaa taaatcatga 2281 ctgatcttgt agcggatgat tcttcaagag acccttcaaa cttgggtaga gtttacagct 2341 ctgactttac actcggcttt ggagactttc tttaaattat gttttatta agattatttt 2401 attatgcgga aaggtatttg ggaaacttgt cacttgcatg tcccatcacg tgtactggct 2461 cctctgtggt gtctgcctgt tgcgtgacac tctccttgca gttcttgagt gcggcagaa 2521 catcgcgatg ggaaccgatg gtgggtgggg ctgcagagtg ccccatcggt caccttgttt 2581 ctcaactacc tcgcatcatt gcagatgcta gcgcgttgcc tgtcgctttc ccttggatac 2641 ctagaccgtt ataaagtgtg ccacatggac ttaccgagca tggagagagg attttagcta 2701 ggatttgaac acttggtgct gggaacctca gggtattgct tgccactaag ccatgaaacc 2761 agagacaaaa tctctatact gccctgagtt gggggaatt ctcagtgcca actgtgctg 2821 gtcctcattc aaagggacgg tcagtttggt gtcaacatga acaccaaga tgtctgtctc 2881 tgaagcgtga ttttaaaatc cccatgcctg tggctgcgct tcctatttct agggctggga 2941 aacactcctt gcatcaaggg gtcacttaca gaacaaagaa tcttttgggg gaaacttcct 3001 ctaaaccct ctcatatata gacagctttg actggagggt ccatttttct tccaggatgg 3061 tgttactgca gttgaaaggg caatatgaag ttactttctt aatgtgacct agcaataggc 3121 atagctacgt ggcactatat tctggccaga ctcgatgtgt actctaactt aagaaataaa 3181 tcagtaaggc agaacaagaa aaaaaaaaa aaaaaaa,
``` and the amino acid sequence (SEQ ID NO: 2)
```
MKYILVTGGV ISGIGKGIIA SSVGTILKSC GLHVISIKID

PYINIDAGTF SPYEHGEVFV LDDGGEVDLD LGNYERFLDI

RLIKDNNLTT GKIYQYVINK ERKGDYLGKT VQVVPHITDA

IQEWVMRQAL IPVDEDGLEP QVCVIELGGT VGDIESMPFI

EAFRQFQFKV KRENFCNIHV SLVPQPSSTG EQKTKPTQNS

VRELRGLGLS PDLVVCRCSN PLDTSVKEKI SMFCHVEPEQ

VICVHDVSSI YRVPLLLEEQ GVVDYFLRRL DLPIERQPRK

MLMKWKEMAD RYDRLLETCS IALVGKYTKF SDSYASVIKA

LEHSALAINH KLEIKYIDSA DLEPITSQEE PVRYHEAWQK

LCSAHGVLVP GGFGVRGTEG KIQAIAWARN QKKPFLGVCL

GMQLAVVEFS RNVLGWQDAN STEFDPTTSH PVVVDMPEHN

PGQMGGTMRL GKRRTLFQTK NSVMRKLYGD ADYLEERHRH

RFEVNPVWKK CLEEQGLKFV GQDVEGERME IVELEDHPFF

VGVQYHPEFL SRPIKPSPPY FGLLLASVGR LSHYLQKGCR

LSPRDTYSDR SGSSSPDSEI TELKFPSINH D.
```

In some embodiments, a functional nucleic acid or polypeptide is designed to target a segment of the nucleic acid sequence of SEQ ID NO:1, or the complement thereof, or a genomic sequence corresponding therewith, or variants thereof having a nucleic acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1.

In some embodiments, a functional nucleic acid or polypeptide is designed to target a segment of a the nucleic acid encoding the amino acid sequence of SEQ ID NO:2, or the complement thereof, or variants thereof having a nucleic acid sequence 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to a nucleic acid encoding the amino acid sequence of SEQ ID NO:2.

In some embodiments, the function nucleic acid hybridizes to the nucleic acid of SEQ ID NO:1, or a complement thereof, for example, under stringent conditions. In some embodiments, the functional nucleic acid hybridizes to a nucleic acid sequence that encodes SEQ ID NO:2, or a complement thereof, for example, under stringent conditions.

b. Functional Nucleic Acids i. Antisense

The functional nucleic acids can be antisense molecules. Antisense molecules are designed to interact with a target nucleic acid molecule through either canonical or non-canonical base pairing. The interaction of the antisense molecule and the target molecule is designed to promote the destruction of the target molecule through, for example, RNAse H mediated RNA-DNA hybrid degradation. Alternatively the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. Exemplary methods include in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

ii. Aptamers

The functional nucleic acids can be aptamers. Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $K_d$'s from the target molecule of less than $10^{-12}$ M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a molecule such as a polypeptide, that the background molecule be a different polypeptide.

iii. Ribozymes

The functional nucleic acids can be ribozymes. Ribozymes are nucleic acid molecules that are capable of catalyzing a chemical reaction, either intramolecularly or intermolecularly. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

iv. Triplex Forming Oligonucleotides

The functional nucleic acids can be triplex forming molecules. Triplex forming functional nucleic acid molecules are molecules that can interact with either double-stranded or single-stranded nucleic acid. When triplex molecules interact with a target region, a structure called a triplex is formed in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$.

v. External Guide Sequences

The functional nucleic acids can be external guide sequences. External guide sequences (EGSs) are molecules that bind a target nucleic acid molecule forming a complex, which is recognized by RNase P, which then cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukarotic cells. Representative examples of how to make and use EGS molecules to facilitate cleavage of a variety of different target molecules are known in the art.

vi. RNA Interference

In some embodiments, the functional nucleic acids induce gene silencing through RNA interference. Gene expression can also be effectively silenced in a highly specific manner through RNA interference (RNAi). This silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, et al. (2001) Genes Dev., 15:188-200; Bernstein, et al. (2001) Nature, 409:363-6; Hammond, et al. (2000) Nature, 404: 293-6). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, a siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs.

Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Co.), Glen Research (Sterling, Va.), MWB Biotech (Esbersberg, Germany), Proligo (Boulder, Co.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAse (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors.

In some embodiment, the functional nucleic acid is siRNA, shRNA, miRNA. In some embodiments, the composition includes a vector expressing the functional nucleic acid. Methods of making and using vectors for in vivo expression of functional nucleic acids such as antisense oligonucleotides, siRNA, shRNA, miRNA, EGSs, ribozymes, and aptamers are known in the art.

vii. Other Gene Editing Compositions

In some embodiments the functional nucleic acids are gene editing compositions. Gene editing compositions can include nucleic acids that encode an element or elements that induce a single or a double strand break in the target cell's genome, and optionally a polynucleotide. The compositions can be used, for example, to reduce or otherwise modify expression of CTPS1.

1. Strand Break Inducing Elements

CRISPR/Cas

In some embodiments, the element that induces a single or a double strand break in the target cell's genome is a CRISPR/Cas system. CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, *Science*, 15:339(6121):819-823 (2013) and Jinek, et al., *Science*, 337(6096):816-21 (2012)). By transfecting a cell with the required elements including a Cas gene and specifically designed CRISPRs, the organism's genome can be cut and modified at any desired location. Methods of preparing compositions for use in genome editing using the CRISPR/Cas systems are described in detail in WO 2013/176772 and WO 2014/018423, which are specifically incorporated by reference herein in their entireties.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Cong, *Science*, 15:339(6121):819-823 (2013) and Jinek, et al., *Science*, 337(6096):816-21 (2012)). A single fused crRNA-tracrRNA construct can also be referred to as a guide RNA or gRNA (or single-guide RNA (sgRNA)). Within an sgRNA, the crRNA portion can be identified as the 'target sequence' and the tracrRNA is often referred to as the 'scaffold'.

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.u-psud.fr/, a tool designed to help scientists find CRISPR targeting sites in a wide range of species and generate the appropriate crRNA sequences.

In some embodiments, one or more vectors driving expression of one or more elements of a CRISPR system are introduced into a target cell such that expression of the elements of the CRISPR system direct formation of a CRISPR complex at one or more target sites. While the specifics can be varied in different engineered CRISPR systems, the overall methodology is similar. A practitioner interested in using CRISPR technology to target a DNA sequence (such as CTPS1) can insert a short DNA fragment containing the target sequence into a guide RNA expression plasmid. The sgRNA expression plasmid contains the target sequence (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

Zinc Finger Nucleases

In some embodiments, the element that induces a single or a double strand break in the target cell's genome is a nucleic acid construct or constructs encoding a zinc finger nucleases (ZFNs). ZFNs are typically fusion proteins that include a DNA-binding domain derived from a zinc-finger protein linked to a cleavage domain.

The most common cleavage domain is the Type IIS enzyme Fokl. Fokl catalyzes double-stranded cleavage of DNA, at 9 nucleotides from its recognition site on one strand and 13 nucleotides from its recognition site on the other. See, for example, U.S. Pat. Nos. 5,356,802; 5,436, 150 and 5,487,994; as well as Li et al. *Proc., Natl. Acad. Sci. USA* 89 (1992):4275-4279; Li et al. *Proc. Natl. Acad. Sci. USA,* 90:2764-2768 (1993); Kim et al. *Proc. Natl. Acad. Sci. USA.* 91:883-887 (1994a); Kim et al. *J. Biol. Chem.* 269:31, 978-31,982 (1994b). One or more of these enzymes (or enzymatically functional fragments thereof) can be used as a source of cleavage domains.

The DNA-binding domain, which can, in principle, be designed to target any genomic location of interest, can be a tandem array of $Cys_2His_2$ zinc fingers, each of which generally recognizes three to four nucleotides in the target DNA sequence. The $Cys_2His_2$ domain has a general structure: Phe (sometimes Tyr)-Cys-(2 to 4 amino acids)-Cys-(3 amino acids)-Phe (sometimes Tyr)-(5 amino acids)-Leu-(2 amino acids)-His-(3 amino acids)-His. By linking together multiple fingers (the number varies: three to six fingers have been used per monomer in published studies), ZFN pairs can be designed to bind to genomic sequences 18-36 nucleotides long.

Engineering methods include, but are not limited to, rational design and various types of empirical selection methods. Rational design includes, for example, using databases including triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Published Application Nos. 2002/0165356; 2004/0197892; 2007/0154989; 2007/0213269; and International Patent Application Publication Nos. WO 98/53059 and WO 2003/016496.

Transcription Activator-Like Effector Nucleases

In some embodiments, the element that induces a single or a double strand break in the target cell's genome is a nucleic acid construct or constructs encoding a transcription activator-like effector nuclease (TALEN). TALENs have an overall architecture similar to that of ZFNs, with the main difference that the DNA-binding domain comes from TAL effector proteins, transcription factors from plant pathogenic bacteria. The DNA-binding domain of a TALEN is a tandem array of amino acid repeats, each about 34 residues long. The repeats are very similar to each other; typically they differ principally at two positions (amino acids 12 and 13, called the repeat variable diresidue, or RVD). Each RVD specifies preferential binding to one of the four possible nucleotides, meaning that each TALEN repeat binds to a single base pair, though the NN RVD is known to bind adenines in addition to guanine. TAL effector DNA binding is mechanistically less well understood than that of zinc-finger proteins, but their seemingly simpler code could prove very beneficial for engineered-nuclease design. TALENs also cleave as dimers, have relatively long target sequences (the shortest reported so far binds 13 nucleotides per monomer) and appear to have less stringent requirements than ZFNs for the length of the spacer between binding sites. Monomeric and dimeric TALENs can include more than 10, more than 14, more than 20, or more than 24 repeats.

Methods of engineering TAL to bind to specific nucleic acids are described in Cermak, et al, *Nucl. Acids Res.* 1-11 (2011). U.S. Published Application No. 2011/0145940, which discloses TAL effectors and methods of using them to modify DNA. Miller et al. *Nature Biotechnol* 29: 143 (2011) reported making TALENs for site-specific nuclease architecture by linking TAL truncation variants to the catalytic domain of Fokl nuclease. The resulting TALENs were shown to induce gene modification in immortalized human cells. General design principles for TALE binding domains can be found in, for example, WO 2011/072246.

2. Gene Altering Polynucleotides

The nuclease activity of the genome editing systems described herein cleave target DNA to produce single or double strand breaks in the target DNA. Double strand breaks can be repaired by the cell in one of two ways: non-homologous end joining, and homology-directed repair. In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence is used as a template for repair of the cleaved target DNA sequence, resulting in the transfer of genetic information from a donor polynucleotide to the target DNA. As such, new nucleic acid material can be inserted/copied into the site.

Therefore, in some embodiments, the genome editing composition optionally includes a donor polynucleotide. The modifications of the target DNA due to NHEJ and/or homology-directed repair can be used to induce gene correction, gene replacement, gene tagging, transgene insertion, nucleotide deletion, gene disruption, gene mutation, etc.

Accordingly, cleavage of DNA by the genome editing composition can be used to delete nucleic acid material from a target DNA sequence by cleaving the target DNA sequence and allowing the cell to repair the sequence in the absence of an exogenously provided donor polynucleotide. Alternatively, if the genome editing composition includes a donor polynucleotide sequence that includes at least a segment with homology to the target DNA sequence, the methods can be used to add, i.e., insert or replace, nucleic acid material to a target DNA sequence (e.g., to "knock in" a nucleic acid that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, the compositions can be used to modify DNA in a site-specific, i.e., "targeted", way, for example gene knock-out, gene knock-in, gene editing, gene tagging, etc. as used in, for example, gene therapy.

In applications in which it is desirable to insert a polynucleotide sequence into a target DNA sequence, a polynucleotide including a donor sequence to be inserted is also provided to the cell. By a "donor sequence" or "donor polynucleotide" or "donor oligonucleotide" it is meant a nucleic acid sequence to be inserted at the cleavage site. The donor polynucleotide typically contains sufficient homology to a genomic sequence at the cleavage site, e.g., 70%, 80%, 85%, 90%, 95%, or 100% homology with the nucleotide sequences flanking the cleavage site, e.g., within about 50 bases or less of the cleavage site, e.g., within about 30 bases, within about 15 bases, within about 10 bases, within about 5 bases, or immediately flanking the cleavage site, to support homology-directed repair between it and the genomic sequence to which it bears homology. The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence includes a non-homologous sequence flanked by two regions of homology, such that homology-directed repair between the target DNA region and the two flanking sequences results in insertion of the non-homologous sequence at the target region.

c. Oligonucleotide Composition

The functional nucleic acids can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose sugar linked by phosphodiester bonds.

In some embodiments, the oligonucleotides are composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein "modified nucleotide" or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA oligonucleotides of the same nucleobase sequence. For example, the oligonucleotide can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). In some embodiments, the analogs have a substantially uncharged, phosphorus containing backbone.

i. Heterocyclic Bases

The principal naturally-occurring nucleotides include uracil, thymine, cytosine, adenine and guanine as the heterocyclic bases. The oligonucleotides can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-.beta.-D-ribofuranosyl)pyridine (2-aminopyridine), and various pyrrolo- and pyrazolopyrimidine derivatives.

ii. Sugar Modifications

Oligonucleotides can also contain nucleotides with modified sugar moieties or sugar moiety analogs. Sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-O,4'-C-methylene (LNA), 2'-O-(methoxyethyl) (2'-OME) and 2'-O—(N-(methyl)acetamido) (2'-OMA). 2'-O-aminoethyl sugar moiety substitutions are especially preferred because they are protonated at neutral pH and thus suppress the charge repulsion between the TFO and the target duplex. This modification stabilizes the C3'-endo conformation of the ribose or dexyribose and also forms a bridge with the i−1 phosphate in the purine strand of the duplex.

In some embodiments, the functional nucleic acid is a morpholino oligonucleotide. Morpholino oligonucleotides are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of an oligomer:RNA heteroduplex to resist RNAse degradation.

In some embodiments, oligonucleotides employ morpholino-based subunits bearing base-pairing moieties, joined by uncharged linkages, as described above.

iii. Internucleotide Linkages

Oligonucleotides connected by an internucleotide bond that refers to a chemical linkage between two nucleoside moieties. Modifications to the phosphate backbone of DNA or RNA oligonucleotides may increase the binding affinity or stability oligonucleotides, or reduce the susceptibility of oligonucleotides nuclease digestion. Cationic modifications, including, but not limited to, diethyl-ethylenediamide (DEED) or dimethyl-aminopropylamine (DMAP) may be especially useful due to decrease electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g., Sterchak, E. P. et al., *Organic. Chem.*, 52:4202, (1987)), and uncharged morpholino-based polymers having achiral intersubunit linkages (see, e.g., U.S. Pat. No. 5,034,506), as discussed above. Some internucleotide linkage analogs include morpholidate, acetal, and polyamide-linked heterocycles.

In another embodiment, the oligonucleotides are composed of locked nucleic acids. Locked nucleic acids (LNA) are modified RNA nucleotides (see, for example, Braasch, et al., *Chem. Biol.*, 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the oligonucleotides are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are comprised of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as O-linkers), amino acids such as lysine are particularly useful if positive charges are desired in the PNA, and the like. Methods for the chemical assembly of PNAs are well known. See, for example, U.S. Pat. Nos. 5,539,082, 5,527,675, 5,623,049, 5,714,331, 5,736,336, 5,773,571 and 5,786,571.

Oligonucleotides optionally include one or more terminal residues or modifications at either or both termini to increase stability, and/or affinity of the oligonucleotide for its target. Commonly used positively charged moieties include the amino acids lysine and arginine, although other positively charged moieties may also be useful. Oligonucleotides may further be modified to be end capped to prevent degradation using a propylamine group. Procedures for 3' or 5' capping oligonucleotides are well known in the art.

In some embodiments, the functional nucleic acid can be single stranded or double stranded.

B. Targeting Signal or Domain

The compositions can be optionally modified to include one or more targeting signals, ligands, or domains. The targeting signal can be operably linked with the CTPS1 inhibitor, or a delivery vehicle such as a microparticle. For example, in some embodiments, the targeting signal is linked or conjugated directly or indirectly to the CTPS1 inhibitor. In some embodiments, the targeting signal is linked, conjugated, or associated directly, or indirectly, with a delivery vehicle such as a liposome or a nanoparticle. Delivery vehicles are discussed in more detail below. The targeting signal or sequence can be specific for a host, tissue, organ, cell, organelle, non-nuclear organelle, or cellular compartment.

In some embodiments, the targeting signal binds to its ligand or receptor which is located on the surface of a target cell such as to bring the composition or a delivery vehicle thereof and cell membranes sufficiently close to each other to allow penetration of the composition or delivery vehicle into the cell. In a preferred embodiment, the targeting molecule is selected from the group consisting of an antibody or antigen binding fragment thereof, an antibody domain, an antigen, a cell surface receptor, a cell surface adhesion molecule, a major histocompatibility locus protein, a viral envelope protein and a peptide selected by phage display that binds specifically to a defined cell.

Targeting the compositions or delivery vehicles to specific cells can be accomplished by modifying the disclosed compositions or delivery vehicles to express specific cell and tissue targeting signals. These sequences target specific cells and tissues, but in some embodiments the interaction of the targeting signal with the cell does not occur through a traditional receptor: ligand interaction. Eukaryotic cells have a number of distinct cell surface molecules. The structure and function of each molecule can be specific to the origin, expression, character and structure of the cell. Determining the unique cell surface complement of molecules of a specific cell type can be determined using techniques well known in the art.

One skilled in the art will appreciate that the tropism of the compositions or delivery vehicles described can be altered by merely changing the targeting signal. In one specific embodiment, compositions are provided that enable the addition of cell surface antigen specific antibodies to the composition or delivery vehicle for targeting the delivery the CTPS1 inhibitor to the target cells.

It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used a targeting moieties to target delivery to those cells which possess receptors for such hormones. Chemokines and cytokines can similarly be employed as targeting signals to target delivery of the complex to their target cells. A variety of technologies have been developed to identify genes that are preferentially expressed in certain cells or cell states and one of skill in the art can employ such technology to identify targeting signals which are preferentially or uniquely expressed on the target tissue of interest.

In preferred embodiments, the targeting signal or domain targets the CTPS1 inhibitor or a delivery vehicle carrying the inhibitor to the cells of the vasculature, preferably smooth muscle cells of the vasculature, more preferably media layer smooth muscle cells.

Compositions and methods for targeting the vasculature are known in the art. For example, compositions and delivery vehicles can be targeted to VSMC surface epitopes, for example, Tissue Factor (TF). Also referred to as also platelet tissue factor, factor III, thromboplastin, or CD142, TF is a protein present in subendothelial tissue and leukocytes necessary for the initiation of thrombin formation from the zymogen prothrombin. TF protein is typically described as having three domains: an extracellular domain, a transmembrane domain, and cytoplasmic domain. In a preferred embodiment, the targeting signal binds to the extracellular domain of TF. For example, the targeting signal can be an antibody or antigen binding fragment thereof that binds to the extracellular domain of TF.

The extracellular domain of TF binds factor VIIa. Factor VIIa is a protein which consists of several domains. One of these domains, the carboxylated GLA domain, binds in the presence of calcium to negatively charged phospholipids. Binding of VIIa to negatively charged phospholipids greatly enhances the protein-protein binding of VIIa to TF. In some embodiments, the targeting signal includes one or more domains of Factors VIIa that bind to TF.

Compositions and methods for delivering agents to vascular smooth muscle cells (VSMCs) by targeting Tissue Factor (TF) are known in the art. See, for example, Lanza, et al., *Circulation*, 106:2842-2847 (2002) and Lanza, et al., *J. Am. Soc. Echo.*, 13:608-614 (2000), each of which is specifically incorporated by references in its entirety, which describe targeting drugs and imaging reagents, respectively, to media VSMCs using TF-targeting nanoparticles.

In another embodiment, the targeting signal binds to $\alpha_v\beta_3$ integrin, which is expressed on the surface of stretch-activated smooth muscle cells exposed along the sheared tissue planes of the arterial wall following vascular damage (Cyrus, et al., *Arteriosclerosis, Thrombosis, and Vascular Biology*, 28:820-826 (2008)). Accordingly, the signaling agent can be an antibody that binds to $\alpha_v\beta_3$-integrin, or a ligand of $\alpha_v\beta_3$-integrin, for example a protein or polypeptide including the amino acid sequence R-G-D, or a small molecule agonist or antagonist of $\alpha_v\beta_3$-integrin.

In some embodiments, the compositions or delivery vehicles are targeted to endothelial cells, sites of vascular inflammation, blood clots, thromboses, or combinations thereof. For example, vascular inflammation is discussed in Inoue, et al., JACC: *Cardiovascular Interventions*, 4(10): 1057-1066 (2011), which is specifically incorporated by reference in its entirety, and discusses various factors, proteins, cytokines, and cell types that are localized to sites of vascular inflammation and therefore can serve as targets for the targeting signals used with the compositions and delivery vehicles disclosed herein. Components of clots and thromboses may be used as suitable targets. Among these markers or targets are fibrin, gpIIb/IIIa, tissue factor/VIIA complex, activated clotting factor Xa, activated clotting factor IXa, and the fibrin condensation product, d-dimer.

In some embodiments, the targeting signal is incorporated into or linked to a delivery vehicle. For example, if the delivery vehicle is a polymeric particle, the targeting molecules can be coupled directly to the particle or to an adaptor element such as a fatty acid which is incorporated into the polymer. Ligands may be directly attached to the surface of polymeric particles via a functional chemical group (carboxylic acids, aldehydes, amines, sulfhydryls and hydroxyls) present on the surface of the particle and present on the ligand to be attached. Functionality may be introduced post-particle preparation, by direct crosslinking of particles and ligands with homo- or heterobifunctional crosslinkers. This procedure may use a suitable chemistry and a class of crosslinkers (CDT, EDAC, glutaraldehydes, etc. as discussed in more detail below) or any other crosslinker that couples ligands to the particle surface via chemical modification of the particle surface after preparation.

Ligands may also be attached to polymeric particles indirectly though adaptor elements which interact with the polymeric particle. Adaptor elements may be attached to polymeric particles in at least two ways. The first is during the preparation of the micro- and nanoparticles, for example, by incorporation of stabilizers with functional chemical groups during emulsion preparation of microparticles. For example, adaptor elements, such as fatty acids, hydrophobic or amphiphilic peptides and polypeptides can be inserted into the particles during emulsion preparation. In a second embodiment, adaptor elements may be amphiphilic molecules such as fatty acids or lipids which may be passively adsorbed and adhered to the particle surface, thereby introducing functional end groups for tethering to ligands. Adaptor elements may associate with micro- and nanoparticles through a variety of interactions including, but not limited to, hydrophobic interactions, electrostatic interactions and covalent coupling.

In some embodiments, the targeting signal is or includes a protein transduction domain, also known as cell penetrating peptides (CPPS). PTDs are known in the art, and include but are not limited to small regions of proteins that are able to cross a cell membrane in a receptor-independent mechanism (Kabouridis, P., *Trends in Biotechnology* (11):498-503 (2003)). The two most commonly employed PTDs are derived from TAT (Frankel and Pabo, *Cell*, December 23; 55(6):1189-93 (1988)) protein of HIV and Antennapedia transcription factor from Drosophila, whose PTD is known as Penetratin (Derossi et al., *J Biol Chem.* 269(14):10444-50 (1994)).

The Antennapedia homeodomain is 68 amino acid residues long and contains four alpha helices. Penetratin is an active domain of this protein which consists of a 16 amino acid sequence derived from the third helix of Antennapedia (SEQ ID NO:3). TAT protein (SEQ ID NO:4) consists of 86 amino acids and is involved in the replication of HIV-1. The TAT PTD consists of an 11 amino acid sequence domain (residues 47 to 57; YGRKKRRQRRR (SEQ ID NO:5) of the parent protein that appears to be critical for uptake. Additionally, the basic domain Tat(49-57) or RKKRRQRRR (SEQ ID NO:6) has been shown to be a PTD.

Several modifications to TAT, including substitutions of Glutamine to Alanine, i.e., Q→A, have demonstrated an increase in cellular uptake anywhere from 90% to up to 33 fold in mammalian cells. (Ho et al., *Cancer Res.* 61(2):474-7 (2001)) The most efficient uptake of modified proteins was revealed by mutagenesis experiments of TAT-PTD, showing that an 11 arginine stretch was several orders of magnitude more efficient as an intercellular delivery vehicle. Thus, some embodiments include PTDs that are cationic or amphipathic. Additionally exemplary PTDs include but are not limited to poly-Arg—RRRRRRR (SEQ ID NO:7); PTD-5—RRQRRTSKLMKR (SEQ ID NO:8); Transportan GWTLNSAGYLLGKINLKALAALAKKIL (SEQ ID NO:9); KALA—WEAKLAKALAKALAKHLAKA-LAKALKCEA (SEQ ID NO:10); and RQIKIWFQNRRM-KWKK (SEQ ID NO:11).

C. Delivery Vehicles

The CTPS1 inhibitors can be administered and taken up into the cells of a subject with or without the aid of a delivery vehicle. Appropriate delivery vehicles for the disclosed inhibitors are known in the art and can be selected to suit the particular inhibitor. For example, if the CTPS1 inhibitor is a nucleic acid or vector, the delivery vehicle can be a viral vector, for example a commercially available preparation, such as an adenovirus vector (Quantum Biotechnologies, Inc. (Laval, Quebec, Canada). The viral vector delivery can be via a viral system, such as a retroviral vector system which can package a recombinant retroviral genome (see e.g., Pastan et al., (1988)*Proc. Natl. Acad. Sci. U.S.A.* 85:4486; Miller et al., (1986) Mol. Cell. Biol. 6:2895). The recombinant retrovirus can then be used to infect and thereby deliver to the infected cells nucleic acid encoding the CTPS1 inhibitor. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948 (1994)), adeno-associated viral (AAV) vectors (Goodman et al., *Blood* 84:1492-1500 (1994)), lentiviral vectors (Naidini et al., *Science* 272:263-267 (1996)), pseudotyped retroviral vectors (Agrawal et al., *Exper. Hematol.* 24:738-747 (1996)).

Physical transduction techniques can also be used, such as liposome delivery and receptor-mediated and other endocytosis mechanisms (see, for example, Schwartzenberger et al., *Blood* 87:472-478 (1996)). For example in some embodiments, the CTPS1 inhibitor is delivered via a liposome. Commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art are well known. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.). This disclosed compositions and methods can be used in conjunction with any of these or other commonly used gene transfer methods.

In some embodiments, the delivery vehicle is incorporated into or encapsulated by a nanoparticle, microparticle, micelle, synthetic lipoprotein particle, or carbon nanotube. For example, the compositions can be incorporated into a vehicle such as polymeric microparticles which provide controlled release of the CTPS1 inhibitor. In some embodiments, release of the drug(s) is controlled by diffusion of the CTPS1 inhibitor out of the microparticles and/or degradation of the polymeric particles by hydrolysis and/or enzymatic degradation. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof.

The CTPS1 inhibitor can be incorporated into prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, waxlike substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes.

Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

Micro and nanoparticles designed to deliver cargo such as a drugs and imaging reagents to the vasculature, to vascular smooth muscle cells, or sites or clots or thrombosis are known art. See, for example, Wickline, et al., *Arteriosclerosis, Thrombosis, and Vascular Biology,* 26:435-441 (2006), published online (December 2005), and U.S. Published Application Nos. 2002/0168320, 2003/0086867, 2003/0129136, 2004/0058951, 2004/0115192, 2006/0147380, 2006/0239919, 2007/0140965, 2007/0202040, 2007/0258908, 2008/0175792, 2008/0247943, and 2013/0064765, each of which are specifically incorporated by reference herein in its entirety.

For example, perfluorocarbon nanoparticles, previously considered as artificial blood substitutes, have been developed into a platform technology for molecular imaging and targeted drug delivery, i.e., a so-called "theranostic" technology. These lipid-encapsulated particles, which are nominally 250 nm in diameter, can be administered intravenously and are typically constrained by size to the intact vasculature.

Preferred vehicles for delivery of nucleoside analogs, including, but not limited to, polymer-based nanoparticles and polyplex nanogel formulations are also known in the art. See, for example, Hillaireau, et al., *J. Nanosci. Nanotechnol.,* 6(9-10):2608-17 (2006), Vinogradov, et al, *J. Control Release,* 107(1): 143-57 (2005), and Vinogradov, *Expert Opin Drug Deliv.* 4(1): 5-17 (2007), each of which is specifically incorporated by reference in its entirety.

D. Formulations

Pharmaceutical compositions including one or more CTPS1 inhibitors are also disclosed.

1. Pharmaceutical Compositions

Pharmaceutical compositions including a CTPS1 inhibitor, and optionally a targeting moiety, a delivery vehicle, or a combination thereof are provided. Pharmaceutical compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In certain embodiments, the compositions are administered locally, for example by injection directly into a site to be treated. In some embodiments, the compositions are injected, topically applied, or otherwise administered directly into the vasculature onto vascular tissue at or adjacent to a site of injury, surgery, or implantation. For example, in embodiments, the compositions are topically applied to vascular tissue that is exposed, during a surgical or implantation, or transplantation procedure. Typically, local administration causes an increased localized concentration of the compositions which is greater than that which can be achieved by systemic administration.

a. Formulations for Parenteral Administration

Compositions including those containing a CTPS1 inhibitor, and optionally a targeting moiety, a delivery vehicle, or a combination thereof are administered in an aqueous solution, by parenteral injection. The formulation may also be in the form of a suspension or emulsion. In general, pharmaceutical compositions are provided including effective amounts of the CTPS1 inhibitor and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

b. Oral Formulations

Oral formulations may be in the form of chewing gum, gel strips, tablets or lozenges. Encapsulating substances for the preparation of enteric-coated oral formulations include cellulose acetate phthalate, polyvinyl acetate phthalate, hydroxypropyl methylcellulose phthalate and methacrylic acid ester copolymers. Solid oral formulations such as capsules or tablets are preferred. Elixirs and syrups also are well known oral formulations. The components of aerosol formulations include solubilized active ingredients, antioxidants, solvent blends and propellants for solution formulations, and micronized and suspended active ingredients, dispersing agents and propellants for suspension formulations. The oral, aerosol and nasal formulations of the invention can be distinguished from injectable preparations of the prior art because such formulations may be nonaseptic, whereas injectable preparations must be aseptic.

c. Formulations for Topical Administration

The CTPS1 inhibitor, and optionally a targeting moiety, a delivery vehicle, or a combination thereof can be applied topically. Topical administration can include application to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Co.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations can include penetration enhancers.

2. Effective Amounts

In some in vivo approaches, the compositions are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect.

The amount of composition administered to the subject is typically effective to reduce or inhibit proliferation of smooth muscle cells, particularly, vascular smooth muscle cells. In some embodiments, the amount is effective to reduce or inhibit proliferation of smooth muscle cells to a greater extent than reducing or inhibiting proliferation of endothelial cells. In some embodiments, the amount is effective to reduce or inhibit proliferation of smooth muscle cells without substantially reducing or inhibiting proliferation of endothelial cells.

In some embodiments the amount is effective to reduce or inhibit proliferation of both smooth muscle cells and endothelial cells in the absence of cytidine. As discussed in more detail below, cytidine can be co-administered to the subject with the CPTS1 inhibitor to induce the CTP synthesis salvage pathway and rescue proliferation in the endothelial cells. Accordingly, when co-administered with cytidine, proliferation of smooth muscles cells is inhibited, but endothelial cells can continue to proliferate even at high doses of CPTS1 inhibitor. Cytidine is typically administered in such a way that it can contact the endothelial cells. For example, cytidine can be injected are infused into the blood stream.

The composition can also be administered in an amount effective to reduce or inhibit migration, particularly PDGF-BB-induced SMC migration, of smooth muscle cells.

In the most preferred embodiments, the composition is administered in an amount to prevent, reduce, or inhibit neointima. For example, the amount can be effective to reduce proliferation, migration, or a combination thereof of smooth muscle cells from the media layer into the intima. The amount can be effective to prevent, reduce, or inhibit the rise or appearance of fused intima and media. The amount can be effective to reduce proliferation, migration, or a combination thereof of intima smooth muscle cells.

Preferably, the composition is administered in an amount that is effective to prevent, reduce, or inhibit neointima without preventing re-endothelialization at the site of a vascular injury. In some embodiments, the compositions promote re-endothelialization after vascular injury.

The precise dosage will vary according to a variety of factors such as subject-dependent variables (e.g., age, immune system health, etc.), the disease, and the treatment being effected. As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower.

Preferred dosages for some of the CTPS1 inhibitors disclosed herein are provided above or known in the art. It is believed, however, that the dosage for reducing neointima formation can be lower than the dosages that are typically administered in the art for treatment of infections or cancer.

III. Devices and Grafts

The compositions disclosed herein can be coated onto or incorporated into medical devices, or to pre-treat implantable vascular grafts ex vivo.

A. Devices

In some embodiments, a composition including one or more CTPS1 inhibitors is coated onto, or incorporate into, a medical device to reduce or inhibit neointima formation in a subject. The device can be a device that is inserted into the subject transiently, or a device that is implanted permanently. In some embodiments, the device is surgical device.

Examples of medical devices include, but are not limited to, needles, cannulas, catheters, shunts, balloons, and implants such as stents and valves.

In some embodiments, the CTPS1 inhibitor or pharmaceutical composition can be formulated to permit its incorporation onto the medical device, which can apply the inhibitor directly to the site to prevent or treat conditions such restenosis or another vascular proliferation disorder.

In some embodiments the CTPS1 inhibitor or pharmaceutical composition thereof is formulated by including it within a coating on the medical device. There are various coatings that can be utilized such as, for example, polymer coatings that can release the inhibitor over a prescribed time period. The inhibitor, or a pharmaceutical composition thereof, can be embedded directly within the medical device. In some embodiments, the CTPS1 inhibitor is coated onto or within the device in a delivery vehicle such as a microparticle or liposome that facilitates its release and delivery. In some embodiments, the CTPS1 inhibitor is miscible in the coating.

In some embodiments, the medical device is a vascular implant such as a stent. Stents are utilized in medicine to prevent or eliminate vascular restrictions. The implants may be inserted into a restricted vessel whereby the restricted vessel is widened. The experience with such vascular implants indicates that excessive growth of the adjacent cells results again in a restriction of the vessel particularly at the ends of the implants which results in reduced effectiveness of the implants. If a vascular implant is inserted into a human artery for the elimination of an arteriosclerotic stenosis, intimahyperplasia can occur within a year at the ends of the vascular implant and results in renewed stenosis.

Accordingly, in some embodiments, the stents are coated or loaded with a composition including a CPTS1 inhibitor and optionally a targeting signal, a delivery vehicle, or a combination thereof. Many stents are commercially available or otherwise know in the art.

Stents can be formed, i.e., etched or cut, from a thin tube of suitable material, or from a thin plate of suitable material and rolled into a tube. Suitable materials for the stent include but are not limited to stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, aluminum, vanadium, and carbon, as well as combinations, alloys, and/or laminations thereof. For example, the stent may be formed from a cobalt alloy, such as L605 or MP35N®, Nitinol (nickel-titanium shape memory alloy), ABI (palladium-silver alloy), Elgiloy® (cobalt-chromium-nickel alloy), etc. It is also contemplated that the stent may be formed from two or more materials that are laminated together, such as tantalum that is laminated with MP35N®. The stents may also be formed from wires having concentric layers of different metals, alloys, or other materials. Embodiments of the stent may also be formed from hollow tubes, or tubes that have been filled with other materials. The aforementioned materials and laminations are intended to be examples and are not intended to be limiting in any way.

Stents can also be composed of and/or coated with one or more degradable materials. For example, absorbable materials to make stents and stent coatings are described in U.S. Pat. Nos. 5,059,211 and 5,306,286; U.S. Pat. No. 5,935,506 describes a method to manufacture an absorbable stent from poly-3-hydroxybutyrate (P3HB); U.S. Pat. No. 6,045,568 describes absorbable stents manufactured from knitting yarns of polyactic acid (PLA), polyglycolic acid (PGA), polyglactin (P(GA-co-LA)), polydioxanone (PDS), polyglyconate (a block co-polymer of glycolic acid and trimethylene carbonate, P(GA-co-TMC)), and a copolymer of glycolic acid or lactic acid with ε-caprolactone (P(GA-co-CL) or P(LA-co-CL)); and Laaksovirta et al., describes a self-expandable, biodegradable, self-reinforced stent from P(GA-co-LA) for use in urethral applications (*J Urol.* 2003 August; 170(2 Pt 1):468-71). The use of polyanhydride and polyorthoester polymers to manufacture absorbable stents is described by Tanguay, J. F. et al., *Cardiology Clinics,* 12:699-713 (1994). WO 98/51812 to Williams et al. discloses methods to remove pyrogens from polyhydroxyalkanoates, and the fabrication of stents with these depyrogenated materials and WO 99/32536 to Martin et al. and WO 00/56376 to Williams et al. disclose methods to prepare polyhydroxyalkanoates with controlled degradation rates, and the fabrication of stents with these materials. Van der Giessen et al. (Marked Inflammatory Sequelae to Implantation of Biodegradable and Nonbiodegradable Polymers in Porcine Coronary Arteries, Circulation, 94:1690-1697 (1996)) evaluated coatings of a copolymer of glycolic acid and lactic acid (P(GA-co-LA)), polycaprolactone (PCL), poly-3-hydroxybutyrate-co-3-hydroxyvalerate (P(3HB-co- 3HV), a polyorthoester, and a polyethyleneoxide-polybutylene terephthalate on metal stents, and reported that the coatings induced marked inflammatory reactions within the coronary artery. Other bioresorbable stent materials include iron, magnesium, zinc, and their alloys.

In some embodiments the stent is composed of two or more bioabsorbable polymers. In some embodiments, the stent is coated with one or more bioabsorbable polymers. The stent can be composed of and coated with the same or different polymers. Method of making and coating absorbable stents are described in U.S. Pat. No. 7,618,448. Stents can include two or more coatings, for example, a base coat and one or more top coats composed of the same or different polymers.

In some embodiments, the stent is a drug-eluting stent. Various drug eluting stents that simultaneously deliver a therapeutic substance to the treatment site while providing artificial radial support to the wall tissue are known in the art. Endoluminal devices including stents are sometimes coated on their outer surfaces with a substance such as a drug releasing agent, growth factor, or the like. Stents have also been developed having a hollow tubular structure with holes or ports cut through the sidewall to allow drug elution from a central lumen. Although the hollow nature of the stent allows the central lumen to be loaded with a drug solution that is delivered via the ports or holes in the sidewall of the stent, the hollow tubular structure may not have suitable mechanical strength to provide adequate scaffolding in the vessel.

In some embodiments, the devices are also coated or impregnated with a CTPS1 inhibitor and one or more additional therapeutic agents, including, but not limited to, antiplatelet agents, anticoagulant agents, anti-inflammatory agents antimicrobial agents, antimetabolic agents, additional anti-neointima agents, additional antiproliferative agents, immunomodulators, antiproliferative agents, agents that affect migration and extracellular matrix production, agents that affect platelet deposition or formation of thrombosis, and agents that promote vascular healing and re-endothelialization, such as those and others described in Tanguay et al. *Cardiology Clinics,* 12:699-713 (1994), J. E. Sousa, et al., *Circulation,* 107 (2003) 2274 (Part I), 2283 (Part II), Salu, et al., *Acta Cardiol,* 59 (2004) 51.

Examples of antithrombin agents include, but are not limited to, Heparin (including low molecular heparin), R-Hirudin, Hirulog, Argatroban, Efegatran, Tick anticoagulant peptide, and PPACK.

Examples of antiproliferative agents include, but are not limited to, Paclitaxel (Taxol), QP-2 Vincristin, Methotrexat, Angiopeptin, Mitomycin, BCP 678, Antisense c-myc, ABT 578, Actinomycin-D, RestenASE, 1-Chlor-deoxyadenosin, PCNA Ribozym, and Celecoxib.

Examples of anti-restenosis agents include, but are not limited to, immunomodulators such as Sirolimus (Rapamycin), Tacrolimus, Biorest, Mizoribin, Cyclosporin, Interferon-γ 1b, Leflunomid, Tranilast, Corticosteroide, Mycophenolic acid and Biphosphonate.

Examples of anti-migratory agents and extracellular matrix modulators include, but are not limited to Halofuginone, Propyl-hydroxylase-Inhibitors, C-Proteinase-Inhibitors, MMP-Inhibitors, Batimastat, Probucol.

Examples of antiplatelet agents include, but are not limited to, heparin.

Examples of wound healing agents and endothelialization promoters include vascular epithelial growth factor ("VEGF"), 17β-Estradiol, Tkase-Inhibitors, BCP 671, Statins, nitric oxide ("NO")-Donors, and endothelial progenitor cell ("EPC")-antibodies.

Besides coronary applications, drugs and active agents may be incorporated into the stent or stent coating for other indications. For example, in urological applications, antibiotic agents may be incorporated into the stent or stent coating for the prevention of infection. In gastroenterological and urological applications, active agents may be incorporated into the stent or stent coating for the local treatment of carcinoma.

It may also be advantageous to incorporate in or on the stent a contrast agent, radiopaque markers, or other additives to allow the stent to be imaged in vivo for tracking, positioning, and other purposes. Such additives could be added to the absorbable composition used to make the stent or stent coating, or absorbed into, melted onto, or sprayed onto the surface of part or all of the stent. Preferred additives for this purpose include silver, iodine and iodine labeled compounds, barium sulfate, gadolinium oxide, bismuth derivatives, zirconium dioxide, cadmium, tungsten, gold tantalum, bismuth, platinum, iridium, and rhodium. These additives may be, but are not limited to, mircro- or nano-sized particles or nano particles. Radio-opacity may be determined by fluoroscopy or by x-ray analysis.

A CTPS1 inhibitor and one or more additional agents can be incorporated into the stent, either by loading the agent(s) into the absorbable material prior to processing, and/or coating the surface of the stent with the agent(s). The rate of release of agent may be controlled by a number of methods including varying the following the ratio of the absorbable material to the agent, the molecular weight of the absorbable material, the composition of the agent, the composition of the absorbable polymer, the coating thickness, the number of coating layers and their relative thicknesses, and/or the agent concentration. Top coats of polymers and other materials, including absorbable polymers, may also be applied to active agent coatings to control the rate of release. For example, P4HB can be applied as a top coat on a metallic stent coated with P4HB including an active agent to retard the release of the active agent.

Exemplary stents that can be used with the compositions and methods disclosed herein include, but are not limited to, those described in U.S. Pat. Nos. 5,891,108, 6,918,929, 6,923,828, 6,945,992, 6,986,785, 7,060,090, 7,144,419, 7,163,555, 7,323,008, 7,651,527, 7,655,034, 7,678,141, 7,744,645, 7,942,917, 8,001,925, 8,001,925, 8,034,099, 8,048,149, 8,066,760, 8,100,960, 8,157,855, 8,172,893, 8,182,524, 8,187,284, 8,187,322, 8,197,528, 8,206,432, 8,221,490, 8,231,669, 8,236,044, 8,252,048, 8,252,065, 8,257,425, 8,257,431, 8,292,945, 8,298,278, 8,298,280, 8,348,991, 8,348,992, 8,348,993, 8,353,952, 8,359,998, 8,361,140, 8,372,134, 8,372,138, 8,377,112, 8,388,676, 8,398,695, 8,414,637, 8,414,639, and 8,414,656.

B. Grafts

The compositions can also be used to pre-treat vascular grafts ex vivo prior to implantation in a subject. The compositions including one or more CTPS1 inhibitor and optionally a targeting single, a delivery vehicle or a combination thereof can be applied to the tissue by methods to insure that they adhere and are distributed throughout the tissue in optimal locations for drug treatment. In some embodiments, the CTPS1 is delivered using a nanoparticle or microparticle that is designed they adhere to the regions of interest, to carry sufficient drug load to provide local treatment for prolonged periods, to release the drug load at the proper rate, to penetrate into tissue to an optimal extent, or a combination thereof. The surgeon can then apply a long-term, local drug regimen at the same time the tissue or organ is placed in the patient.

For example, the amount of inhibitor present on the graft tissue and the penetration of the inhibitor throughout the tissue can be adjusted, by changing the formulation or delivery vehicle. In this way the amount of drug locally release at the site of implantation can be carefully controlled. Typically, the CTPS1 inhibitor, or a delivery vehicle carrying the inhibitor is contacted with the graft material ex vivo. The contacting can occur in the absence or presence of mild agitation, or other methods known in the art to insure that inhibitor attaches to or penetrates the graft tissue. Agitation may be accomplished for example, by incubation on an orbital shaker, or by vertical rotation, such as by incubation in a vertical carousel of a hybridization oven. The incubation protocol can be varied to affect the positioning of the particles on the graft. The amount and localization of attachment of delivery vehicles such as particles to the graft can also be varied by varying the type and density of attachment and targeting ligands, such as those described above, presented on the vehicle. Compositions and methods for delivering drugs to vascular grafts ex vivo are discussed in U.S. Published Application Nos. 2006/0002971, 2010/0151436, and U.S. Pat. No. 7,534,448.

The compositions and methods can be used to locally deliver anti-restenotic agents to grafts with, or without the requirement for further invasive procedures, such as placement of a stent. Examples of vascular grafts, include, but not limited to, bypass grafts and arteriovenous grafts. The grafts can be autologous, for example, saphenous vein or radial artery; preserved autologous, for example cryopreserved vein; allogeneic; xenogenic; or synthetic, for example, woven polyester, polyurethane (LYCRA®), polytetraflouroethylene (PTFE), GORE-TEX®, or polyethylene terephthalate (DACRON®). For example, arterial homograft using internal mammary, radial or hypogastric arteries are examples of useful and durable vascular conduits.

Exemplary graft procedures are discussed below.

1. Bypass Graft

A common form of bypass surgery involves resecting the saphenous vein from the leg for autotransplantation to the coronary artery. In a significant number of cases these grafts fail, largely due to restenosis caused by neointimal hyperplasia. The methods described herein can be used to deliver one or more CTPS1 inhibitors locally and in a controlled fashion, to the autologous graft. The application of the inhibitor can be done during surgery. After resection of the saphenous vein the tissue can be (and is often for hours) suspended in saline during chest opening and preparation for graft implantation. Compositions including one or more CTPS1 inhibitors and optional a targeting signal, delivery vehicle or combination thereof can be incubated with the saphenous vein during this time period.

2. Arteriovenous Graft

End stage renal disease is increasing in the United States. Morbidity of hemodialysis access remains a major quality of life issue for patients; it also represents a significant cost to society. A native arteriovenous fistula (AVF) remains the conduit of choice to provide access for hemodialysis and provides superior results when compared with other options such as a prosthetic AVG. Unfortunately each individual is limited in the number of native AVF that can be created due to the limited number of suitable sites and vessels. Access sites are limited as patients with end stage renal disease usually have severe comorbidity, requiring extensive venipuncture for diagnosis and therapy for life. In patients who have exhausted all options for primary AVF, new access sites must use AV grafts; these grafts are susceptible to restenosis by neointimal hyperplasia limiting their effectiveness. Incubation of a composition including one or more CTPS1 inhibitors, and optionally including a targeting signal, a delivery vehicle, or a combination thereof onto the graft can be done at the time of surgery.

IV. Methods of Reducing or Preventing Neointima Formation

Methods of preventing, reducing, or inhibiting neointima formation are disclosed. The methods can include administering a subject an effective amount of a composition including a CTPS1 inhibitor to prevent, reduce, or inhibit neointima formation in the subject; pretreating a medical device or vascular graft with an effective amount a composition including a CTPS1 inhibitor to prevent, reduce, or inhibit neointima formation following insertion or implantation of the device or graft into the subject; or a combination thereof.

The methods typically reduce or inhibit proliferation of smooth muscle cells, particularly, vascular smooth muscle cells, compared to a control. In some embodiments, the methods reduce or inhibit proliferation of smooth muscle cells to a greater extent than endothelial cells, or without reducing or inhibiting proliferation of endothelial cells.

Proliferating smooth muscle cells secrete factors that can reduce or inhibit the proliferation of endothelial cells which can reduce or delay re-endothelialization. Therefore, in some embodiments, the methods do not reduce, or even enhance or promote re-endothelialization. The methods can reduce proliferation, migration, or a combination thereof of smooth muscle cells from the media layer into the intima. In the most preferred embodiments, the methods prevent, reduce, or inhibit the rise or appearance of fused intima and media.

Suitable controls are known in the art, and include, for example, untreated cells, or an untreated subject. In some embodiments, the control is untreated tissue for the subject that is treated, or from an untreated subject. Preferably the cells or tissue of the control are the derived from the same tissue as the treated cells or tissue. In some embodiments, an untreated control subject suffers from the same condition as the treated subject, for example, injured or enthothelial cell-denuded vasculature.

A. Methods of Treatment

Inhibition of CTPS1 can be a pathway that can be therapeutically targeted through either local or systemic delivery. In some embodiments, the compositions are administered systemically and targeted to the vasculature using a targeting signal such as those discussed above. In some embodiments, the compositions are administered directly to the local site of vascular injury.

It is believed that CTPS1 is an early target in the restenosis process and as such, early pharmacological intervention can preclude chronic therapy and any potentially adverse side effects associated with chronic therapy. For example, the compositions disclosed herein can reduce or prevent neointima formation, but allow re-endothelialization to occur. In some embodiments, the therapy can be discontinued once re-endothelialization has occurred.

In some embodiments, the compositions are coated onto or incorporated into devices or grafts as discussed above.

B. Combination Therapies

The compositions, devices, and grafts disclosed herein can be used in combination with one or more additional therapeutic agents. The term "combination" or "combined" is used to refer to either concomitant, simultaneous, or sequential administration of two or more agents. Therefore, the combinations can be administered either concomitantly (e.g., as an admixture), separately but simultaneously (e.g., via separate intravenous lines into the same subject), or sequentially (e.g., one of the compounds or agents is given first followed by the second). The additional therapeutic agents can be administered locally or systemically to the subject, or coated or incorporated onto, or into a device or graft.

The additional therapeutic agents are other anti-neointima agents, chemotherapeutic agents, antibodies, antibiotics, antivirals, steroidal and non-steroidal anti-inflammatories, conventional immunotherapeutic agents, immunosuppressants, cytokines, chemokines and/or growth factors. For example, in some embodiments, the CTPS1 inhibitor is combined with other agents such as, including, but not limited to, Paclitaxel, Taxotere, other taxoid compounds, other anti-proliferative agents such as Methotrexate, anthracyclines such as doxorubicin, immunosuppressive agents such as Everolimus and Serolimus, and other rapamycin and rapamycin derivatives.

The additional therapeutic agents can be other anti-proliferatives or anti-migrations agents designed for treating or preventing neointima formation or restenosis. For example, in some embodiments the additional therapeutic agent is N-3,4-trihydroxybenzamide or a pharmaceutically acceptable salt or ester thereof, didox, imidate, or hydroxyurea as described in U.S. Pat. No. 8,029,815.

As discussed in the Examples below, cytidine can be used to induce the CTP synthesis salvage pathway and rescue proliferation in the endothelial cells when used in combination with a high dose of CTPS1 inhibitor. Therefore, in some embodiments, a combination therapy includes co-administration of cytidine or a cytidine analog such as those disclosed in WO 2009/058394. In a preferred embodiment, the cytidine or cytidine analog is administered into the subject's blood stream (e.g., by injection or infusion) where it will contact the luminal surface of the endothelial cells.

C. Diseases to Be Treated

The disclosed CTSP1 inhibitors have a wide variety of uses, for example, they can be used to treat or prevent restenosis or other vascular proliferative disorders following injury or various surgical procedures. Vascular trauma, such as the trauma associated with percutaneous transluminal coronary angioplasty (PTCA), typically involves a cascade of molecular and cellular events occurring within the vessel wall involving the release of a variety of vasoactive, thrombogenic, and mitogenic factors (Bauters and Isner, *Prog Cardiovasc Dis* 40:107-116 (1997); Libby and Tanaka, *Prog Cardiovasc Dis* 40:97-106 (1997); Goldschmidt-Clermont and Moldovan, *Gene Expr* 7:255-260 (1999)). Within this cascade, several mechanisms contribute to restenosis including elastic recoil, thrombosis, smooth muscle cell migration/proliferation and matrix formation. The result of these vascular events is intimal hyperplasia, whereby vascular smooth muscle cells (VSMC's) migrate from the media to the intima, proliferate, and consequently form the neointima. During this proliferative response, SMCs undergo a phenotypic modulation from a contractile to a synthetic phenotype (differentiation) (Epstein et al., *Circulation* 84:778-787 (1991); Noda-Heiny and Sobel, *Am J Physiol* 268:C1195-1201 (1995); Ueda et al., *Coron Artery Dis* 6:71-81 (1995); Farb, et al., *Circulation* 105:2974-2980 (2002); Indolfi, et al., *Trends Cardiovasc Med* 13:142-148 (2003)).

Accordingly, the disclosed compositions, devices, or grafts can be administered to a subject to reduce or inhibit smooth muscle cell proliferation, migration, and a combination thereof in an amount effective to reduce or inhibit neointima formation and thereby treat or prevent restenosis and other vascular proliferation disorders in the subject. A subject can have restenosis or other vascular proliferation disorders, or be identified as being at risk for restenosis or other vascular proliferation disorders, for example subjects who have undergone, are undergoing, or will undergo a vascular trauma, angioplasty, surgery, or transplantation arteriopathy, etc.

1. Vascular Trauma

In some embodiments, the subject has undergone, is undergoing, or will undergo a vascular trauma. Vascular trauma include those associated with medical interventions, such as surgery or angioplasty, also well as both blunt and penetrating injuries including, but not limited to, lacerations, puncture wounds, crush injuries, gunshot wounds, knife wounds, occupational injuries, falls, and motor vehicle accidents.

2. Surgery

In some embodiments, the subject has undergone, is undergoing, or will undergo a surgery. Surgeries can include invasive, a minimally invasive, or percutaneous surgery. For example, in some embodiments the subject is having surgery to treat or repair abdominal aortic aneurysm, carotid stenosis, varicose veins, peripheral arterial occlusive disease, acute limb ischemia, or aortic dissection. Common vascular surgeries include, but is not limited to, open abdominal aortic aneurysm repair, endovascular aneurysm repair (EVAR), carotid endarterectomy, carotid stenting, vein stripping, sclerotherapy and foam sclerotherapy, endovenous laser treatment, radiofrequency vein ablation, ambulatory phlebectomy, angioplasty with/out stenting, bypass surgery endarterectomy atherectomy, balloon embolectomy, thrombectomy, bypass surgery, open repair, thoracic endovascular aneurysm repair (TEVAR).

3. Angioplasty

In some embodiments, the subject has undergone, is undergoing, or will undergo angioplasty. Angioplasty is the technique of mechanically widening narrowed or obstructed arteries, such as those obstructed as a result of atherosclerosis. Generally, angioplasty includes inserting into a subject's vasculature an empty and collapsed balloon on a guide wire, known as a balloon catheter, which is passed into the narrowed locations and then inflated to a fixed size. The balloon forces expansion of the inner white blood cell/clot plaque deposits and the surrounding muscular wall, opening up the blood vessel for improved flow, and the balloon is then deflated and withdrawn. A stent may or may not be inserted at the time of ballooning to ensure the vessel remains open. Angioplasty includes peripheral angioplasty (i.e., blood vessels outside the coronary arteries, such as in the abdomen, or legs), coronary angioplasty, renal artery angioplasty, carotid angioplasty, and cerebral arteries angioplasty.

In some embodiments, the subject has undergone, is undergoing, or will undergo percutaneous transluminal coronary angioplasty (PTCA). The use of PTCA has greatly reduced the number of fatalities in patients who suffer myocardial infarction (Fischman, et al., *N Engl J Med* 331:496-501 (1994); Elezi, et al., *Circulation* 98:1875-1880 (1998); Bennett and O'Sullivan, *Pharmacol Ther* 91:149-166 (2001)). During PTCA, the artery walls are expanded by several times their original diameter in an attempt to increase lumen diameter and improve flow. Unfortunately, this technique is plagued by a high incidence of vessel renarrowing or restenosis occurring in 30-40% of patients within 6 months of the procedure (Anderson et al., *J Interv. Cardiol.*, 6:187-202 (1993); Fischman et al., *N Engl J Med*, 331:496-501 (1994); Elezi et al., *Circulation* 98:1875-1880 (1998); Bennett and O'Sullivan, *Pharmacol Ther*, 91:149-166 (2001); Heckenkamp et al., *J Cardiovasc. Surg.* (Torino), 43:349-357 (2002)).

Prevention of restenosis after successful PTCA remains one of the most challenging tasks in the treatment of obstructive coronary artery disease. Attempts to ameliorate this proliferative response involve the use coronary stents, which have significantly improved both short term and long term outcome following interventional coronary revascularization procedures. Despite a reduction in restenosis rate with stent deployment, restenosis still occurs in 15-30% of patients within 6 months (Fischman et al., *N Engl J Med*, 331:496-501 (1994); Elezi et al., *Circulation*, 98:1875-1880 (1998)). This incidence of in-stent restenosis is expected to increase as coronary stenting is becoming more frequent and is used in less ideal lesions.

4. Transplant Arteriopathy

In some embodiments, the subject has undergone, is undergoing, or will undergo a transplant. Chronic transplant arteriopathy (CTA) is a major cause of late allograft loss after heart or kidney transplantation (Taylor, et al., *J. Heart Lung Transplant.*, 24:945-955 (2005), Burke, et al., *Transplantation*, 60:1413-1417 (1995); Cornell and Colvin, *Curr. Opin. Nephrol Hypertens.*, 14:229-234 (2005)). Therefore, in some embodiments, the disclosed compositions and devices are used to reduce, inhibit, or prevent transplant arteriopathy in a transplant recipient.

5. Vascular Proliferative Disorders

In some embodiments, the subject has a vascular proliferative disorder. Examples of such disorders include, but are not limited to, vascular proliferation involved in atherosclerosis, vascular proliferation following intravascular device implantation, vascular proliferation at the site of vascular anastomosis as generally occurs following revascularization procedure or A-V shunting, vascular proliferation following carotid endarderectomy, and transplant vasculopathy.

EXAMPLES

Example 1: CTPS1 is Up-Regulated in Cultured SMCs in Vitro and Neointimal SMCs in Vivo Materials and Methods Reagents and Cell Culture Rat aortic smooth muscle cells (SMCs) were cultured by enzyme-digestion method from rat thoracic aorta as described previously (Hofer, et al., *Proc Natl Acad Sci USA.*, 98:6412-6416 (2001), Marquez, et al., Biochem Pharmacol., 41:1821-1829 (1991), (Berg, et al., *Eur. J. Biochem.*, 216: 161-167 (1993)). SMC phenotype of the cultured cells was confirmed by the expression of smooth muscle alpha-actin and SM22-alpha.

Endothelial cell C166 was purchased from ATCC and grown at 37° C. in a humidified atmosphere of 5% CO2 in DMEM (Invitrogen) supplemented with 10% FBS.

CTPS1 (sc-131474), PCNA (sc-56), CDK1 (sc-137034) and phospho-CDK1 (T161) (sc-101654) antibodies were from Santa Cruz Biotechnology (Santa Cruz, Calif.). NME1 (#3345S) and NME2 (SAB1400187) antibodies were purchased from Cell Signaling (Danvers, Mass.), and Sigma-Aldrich (St. Louis, Mo.), respectively.

Animals

Male Sprague-Dawley rats weighing 450 to 500 g and male FVB mouse (13 weeks; mean weight 24 g) were purchased from Harlan. All animals were housed under conventional conditions in the animal care facilities and received humane care in compliance with the Principles of Laboratory Animal Care formulated by the National Society for Medical Research and the Guide for the Care and Use of Laboratory Animals. Animal surgical procedures were approved by the Institutional Animal Care and Use Committee of the University of Georgia.

Rat Carotid Artery Injury Model

Rat carotid artery balloon injury was performed using 2F Fogarty arterial embolectomy balloon catheter (Baxter Edwards Healthcare) as described previously (Tulis, *Methods Mol. Med.*, 139:1-30 (2007)). 7, 14 or 60 days later, the balloon-injured arteries were perfused with saline, fixed with 4% paraformaldehyde, embedded in paraffin, and sectioned. Subsequent morphometric analyses were performed in a double-blinded manner. Ten sections that were evenly distributed in the vessel segments were collected for analysis. The sections were stained with modified hematoxylin and eosin or elastica van Gieson (VG) staining Cross-sectional images were captured with a Nikon microscope (Nikon America Inc). The circumference of the lumen, internal elastic lamina, and external elastic lamina were measured using Image-pro Plus Software. For immunohistochemistry (IHC) staining, sections were rehydrated, blocked with 5% goat serum, permeabilized with 0.01% Triton X-100 in PBS, and incubated with primary antibodies at 4° C. overnight followed by incubation with horseradish peroxidase-conjugated secondary antibody. The sections were counterstained with hematoxylin.

Statistical Analysis

Each experiment was repeated for more than three times. All values are presented as means±SEM. Comparisons of parameters between two groups were made by t test. Comparisons of parameters among more than two groups were made by one-way analysis of variance, and comparisons of different parameters between each group were made by a post hoc analysis using a Bonferroni test. P values <0.05 were considered to be statistically significant.

Results

Figure 1B:
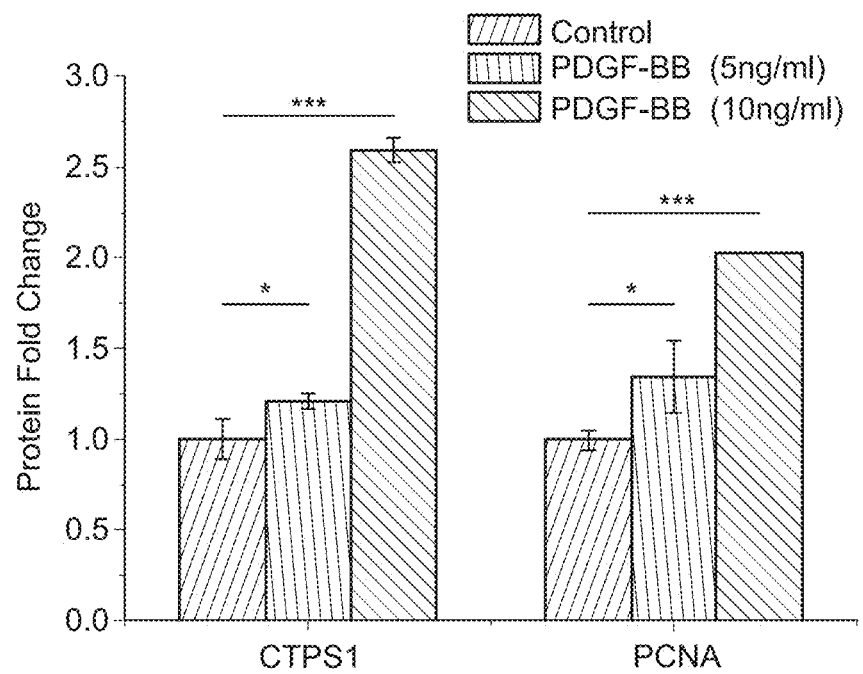
FIG. 1B is a bar graph showing quantification of CTPS1 and PCNA protein expression in control, and PDGF-BB treated (5 ng/ml, 10 ng/ml) proliferating smooth muscle cells (SMC) (shown normalized to α-tubulin).
Figure 1C:
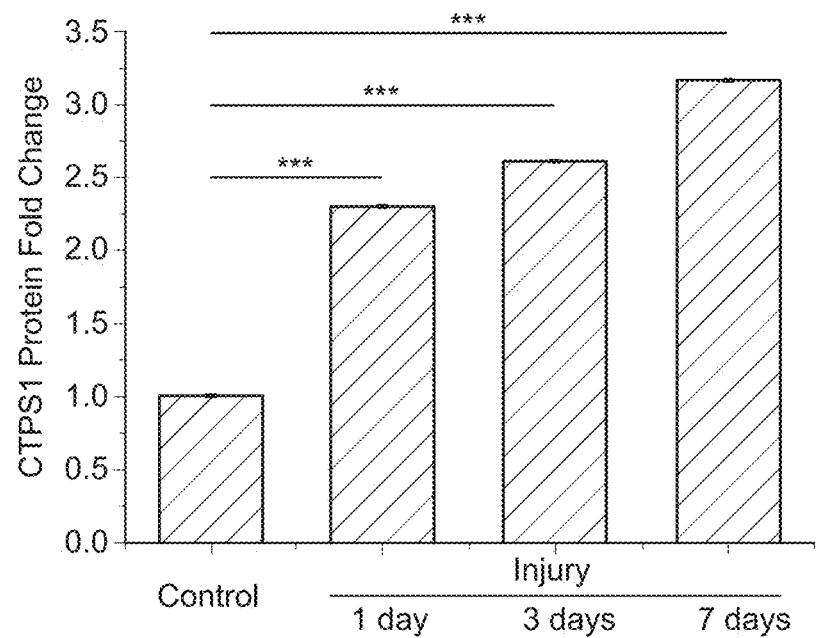
FIGS. 1C and 1D are bar graphs showing time dependent protein expression of CTPS1 (1C) and PCNA (1D) in rat carotid arteries over time (days) following injury (shown normalized to α-tubulin). $*P<0.05$, $P<0.01$, $*P<0.001$ (n=3).
Figure 1D:
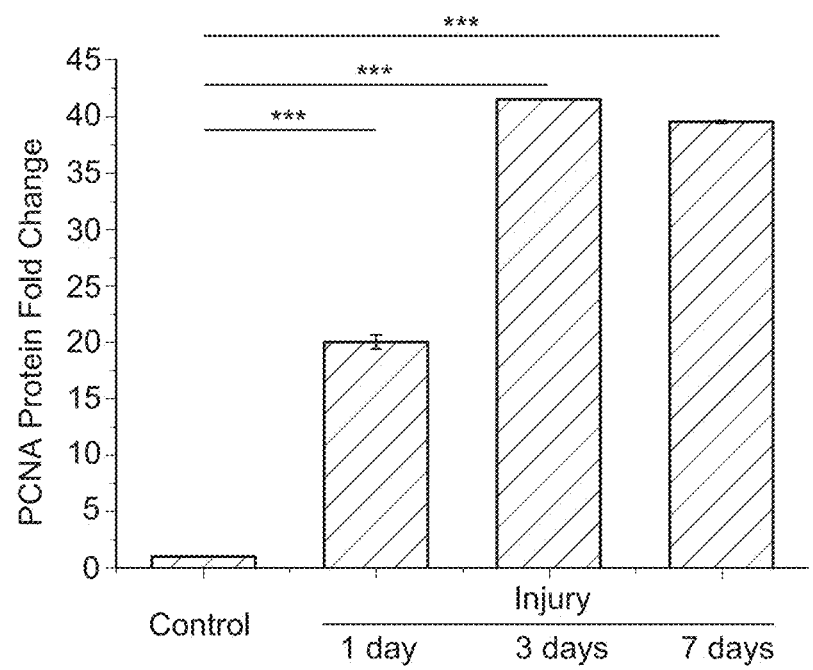
Figure 1E:
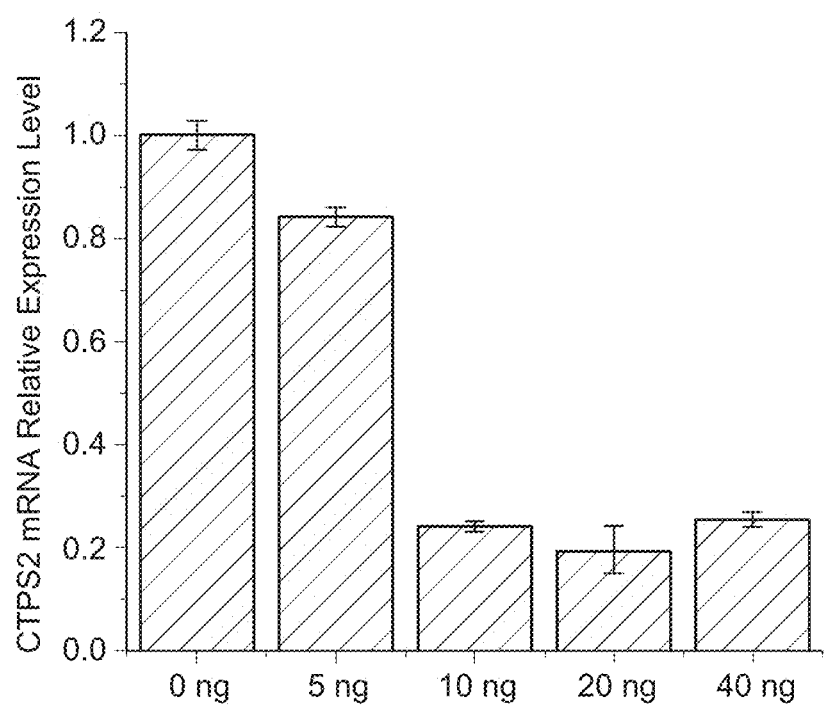
FIG. 1E is a bar graph showing the relative mRNA expression levels of CTPS2 in Rat Aortic Smooth Muscle Cells (RASMCs) treated with increasing concentrations of PDGF-BB.

It is established that CTPS is involved in the proliferation of various different cells (Hofer, et al., *Proc. Natl. Acad. Sci.*, 98:6412 (2001); de Clercq, et al., *Biochem. Pharmacol.*, 41:1821-1829 (1991); Berg, et al., *Eur. J. Biochem.*, 216: 161-167 (1993)). Although two different CTPS isotypes (CTPS1 and CTPS2) are identified in mammals, it was discovered that CTPS1, but not CTPS2, was markedly up-regulated in SMCs by PDGF-BB (FIGS. 1A-1B, 1E).

PDGF-BB is a well-known SMC mitogen that induces SMC proliferation and neointima formation following vascular injury (Arita, et al., *Circulation.*, 105:2893-2898 (2002)). PDGF-BB-mediated cell proliferation was confirmed by the up-regulation of proliferating cell nuclear antigen (PCNA) (FIG. 1B).

SMC proliferation is one of the major events in neointima formation under pathological conditions (Morishita, et al., *Proc. Natl. Acad. Sci.*, 92:5855 (1995)). CTPS1 expression was examined in rat carotid arteries undergoing vascular remodeling after balloon-injury Immunohistochemistry of neointima following vascular injury revealed that CTPS1 was expressed at a low level in the media layer SMCs, but was highly induced in neointimal SMCs. A low level of CTPS1 expression was also observed in ECs. Quantitative analysis showed that CTPS1 was significantly up-regulated as early as 1 day after vascular injury. The expression was gradually increased during neointimal formation (FIGS. 1C-1D). PCNA expression correlated with the CTPS1 expression (FIG. 1D).

Example 2: Blocking CTPS Activity Inhibits SMC Proliferation and Migration

Figure 2A:
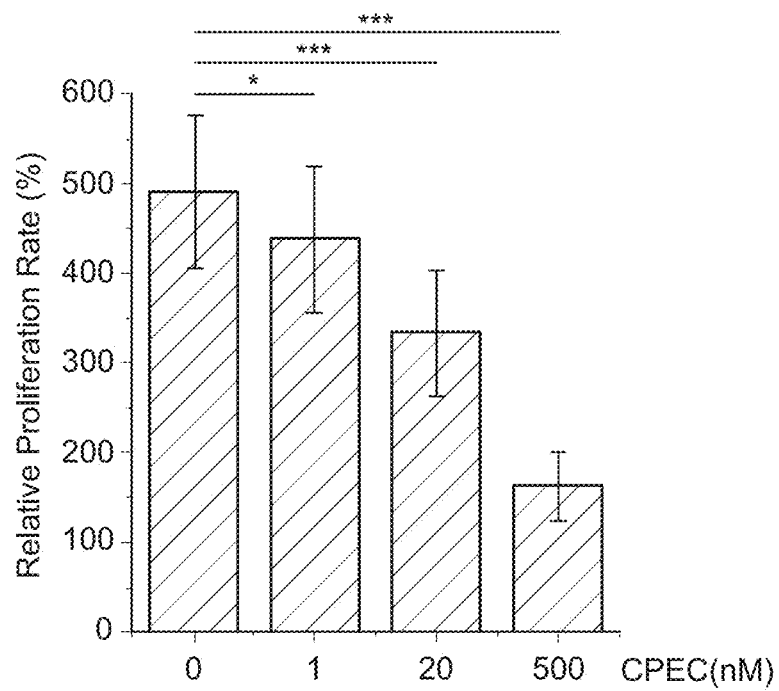
FIG. 2A is a bar graph showing the relative proliferation rate (%) of control SMC and SMC treated with 1 nM, 20 nM, or 500 nM of the CTPS inhibitor CPEC.
Figure 2B:
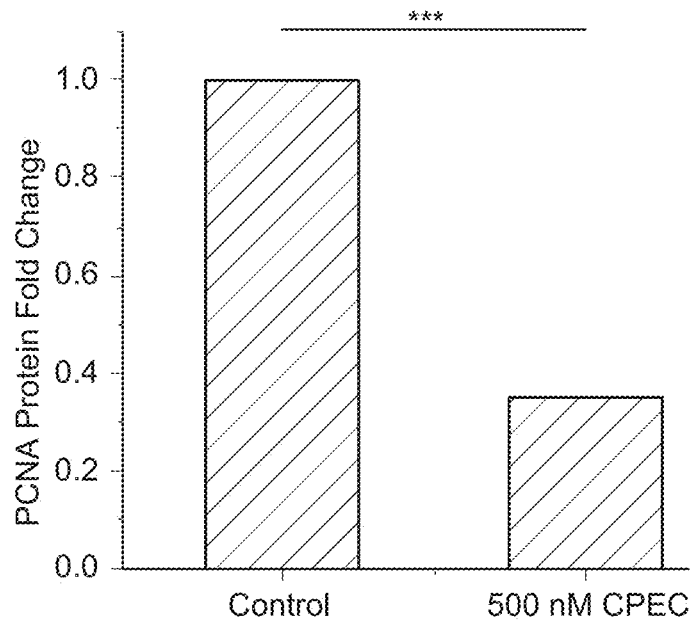
FIG. 2B is a bar graph showing PCNA protein level (fold change) in control SMC and SMC treated with 500 nM CPEC for 24 hours (normalized to α-tubulin).
Figure 2C:
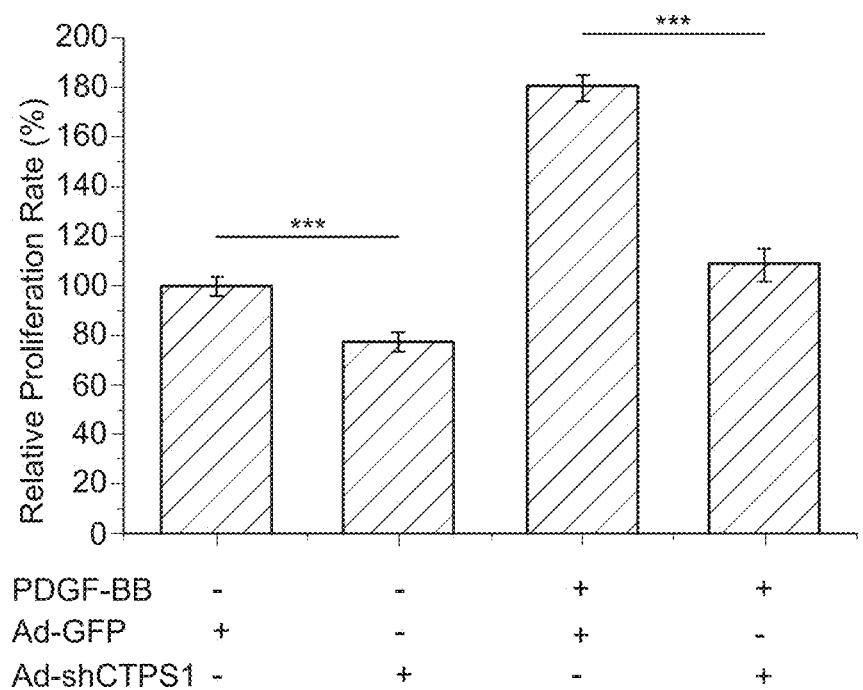
FIG. 2C is a bar graph showing the relative proliferation rate (%) of control SMC and SMC infected with or without PDGF-BB, adenoviral expressed GFP (Ad-GFP), and/or adenoviral expressed shRNA against CTPS1 (Ad-shCTPS1).
Figure 2D:
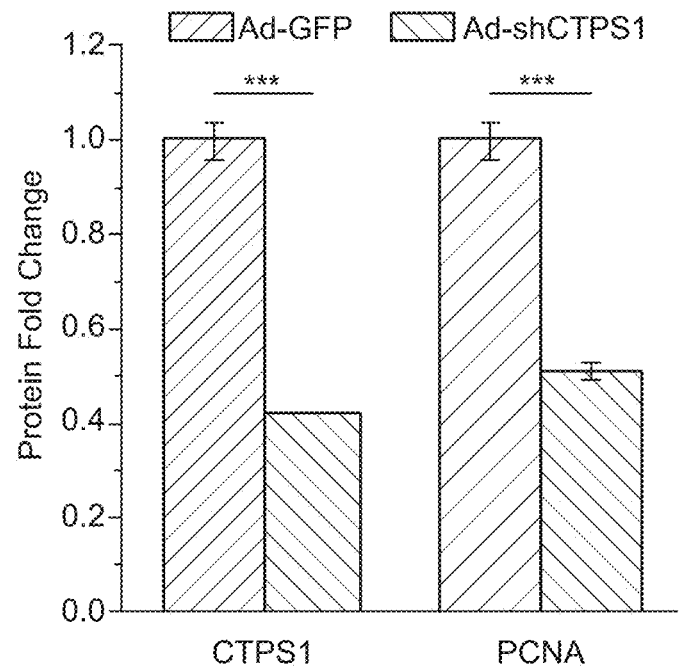
FIG. 2D is a bar graph showing CTPS1 and PCNA expression (fold change) in control SMC and SMC transfected with adenoviral expressed GFP (Ad-GFP) or adenoviral expressed shRNA against CTPS1 (Ad-shCTPS1) (normalized to α-tubulin). $*P<0.05$, $P<0.01$, $*P<0.001$ (n=4).

Materials and Methods
  Reagents
  CPEC (compound 375575) was obtained from the Open Chemical Repository of National Cancer Institute Developmental Therapeutics Program (DTP).
  Construction of Adenoviral Vectors
  NME1 and NME2 cDNA were individually subcloned into the XhoI site of pShuttele-IREShrGFP-1 (Agilent) and was confirmed by sequencing. Adenoviral vectors expressing CTPS1 and NME2 short hairpin RNA (shRNA) (shCTPS1 and shNME2) were constructed and the viruses were purified as described previously (Shi, et al. *Arterioscler. Thromb. Vasc. Biol.*, 31:e19-e26 (2011)). The shRNA sequences were as follows: shCTPS1 top strand: 5'-CGC GTC GCG CTA GAG CAC TCT GCA TTG GCC ATT AAT TCA AGA GAT TAA TGG CCA ATG CAG AGT GCT CTA GCG CTT TTT TCC AAA-3' (SEQ ID NO:12); shCTPS1 bottom strand: 5'-AGC TTT TGG AAA AAA GCG CTA GAG CAC TCT GCA TTG GCC ATT AAT CTC TTG AAT TAA TGG CCA ATG CAG AGT GCT CTA GCG CGA-3' (SEQ ID NO:13); shNME2 top strand: 5'-CGC GTC GAG ATC CAT CTG TGG TTT AAG CCC GAA GAT TCA AGA GAT CTT CGG GCT TAA ACC ACA GAT GGA TCT CTT TTT TCC AAA-3'(SEQ ID NO:14); shNME2 bottom strand: 5'-AGC TTT TGG AAA AAA GAG ATC CAT CTG TGG TTT AAG CCC GAA GAT CTC TTG AAT CTT CGG GCT TAA ACC ACA GAT GGA TCT CGA-3' (SEQ ID NO:15). Green fluorescent protein (GFP)-expressing adenovirus (Ad-GFP) was used as a control.
  Wound Healing Assay
  Cell migration was evaluated by wound healing assay using the CytoSelect Wound Healing Assay Kit (Cell Biolabs). Wound healing inserts were put into 24-well cell culture plates coated with fibronectin. Cell suspension (250 µl) was added to either side of the insert and incubated overnight to form a monolayer. The inserts were then removed to allow the cells to migrate. Images of wound healing were captured using a dissection microscope. Cell migration was quantified by blindly measuring the migration distances.
Results
  To determine if CTPS1 plays a role in SMC proliferation, CTPS activity was blocked using cyclopentenyl cytosine (CPEC), an effective and specific inhibitor for CTPS (Moyer, et al., *Cancer Res.*, 46:3325-3329 (1986); Politi, et al., *Cancer Chemother. Pharmacol.*, 36:513-523 (1995)). As shown in FIG. 2A, blockade of CTPS activity significantly suppressed SMC proliferation in a dose dependent manner. CPEC treatment also dramatically suppressed PCNA expression (FIG. 2C).
  To confirm the specificity of CTPS1 function, CTPS1 expression was blocked by shRNA. It was discovered that knockdown of CTPS1 (FIG. 2D) effectively suppressed PDGF-BB-induced SMC proliferation (FIG. 2C). CTPS1 shRNA appeared to inhibit vehicle-treated SMC growth as well (FIG. 2C). Consistently, CTPS1 knockdown also inhibited PCNA expression (FIG. 2D), further demonstrating the important role of CTPS1 in SMC proliferation.

Figure 3A:
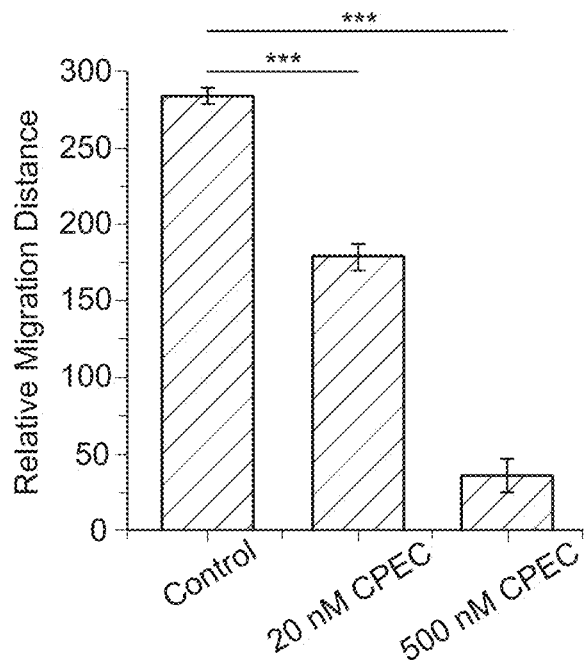
FIG. 3A is a bar graph showing the relative migration distance of control SMC and SMC treated with 20 nM CPEC or 500 nM CPEC.
Figure 3B:
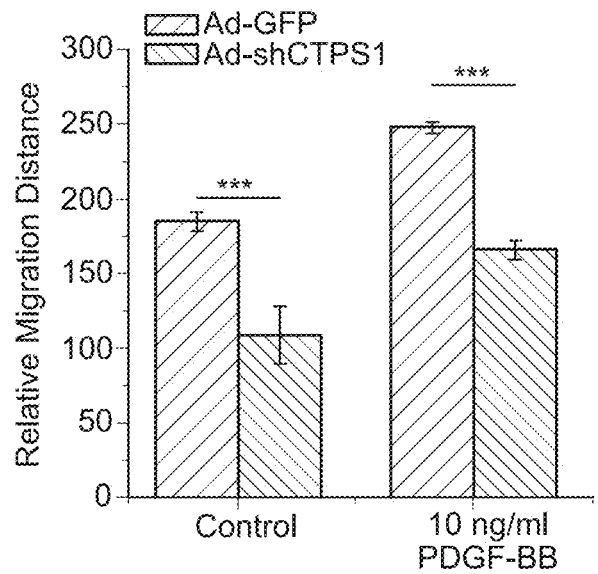
FIG. 3B is a graph showing the relative migration distance of control SMC and SMC treated with 10 ng/ml PDGF-BB and infected with adenoviral expressed GFP (Ad-GFP) or adenoviral expressed shRNA against CTPS1 (Ad-shCTPS1). $*P<0.05$, $P<0.01$, $*P<0.001$ (n=4).

Vascular remodeling following injury is initiated by SMC migration from media layer to intima (Nilsson, et al., *Arterioscler. Thromb. Vasc. Biol.*, 17:490-497 (1997)). Wound healing assay showed that blockade of CTPS1 activity by CPEC inhibited SMC migration in a dose-dependent manner (FIG. 3A). The importance of CTPS1 in SMC migration was also assessed using CTPS1 shRNA. As shown in FIG. 3B, shRNA knockdown of CTPS1 effectively inhibited PDGF-BB-induced SMC migration, consistent with the CPEC treatment.

Figure 4A:
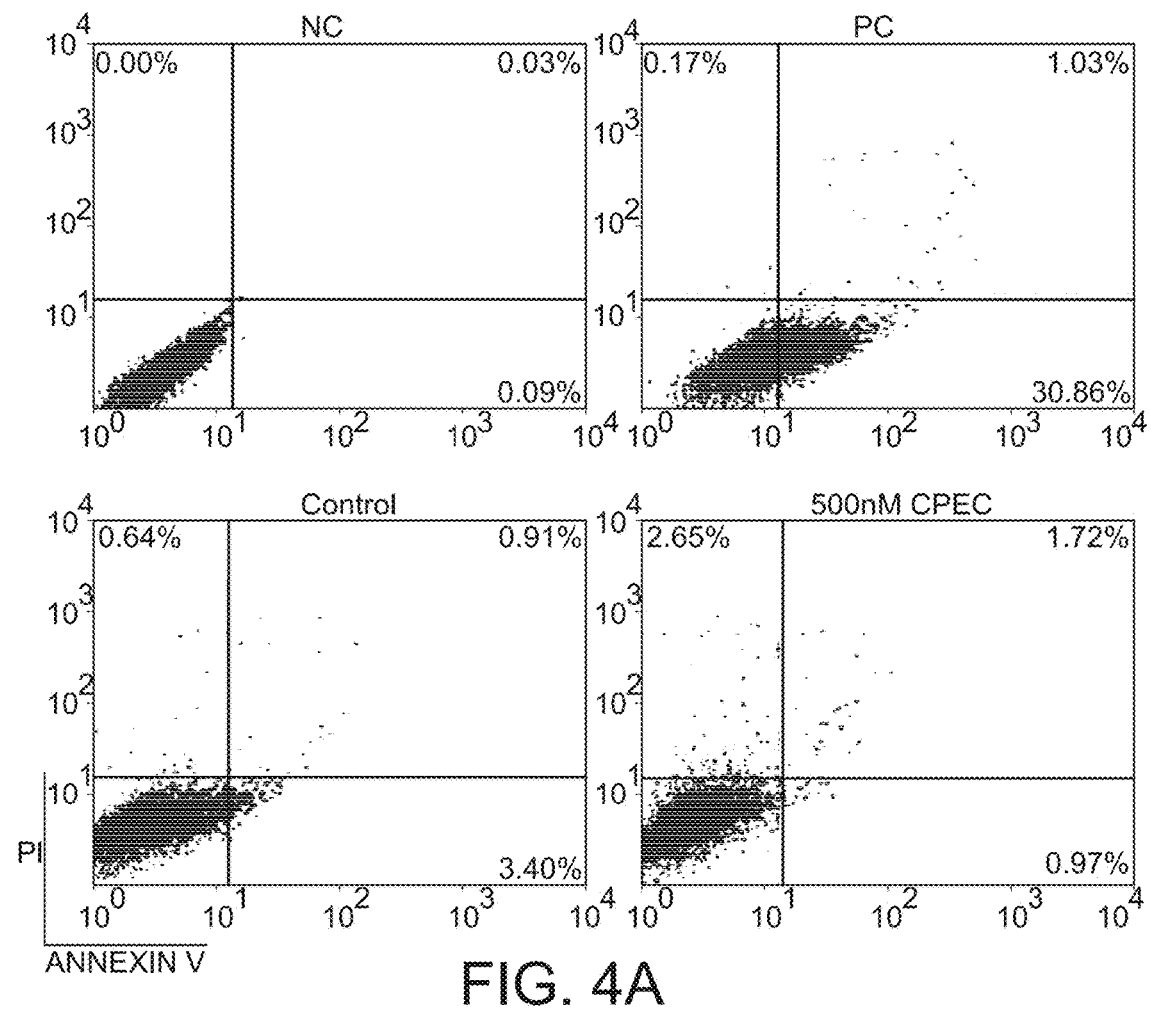
FIG. 4A is a series of scatter plots showing the results flow cytometry analysis of SMC apoptosis (propidium iodide vs. Annexin V) in NC: negative control (top-left panel); PC: positive control (top-right panel); vehicle-treated cells (Control) (bottom-left panel); and cells treated with 500 nM CPEC (bottom-right panel).
Figure 4B:
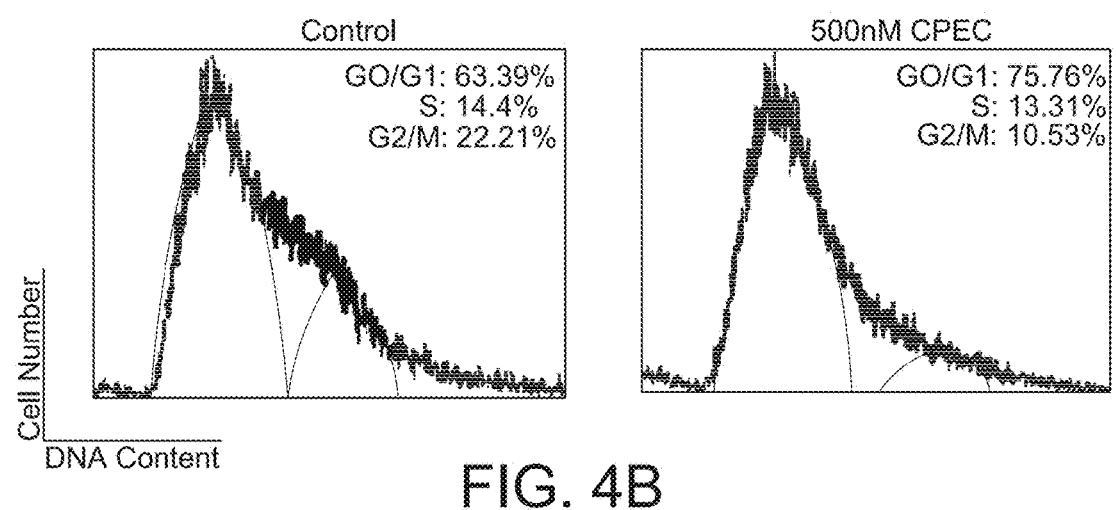
FIG. 4B is a series of plots showing the results of flow cytometry analysis of SMC proliferation (cell number vs. DNA content) for control and 500 nM CPEC treat cells.
Figure 4C:
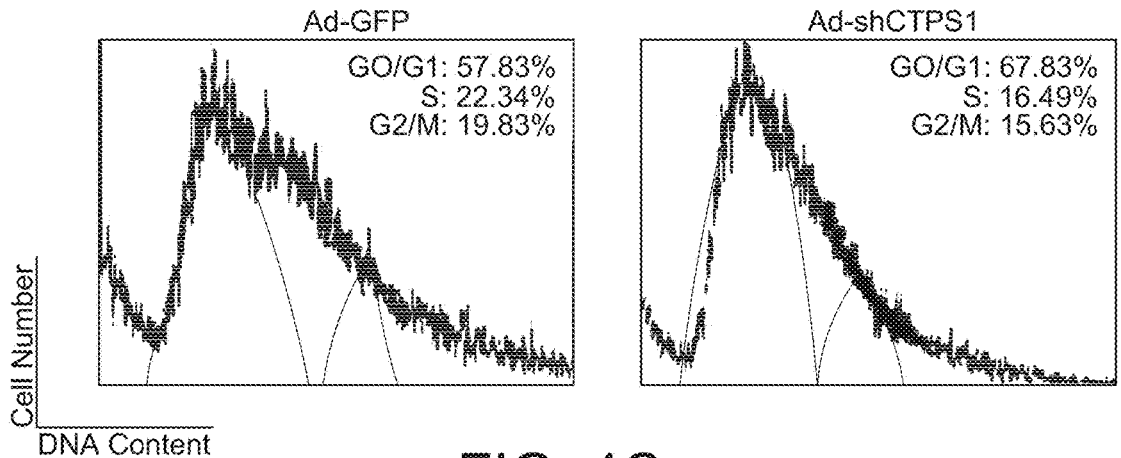
FIG. 4C is a series of plots showing the results of flow cytometry analysis of SMC proliferation (cell number vs. DNA content) for cells infected with adenoviral expressed GFP (Ad-GFP) or adenoviral expressed shRNA against CTPS1 (Ad-shCTPS1).
Figure 4D:
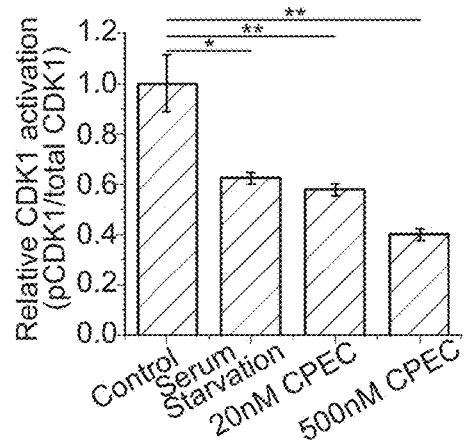
FIG. 4D is a bar graph showing relative CDK1 activation (phosphorylated CDK1/total CDK1) in control SMC and SMC serum-starved, or treated with 20 nM or 500 nM CPEC.
Figure 4E:
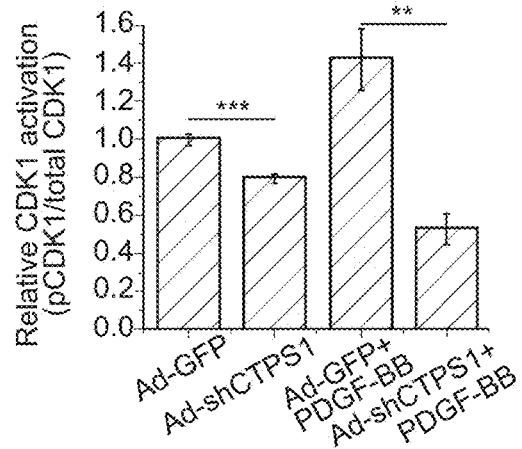
FIG. 4E is a bar graph showing relative CDK1 activation (phosphorylated CDK1/total CDK1) in cells infected with adenoviral expressed GFP (Ad-GFP) or adenoviral expressed shRNA against CTPS1 (Ad-shCTPS1) with or without PDGF-BB treatment. $*P<0.05$, $P<0.01$, $*P<0.001$ (n=4).

Example 3: Blockade of CTPS1 Activity or Expression does not Induce SMC Apoptosis but Impairs Cell Cycle Progression Materials and Methods
  TUNEL Assay
  In vivo cell apoptosis was evaluated by detecting DNA fragmentation using the terminal deoxynucleotidyl transferase (TdT)-mediated dUTP-digoxigenin nick end-labeling method (TUNEL kit, Roche, USA). Apoptotic cells were observed under a fluorescent microscope. In vitro cell apoptosis was measured by Flow Cytometry. Cells were stained with both Annexin V-FITC (BD Biosciences) and propidium iodide (PI) and analyzed on a FACSCALIBUR™ (Becton Dickinson). The percentages of positive-stained cells were quantified using CELLQUEST™ software (Becton Dickinson). Non-stained cells served as controls.
  Cell Cycle Flow Cytometry Analysis
  $1 \times 10^6$ cells were harvested and resuspended in 500 µl of reaction buffer containing 1 µl of Nuclear-IDTM Red dye (Nuclear-IDTM Red Cell Cycle Analysis Kit, Enzo Life Sciences, USA). After mixing, cells were incubated in the dark for 15 min. Cell cycle analysis was performed on a FACSCALIBUR™ (Becton Dickinson) and analyzed by the CELLQUEST™ software (Becton Dickinson).
Results
  Since CPEC is a chemical with potential cytotoxicity, CPEC inhibited SMC proliferation was tested for a non-specific toxic effect. Apoptosis analysis using PI/Annexin V double staining and flow cytometry indicated that 24 h treatment with 500 nM CPEC (the highest dosage used in this study) did not induce SMC apoptosis, comparable with the treatment with vehicle (FIG. 4A). The serum-starved cells were used as a positive control (PC), which caused a significant cell apoptosis (30.86%) (FIG. 4A) (24). However, CPEC treatment or CTPS1 knockdown significantly blocked the cell cycle progression, as indicated by the accumulation of cells in G0/G1 phase (FIG. 4B-4C). It appeared that CPEC treatment (FIG. 4D) or CTPS1 knockdown by shRNA (FIG. 4E) dramatically inhibited the activation of cell cycle regulator CDK1 via suppression of its T161 phosphorylation site.

Example 4: CTPS1 Plays an Important Role in Injury-Induced Vascular Remodeling

Figure 5A:
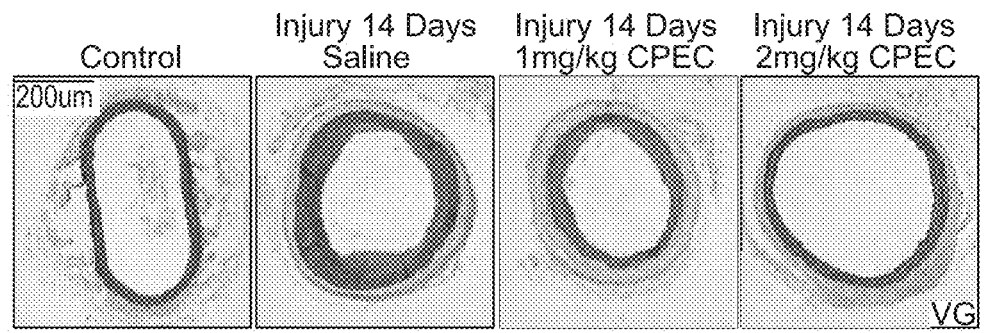
FIG. 5A is a series of micrographs showing neointima formation (elastin (VG) staining) in control and blocked balloon injured arteries of mice treated with saline, 1 mg/kg CPEC, or 2 mg/kg CPEC. Images show arteries 14 days after injury.
Figure 5B:
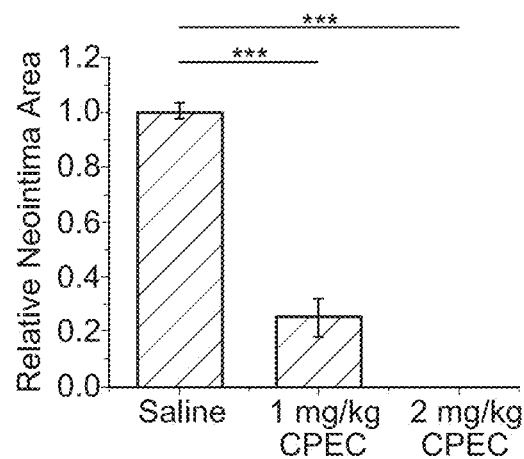
FIG. 5B is a bar graph showing relative neointima formation in blocked balloon injured arteries of mice treated with saline, 1 mg/kg CPEC, or 2 mg/kg CPEC (quantification of FIG. 5A).

Materials and Methods
  Adenoviral Gene Transfer
  Adenovirus gene transfer was achieved by incubation of $5 \times 10^9$ pfu of adenovirus in balloon-injured carotid arteries for 20 min as described previously (Dollery, et al., *Ann. N. Y. Acad. Sci.*, 878:742-743 (1999)).
Results
  Since CTPS1 played an essential role in SMC proliferation and migration in vitro and was induced in neointima SMCs following balloon injury, an experiment was designed to determine if CTPS1 plays an important role in injury-induced neointima formation in vivo. Rat carotid arteries were injured with balloon catheter to induce neointima formation and administered CPEC via mini-osmotic pumps to block CTPS1 activity. A thick layer of neointima was formed 14 days after injury. However, the neointima was dramatically blocked by a low dosage (1 mg/kg body weight/day), and completely blocked by a higher dosage of CPEC (2 mg/kg b.w./day) (FIG. 5A-5B). The PCNA expression was also dramatically blocked by the low dose CPEC and completely blocked by the higher dose CPEC as determined by immunohistochemistry.

Figure 5C:
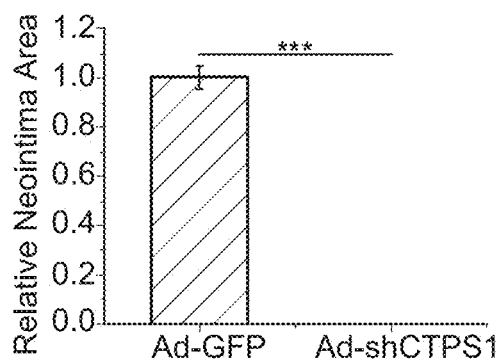
FIG. 5C a bar graph showing relative neointima formation in blocked balloon injured arteries of mice infected with adenoviral expressed GFP (Ad-GFP) or adenoviral expressed shRNA against CTPS1 (Ad-shCTPS1). $*P<0.05$, $P<0.01$, $*P<0.001$ (n=5).

To confirm the specificity of CTPS1 function, CTPS1 was knockdown using adenoviral-mediated shRNA delivery in injured arteries. As shown in FIG. 5C, CTPS1 shRNA dramatically blocked neointima formation as well as PCNA expression in neointima SMCs. To determine whether or not CPEC had a toxic effect on neointima SMCs, the in vivo cell apoptosis was detected by TUNEL assay. Consistent with the in vitro results (FIG. 4A), no apoptotic cells were observed by immunohistochemisty in the vessel sections from CPEC-treated arteries even with the higher dose CPEC (2 mg/kg b.w./day). These results demonstrate that CTPS1 is an ideal drug target for blocking injury-induced neointima formation/vascular remodeling.

Example 5: Blockade of CTPS1 Activity or Expression Impacted ECs Differently from SMCs in Vitro and Promoted Re-Endothelialization in Vivo Materials and Methods
Cell Proliferation Assay
Cell proliferation was evaluated with 3-(4,5-dimethylthiazol-2-yl)-2,5-diphenyltetrazolium (MTT) assay using a TACS MTT Cell Proliferation Assay Kit (Trivegen). The optical density at 570 nm was measured.

Mouse Carotid Artery Wire Injury Model
Mice were anesthetized with ketamine hydrochloride (80 mg/kg IP) and xylazine (5 mg/kg IP), a 0.38-mm flexible angioplasty guidewire was advanced by 1 cm via a transverse arteriotomy of the external carotid artery, and endothelial denudation of the common carotid artery was achieved by 3 rotational passes (Werner, et al., *Circ. Res.*, 93:e17-e24 (2003)).

Figure 6A:
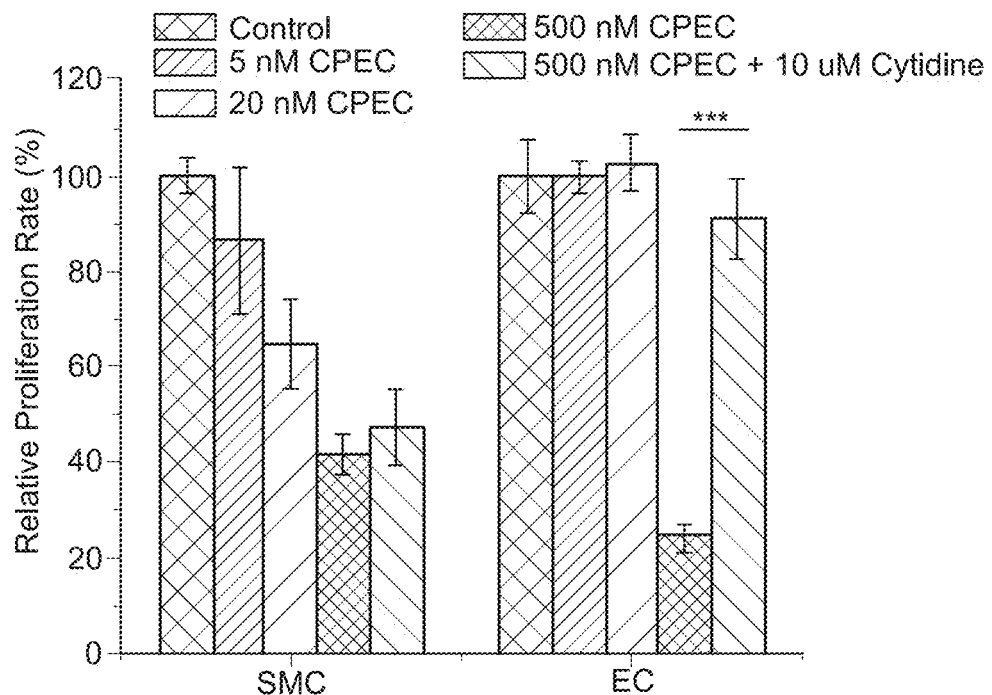
FIG. 6A is a bar graph showing the relative proliferation rate (%) of smooth muscle cells (SMC) and endothelial cells (EC) untreated (control) or treated with 5 nM CPEC, 20 nM CPEC, 500 nM CPEC, or 500 nM CPEC+10 μM cytidine.
Figure 6B:
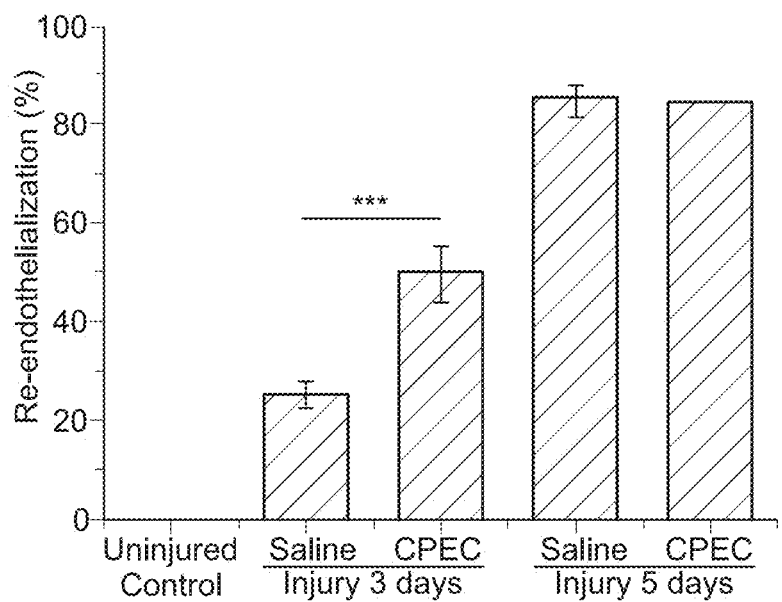
FIG. 6B is a bar graph showing quantification of re-endothelialization (%) in wire-injured mouse arteries for uninjured animals (control) and saline or CPEC treated animals 3 and 5 days after injury. $*P<0.05$, $P<0.01$, $*P<0.001$ (n=5).
Figure 6C:
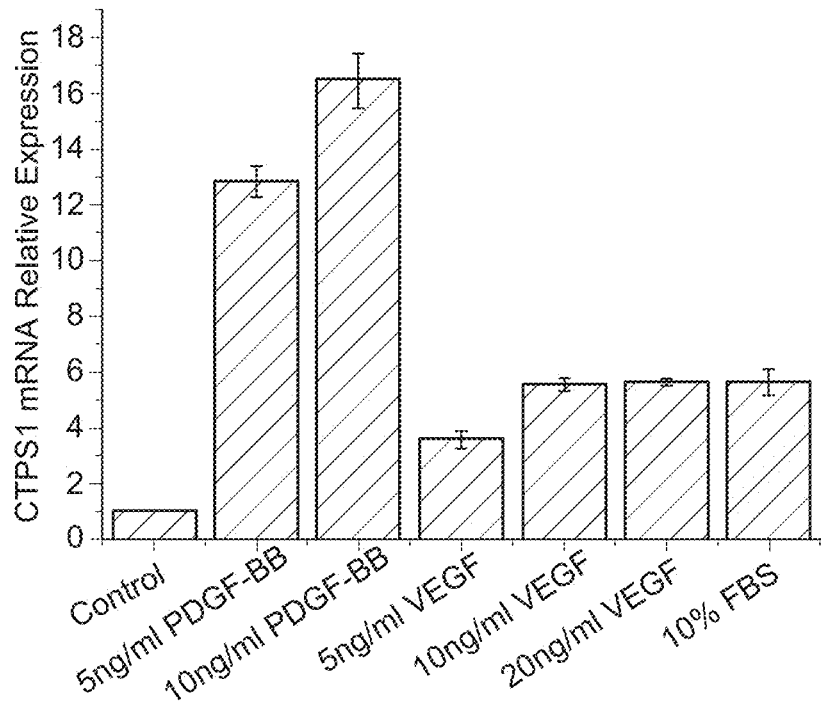
FIG. 6C is a bar graph showing the relative mRNA expression levels of CTPS2 in proliferation endothelial cells (C166 cells) when treated with various concentrations of PDGF-BB, VEGF, or 10% FBS.

Results
Re-endothelialization is an important step toward successful vascular repair in injury-induced vessel wall remodeling. Current anti-neointima strategies targeting genes or signaling pathways for SMC proliferation also block re-endothelialization and cause thrombosis as a side effect (Hofma, et al., *Eur. Heart J*, 27:166-170 (2006); Hofma, et al., *Eur. Heart J*, 27:166-170 (2006). It is important, therefore, to identify drug targets that do not block re-endothelialization. Since CTPS1 played a very important role in neointima formation, experiments were designed to determine if blocking CTPS1 activity or expression has any effect on ECs. CPEC was tested for an effect on EC proliferation and migration in vitro. As shown in FIG. 6A, EC proliferation was not affected by low dosages of CPEC treatments (≤20 nM), in which SMC proliferation was attenuated, indicating that SMCs are more sensitive than ECs to CPEC challenge. A higher dosage of CPEC (500 nM) significantly blocked the proliferation of both SMCs and ECs, indicating that a certain level of CTPS activity is required for EC proliferation. Indeed, CTPS1 was induced in ECs by different growth stimuli (FIG. 6C). Interestingly, addition of extracellular cytidine restored EC, but not SMC, proliferation that was originally blocked by the high dosage of CPEC (FIG. 6A), indicating that SMCs and ECs may use different pathways to regulate their CTP synthesis, and consequently their proliferation. Since high dosage of CPEC did not have toxic effect on cells (FIG. 4A), ECs were treated with 500 nM of CPEC and it was found that CPEC had no effect on EC migration although the high dosage of CPEC inhibited EC proliferation (FIG. 6A).

Figure 6D:
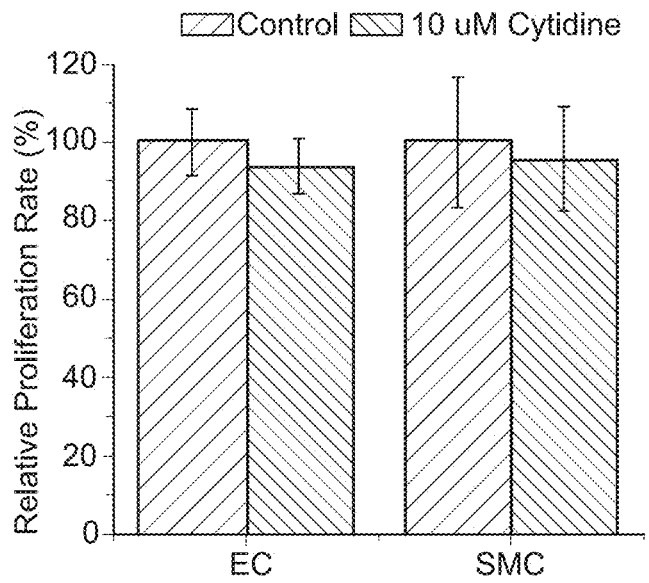
FIG. 6D is a bar graph showing the relative proliferation rate (%) of endothelial cells (EC) and smooth muscle cells (SMC) in the presence or absence of abundant (10 μM) cytidine.

Although cytidine is important for EC proliferation, abundant CTP alone seemed not to be able to stimulate either EC or SMC proliferation (FIG. 6D), probably because the proliferation also requires many other factors including cyclin-dependent kinase activity.

Figure 6E:
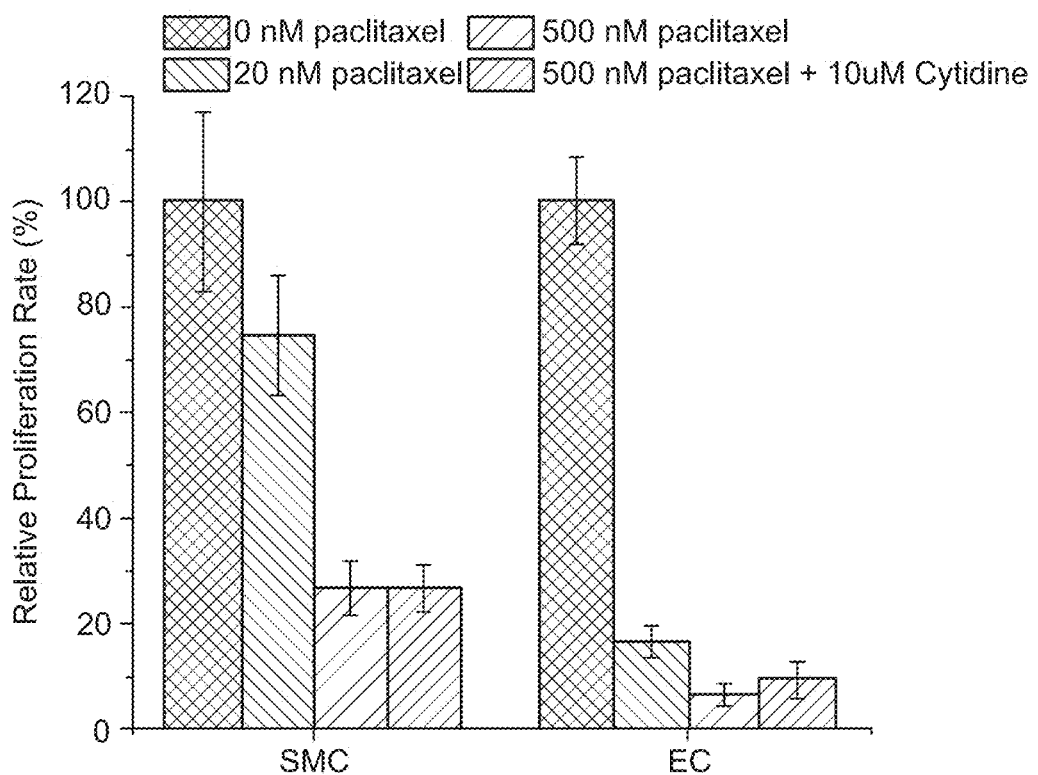
FIG. 6E is a bar graph showing the relative proliferation rate (%) of endothelial cells (EC) and smooth muscle cells (SMC) with increasing concentrations of paclitaxel (0 nM, 20 nM, 500 nM) and 500 nM paclitaxel with 10 μM cytidine.

Paclitaxel (Taxus), one of the drugs currently used for coating stents and treating coronary artery diseases, effectively blocks SMC proliferation and restenosis after angioplasty. However, paclitaxel suppressed both EC and SMC proliferation at a lower (20 nmol/L) or higher dosage (500 nmol/L; FIG. 6E), consistent with previous reports. Unlike blockade of CTPS1, paclitaxel-mediated inhibitory effect could not be restored by cytidine (FIG. 6E). In addition, ECs seemed to be more sensitive to paclitaxel than SMCs. These results suggest that blocking CTPS1 may be a better strategy to block restenosis during cardiovascular intervention.

Figure 6F:
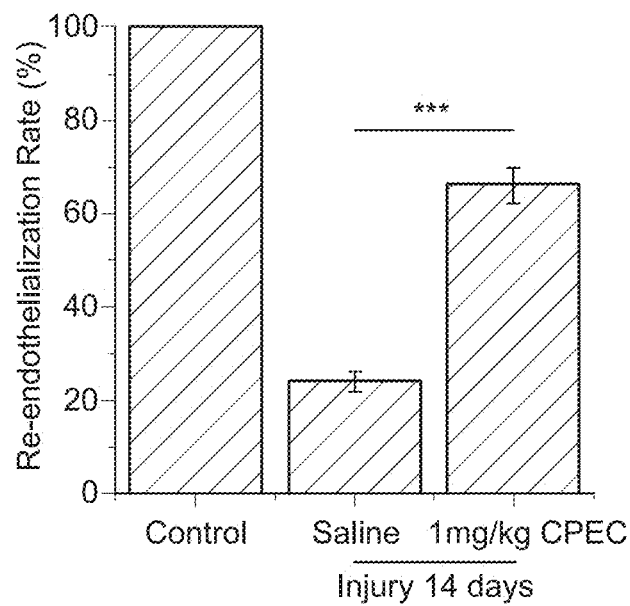
FIG. 6F is a bar graph showing re-endothelialization (%) relative to control (day 14) of injured rats treated with saline or 1 mg/kg CPEC, $*P<0.05$, $P<0.01$, $*P<0.001$ (n=5).

To determine if CTPS1 plays a role in re-endothelialization during vascular remodeling in vivo, CPEC was administered systematically via osmotic pump into rats with balloon-injury or mice with wire-injury in their carotid arteries. A weak re-endothelialization was found in the carotid arteries after 60 days of vascular injury as indicated by the expression of EC marker CD31, indicating a slow and weak proliferation of ECs during the natural vascular repair process. However, CPEC administration (1 mg/kg/day) induced a strong re-endothelialization 14 days after the injury while significantly inhibiting the neointima formation as compared to saline-treated arteries. Quantification of the re-endothelialization areas in Evans blue-stained vessel showed that CPEC treatment increased the re-endothelialization area to 66% of the injured vessels compared with 24% in saline-treated vessels (FIG. 6F). Consistently, PCNA was strongly expressed in CD31-positive cells, indicating that CPEC treatment preserved or promoted EC proliferation in injured vessel.

These results demonstrate that CPEC triggered an alternative pathway, which had preserved or even promoted the re-endothelialization during vascular repair. The specificity of CPEC effect on CTPS1 activity was confirmed by adenovirus-mediated CTPS1 shRNA. Knockdown of CTPS1 induced re-endothelialization while blocking neointima formation, similar to the effect observed in CPEC treatment. The re-endothelialization in the injured vessel segments after CPEC treatment was also observed via Evans Blue staining.

To further establish CTPS function in re-endothelialization after vascular injury, the endothelial denudation and re-endothelialization was tested in a different model, i.e., mouse wire-injury model. The re-endothelialization was observed in the intact carotid arteries using Evans Blue staining of the injured areas. Systematic administration of CPEC was achieved via osmotic pump (1 mg/kg/day). Re-endothelialization in mouse arteries occurred rapidly following injury (FIG. 6B). 5 days after injury, re-endothelialization was completed, consistent with the previous reports (Hagensen, et al., *Cardiovasc Res.*, 93:223-231 (2012)). CEPC treatment did not delay the rapid re-endothelialization.

Importantly, at 3 days after the injury, CPEC-treated arteries appeared to have a larger area that was re-endothelialized compared to saline-treated arteries (FIG. 6B), indicating that CPEC accelerated the re-endothelialization process. Taken together, these data demonstrate that blocking CTPS function or expression promotes re-endothelialization during injury-induced vascular repair and remodeling.

Example 6: Induction of CTP Synthesis Salvage Pathway Sustains the Proliferation of CPEC-Treated ECs and Promotes Re-Endothelialization of the Injured Vessel Materials and Methods
Quantitative RT-PCR (qPCR) and Western Blot Total RNA was extracted from cells or tissues using Trizol reagent (Invitrogen) and reverse transcribed to cDNA using M-MLV reverse transcriptase (Promega). qPCR was performed on a Stratagene Mx3005 qPCR thermocycler (Agilent Technologies, La Jolla, Calif.). Western blot was performed as described previously (Shi, et al., *J. Biol. Chem.*, 287:6860-6867 (2012)).

Results

Since ECs, but not SMCs, used extracellular cytidine to restore cell proliferation in high dose CPEC treatment (FIG. 6A), the alternative pathway that regulates EC proliferation was investigated. CTPS synthesizes CTP via a so-called "neo-synthesis pathway" using UTP, ATP and glutamine as substrates (Iyengar, et al., *Biochem. J.*, 369:497 (2003)). However, there is a "salvage pathway" utilizing cytidine as substrate when neo-synthesis pathway is in deficiency (Anderson, et al., *Trends Pharmacol. Sci.*, 18:387-392 (1997); Schimmel, et al., *Curr. Cancer Drug Targets.*, 7:504-509 (2007)). Cytidine is utilized by several salvage pathway enzymes, including UCK1/2, CMPK, and nucleoside diphosphate kinase A and B (NME1 and NME2) (Payne, et al., *J. Biol. Chem.*, 260:10242-10247 (1985); Sandeck et al., *PLoS One.*, 4(8): e6554 (2009)).

Figure 7A:
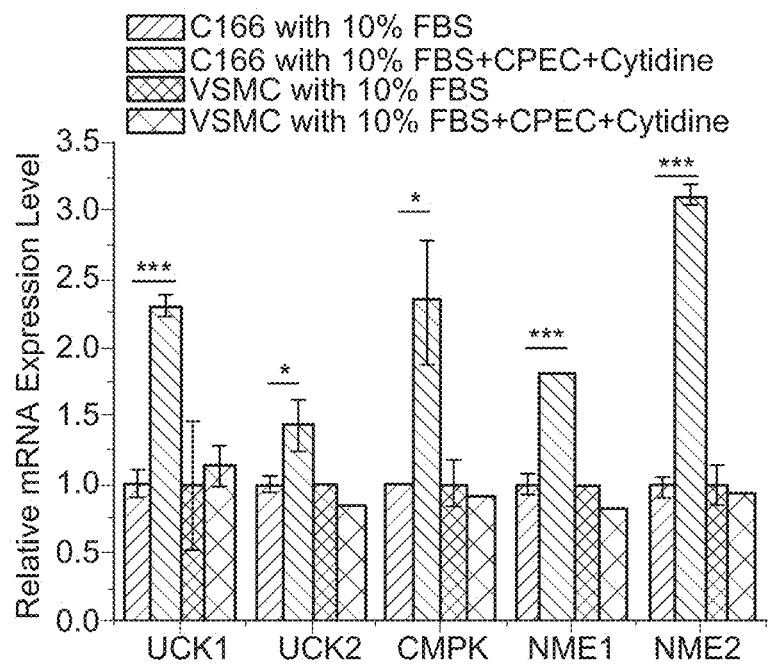
FIG. 7A is a bar graph showing mRNA expression (relative expression level) of salvage pathway-related genes (UCK1, UCK2, CMPK, NME1, and NME2) in ECs (C166) and SMCs (VSMC) with or without the addition of CPEC and cytidine.
Figure 7B:
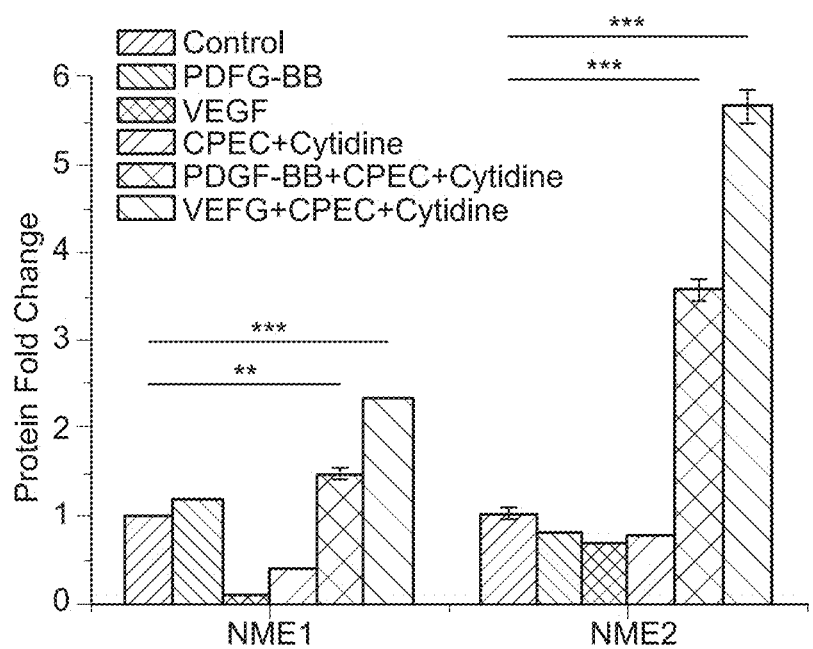
FIG. 7B is a bar graph showing quantification of NME1 and NME2 protein expression was induced in ECs by CPEC in the presence of both cytidine and growth factors (PDGF-BB or VEGF) (normalized to α-tubulin).

As shown in FIG. 7A, treatment with CPEC in the presence of cytidine significantly induced mRNA expression of all the salvage pathway enzymes in ECs, but not in SMCs, indicating that ECs, but not SMCs, are able to use the salvage pathway when CTPS pathway is blocked. Since NME1/2 play similar roles in the salvage pathway as CTPS in the neo-synthesis pathway, and the end product of both NMEs and CTPS is CTP, NME1 or NME2 are most likely to be responsible for CPEC-induced EC proliferation. CPEC appeared to induce more NEM2 expression than NME1 in proliferative ECs (FIG. 7A). Interestingly, PDGF-BB, VEGF, or CPEC treatment alone did not upregulate the expression of NME1 or NME2 in ECs. However, combination of CPEC with either one of the growth factors (VEGF or PDGF) in the presence of cytidine dramatically up-regulated the NME especially the NME2 expression (FIG. 7B). These data indicate that an elevated level of the salvage pathway activities may be required for EC proliferation when the neo-synthesis pathway is blocked.

Figure 7C:
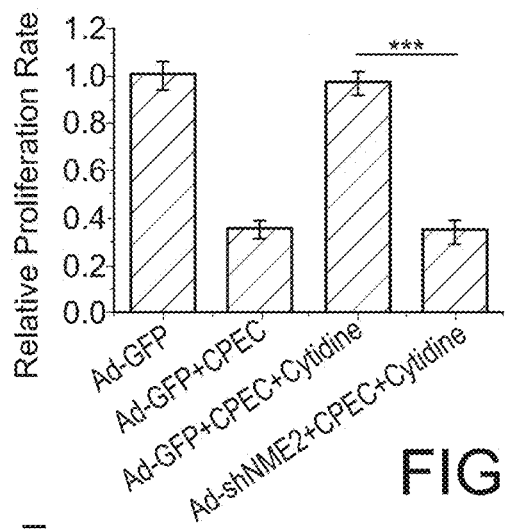
FIG. 7C is a bar graph showing relative proliferation rate in EC infected with adenoviral expressed GFP (Ad-GFP) or adenoviral expressed shRNA against CTPS1 (Ad-shCTPS1), with or without CPEC+cytidine. *$P<0.05$, $P<0.01$, *$P<0.001$ (n=5).
Figure 7D:
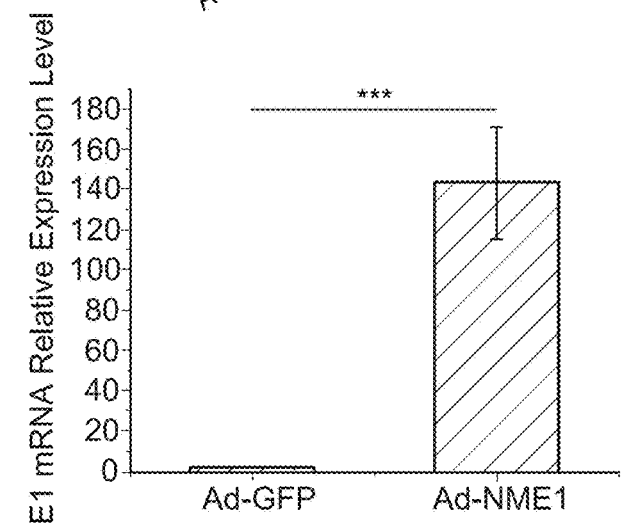
FIG. 7D is a bar graph showing the relative expression of NME1 mRNA in control (Ad-GFP) and NME1 overexpressing (Ad-NME1) cells as assayed by qPCR, *$P<0.05$, $P<0.01$, *$P<0.001$ (n=3).
Figure 7E:
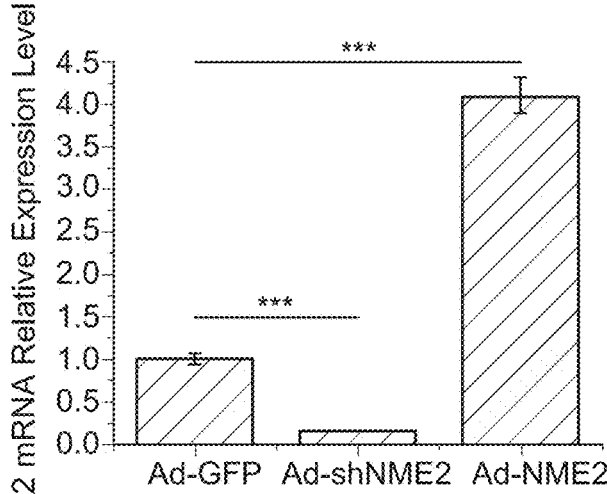
FIG. 7E is a graph showing relative expression of NME2 mRNA in control (Ad-GFP), NME2 knockdown (Ad-shNME2) and NME2 overexpressing (Ad-NME2) cells as assayed by qPCR, *$P<0.05$, $P<0.01$, *$P<0.001$ (n=3).
Figure 7F:
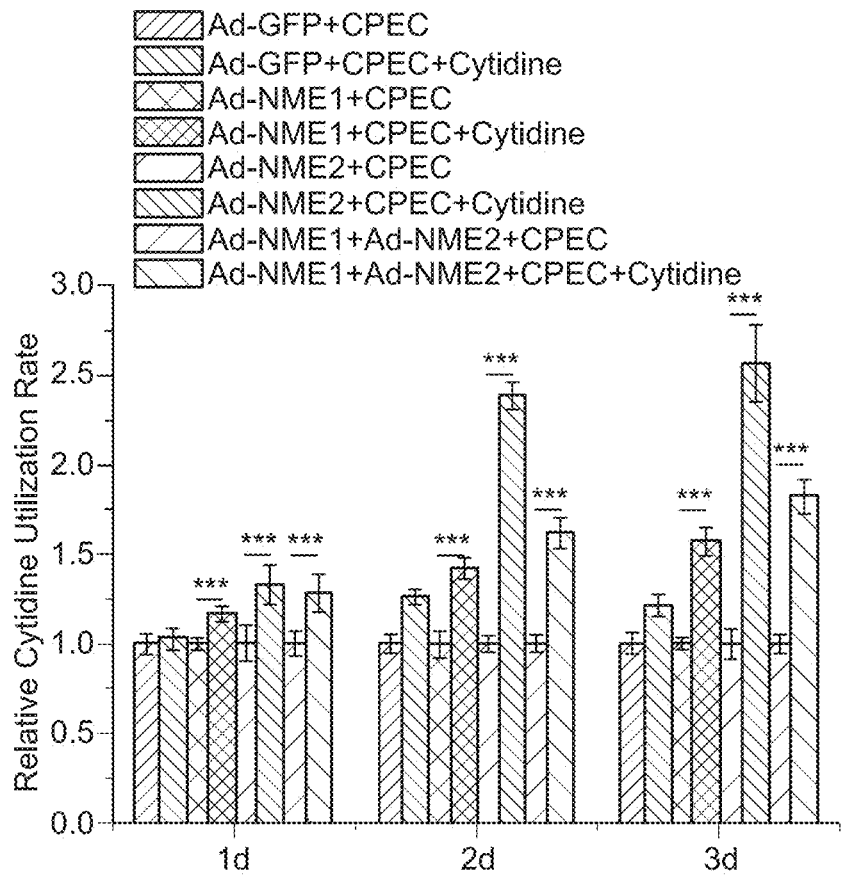
FIG. 7F is a bar graph showing the relative cytidine utilization rate of control cells (Ad-GFP) and cells overexpressing NME1 (Ad-NME1), NME2 (Ad-NME2), or NME1+NME2 (Ad-NME1+Ad-NME2), and treated with CPEC, and with or without cytidine, *$P<0.05$, $P<0.01$, $P<0.001$ (n=8).

Although both NME1 and NME2 are important for the nucleoside diphosphate kinase activity in the salvage CTP synthesis pathway (Postel, et al., *Mol. Cell. Biochem.*, 329: 45-50 (2009)), NME2 overexpression in SMCs (FIG. 7D-7E) displayed a stronger activity than NME1 in utilizing cytidine to restore CPEC-attenuated proliferation (FIG. 7F). Consistently, knockdown of NME2 by adenovirus-expressed shRNA dramatically decreased cytidine-mediated restoration of EC proliferation that was originally blocked by a high dose CPEC (FIG. 7C), demonstrating the important role of NME2 in utilizing cytidine to mediate EC proliferation.

The effect of NME2 can be confirmed with its specific inhibitor ellagic acid (EA) (Malmquist, et al., *Proc. West. Pharmacol. Soc.*, 2001:57-60 (1998)).

EA blocked cytidine-restored EC proliferation in a dose-dependent manner. These results indicate that NME2 protects ECs from CPEC challenge through utilizing cytidine as the substrate for CTP salvage synthesis pathway. To test if NME2 is involved in the re-endothelialization in vivo, NME2 expression was examined in arteries undergoing vascular repair following injury-induced vascular remodeling Immunohistochemistry revealed that NME2 was expressed mainly in ECs but not SMCs in arteries.

Figure 7G:
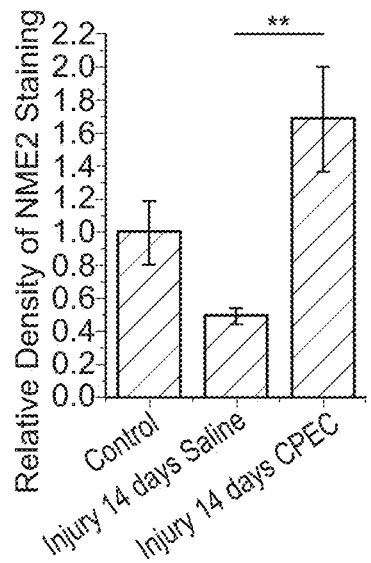
FIG. 7G is a bar graph showing the relative density of NME2 staining in control and injured arteries treatment undergoing vascular repair treated with or without CPEC.

CPEC treatment induced a strong NME2 expression in ECs of the arteries with enhanced re-endothelialization, indicating that NME2 may be important for the re-endothelialization. To test this, NME2 expression was examined in arteries undergoing vascular repair after injury-induced vascular remodeling. NME2 was expressed mainly in ECs, but not SMCs, in arteries. CPEC treatment induced a strong NME2 expression in ECs of the arteries with enhanced re-endothelialization, indicating that NME2 may be important for the re-endothelialization (FIG. 7G).

Figure 7H:
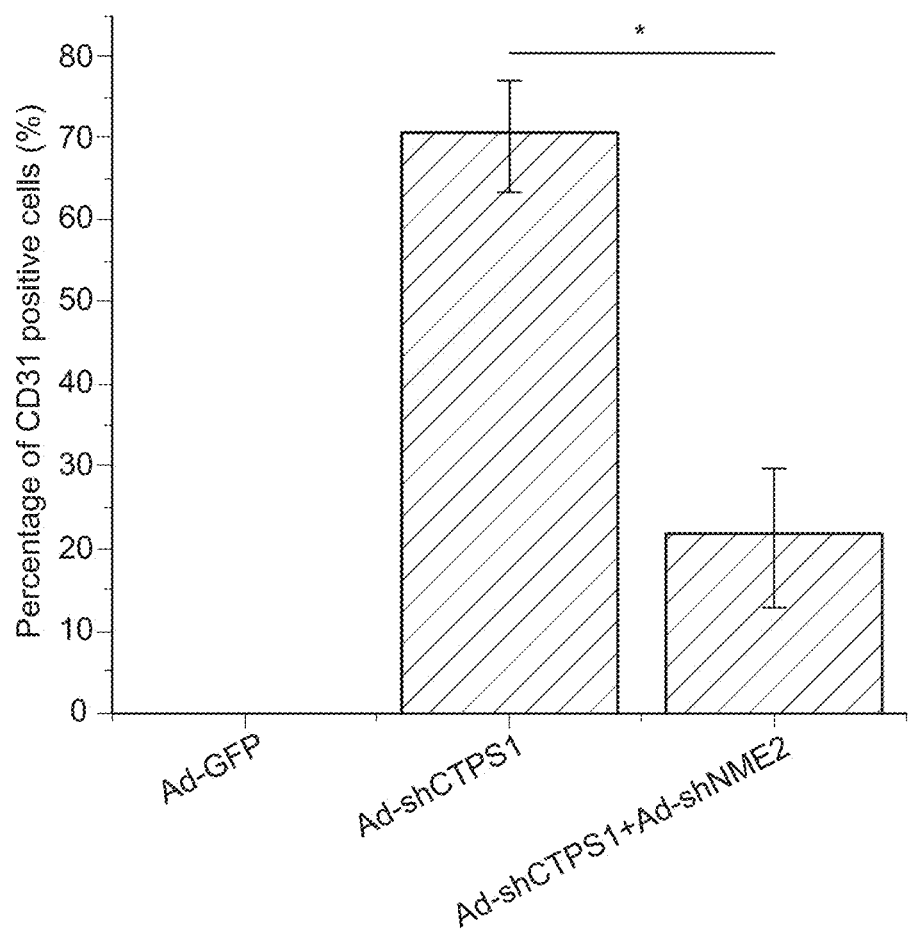
FIG. 7H is a bar graph showing the relative percentage of CD31-positive cells in injured arteries, *$P<0.05$, $P<0.01$, *$P<0.001$ (n=5).

Additionally, both CTPS1 and NME2 were knocked down using shRNAs in injured rat carotid arteries Immunohistochemistry revealed that knockdown of CTPS1 and NME2 simultaneously suppressed re-endothelialization as indicated by the loss of CD31 positive cells as compared to CTPS1 knockdown alone (FIG. 7H). In agreement with the effect of NME2 knockdown, blockade of NME2 activity by EA administration (10 mg/kg/day) dramatically impaired the re-endothelialization of wire-injured mouse carotid artery in the presence of CPEC. These data demonstrate that NME2 is important for the proliferation of ECs when the cells are treated with CPEC, which facilitates the re-endothelialization in vivo.

Using both pharmacological and loss of function approaches, Examples 1-6 collectively demonstrate that targeting CTPS1 can effectively suppress neointima formation following vascular injury. Importantly, low dosages of CPEC inhibit SMC, but not EC growth, indicating that ECs are less sensitive to CPEC treatment. High dosage of CPEC suppresses both SMC and EC proliferation, indicating that a relatively low level of CTPS activity is required for EC proliferation. The inhibitory effect of high dosage of CPEC can be reversed by addition of cytidine, a substrate for CTP synthesis salvage pathway, indicating that salvage pathway is very important for EC proliferation. Thus, the Examples demonstrate that SMCs and ECs have a distinct preference in utilizing CTP synthesis pathways for their proliferation. SMCs appear to mainly utilize CTPS-mediated de novo synthesis pathway. Although CTPS-mediated pathway is much less essential for ECs, ECs appear to use both de novo and salvage pathways to synthesize CTP.

Examples 1-6 are supportive of a strategy to potentially overcome a long-standing medical challenge, i.e., the impaired re-endothelialization in anti-neointima therapy following cardiovascular interventions. Drug-eluting stents (DES) are a common treatment for coronary artery diseases. However, drugs currently used in clinic such as sirolimus-(Cypher) and paclitaxel-(Taxus) have side effects causing defective re-endothelialization and increasing risk of late thrombosis (Finn, et al., *Circulation.*, 115:2435-2441 (2007)). The results of Examples 1-6 collectively indicate that blockade of CTPS1 function accelerates re-endothelialization in two injury models, which is likely due to the reduction of proliferating SMCs as well as the induction of NME-mediated salvage pathways. Proliferative SMCs are known to produce various paracrine factors such as endostatin and thrombospondin to inhibit EC proliferation (Dhanabal, et al., *J. Biol. Chem.*, 274:11721-11726 (1999); Stouffer, et al., *Circulation*, 97:907-915 (1998); Dawson, et al., *J Cell Biol.*, 138:707-717 (1997)). Reduction of proliferating SMCs benefits re-endothelialization as long as EC proliferation is not inhibited, which can be achieved via the activation of CTP salvage pathway. Salvage pathway enzymes NME2 appears to be expressed at a relatively low level in normal EC growth condition. However, when CTPS activity is blocked by CPEC, NME2 is dramatically induced in ECs while neointima proliferating SMCs are significantly reduced.

Although both NME1 and NME2 are important for CTP synthesis, NME2 appears to have a stronger capability in utilizing cytidine. Indeed, knockdown of NME2 significantly diminishes EC proliferation in the presence of CPEC and cytidine. These results demonstrate that the salvage pathway is up-regulated in order to compensate for CPEC-blocked CTP synthesis, which sustains the EC proliferation. The combined effect of blocking CTPS1 on inhibiting SMC proliferation while sustaining EC proliferation results in the accelerated re-endothelialization in EC-denuded vessels.

It is interesting that ECs, but not SMCs, utilize salvage pathways to synthesize CTP, which is likely due to the accessibility of ECs to the salvage pathway-specific substrate cytidine. Cytidine is circulating in the blood stream, which consistently interacts with ECs. Therefore, ECs may adopt a unique mechanism by which cytidine is used to synthesize CTP even under normal growing or quiescent states. This specialized ability is obviously enhanced when the de novo pathway is impaired.

Targeting CTPS is likely to result in significantly-improved vascular repair. In addition to CPEC, several other inhibitors including 3-deazauridine (3-DU) (Gao, et al., *Nucleosides, Nucleotides Nucleic Acids*, 19:371-377 (2000)) carbodine (Georges-Courbot, et al., *Agents Chemother.*, 50:1768-1772 (2006)) and 6-diazo-5-oxonorleucine (DON) (Bearne, et al., *Biochem. J.*, 356:223 (2001) also effectively block CTPS activity, which further make CTPS as a promising target in curing proliferative vascular diseases including those observed in cardiovascular interventions.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of reducing proliferation of vascular smooth muscle cells or reducing neointima formation in a subject comprising implanting into the subject a medical device comprising an effective amount of a CTP synthase 1 (CTPS1) inhibitor to reduce proliferation of vascular smooth muscle cells (VSMC) in the subject to a greater degree than the inhibitor reduces endothelial cell proliferation in the subject, wherein the CTPS1 inhibitor is a nucleoside analog.

2. The method of claim 1, wherein the amount of CTPS1 inhibitor is not sufficient to reduce proliferation of endothelial cells in the subject.

3. The method of claim 1, wherein the degree to which VSMC proliferation is reduced relative to EC proliferation is effective to (i) reduce neointima formation at the site of implantation of the device in the subject, (ii) permit or promote re-endothelialization at the site of implantation of the device in the subject, or (iii) a combination thereof.

4. The method of claim 1, wherein nucleoside analog is selected from the group consisting of cyclopentenyl cytosine (CPEC), cyclopentenyl cytosine 5'-triphosphate (CPEC-TP), 3-deazauridine (3-DU), (+) carbodine, (−) carbodine, and pharmacologically active salts thereof.

5. The method of claim 3, wherein nucleoside analog is selected from the group consisting of cyclopentenyl cytosine (CPEC), cyclopentenyl cytosine 5'-triphosphate (CPEC-TP), 3-deazauridine (3-DU), (+) carbodine, (−) carbodine, and pharmacologically active salts thereof.

6. The method of claim 1, wherein the CTPS1 inhibitor is incorporated into or encapsulated in a delivery vehicle for delivering the CTPS1 inhibitor to vascular smooth muscle cells.

7. The method of claim 6, wherein the delivery vehicle is selected from the group consisting of nanoparticles, microparticles, micelles, synthetic lipoprotein particles, liposomes, and carbon nanotubes.

8. The method of claim 1, wherein a targeting signal for enhancing delivery of the CTPS1 inhibitor to vascular smooth muscle cells is (i) operably linked to the CTPS1 inhibitor, or (ii) operably linked to the delivery vehicle for delivering the CTPS1 inhibitor to vascular smooth muscle cells.

9. The method of claim 8, wherein the targeting signal binds to Tissue Factor, $\alpha_v\beta_3$ integrin, or a marker of a clot or thrombosis selected from the group consisting of fibrin, gpIIb/IIIa, tissue factor/VIIA complex, activated clotting factor Xa, activated clotting factor IXa, and the fibrin condensation product d-dimer.

10. The method of claim 1, wherein the CTPS1 inhibitor is coated onto or incorporated into the device.

11. The method of claim 1, wherein the device is selected from the group consisting of implants, stents, and valves.

12. The method of claim 11 wherein the device is a drug eluting stent that elutes the CTPS1 inhibitor or a delivery vehicle comprising the CTPS1 inhibitor.

13. The method of claim 1, wherein the site of implantation or a site adjacent thereto comprises an injury in need of re-endothelialization, and wherein re-endothelialization occurs faster in the presence of the device than a control device without the CTPS1 inhibitor.

14. The method of claim 1, wherein the subject has a vascular proliferation disorder or vascular trauma, or has undergone or is undergoing angioplasty, vascular surgery, or transplantation arteriopathy.

15. The method of claim 1 further comprising administering to the subject cytidine or a cytidine analog.

16. The method of claim 1, wherein the amount of CTPS1 inhibitor reduces proliferation of VSMC to a greater degree than the inhibitor reduces EC proliferation in an in vitro cell proliferation assay.

17. The method of claim 1, wherein the amount of CTPS1 inhibitor reduces proliferation of VSMC to a greater degree than the inhibitor reduces EC in a rodent carotid artery wire injury model.

18. The method of claim 1, wherein the VSMC are media layer VSMC.

19. A method of reducing proliferation of vascular smooth muscle cells or reducing neointima formation in a subject comprising implanting into the subject a medical device comprising an effective amount of cyclopentenyl cytosine (CPEC)

to reduce proliferation of vascular smooth muscle cells (VSMC) in the subject to a greater degree than the CPEC reduces endothelial cell proliferation in the subject.

20. The method of claim 19, wherein the VSMC are media layer VSMC, and the degree to which the media layer VSMC proliferation is reduced relative to the EC is effective to (i) reduce neointima formation at the site of implantation of the device in the subject, (ii) permit or promote re-endothelialization at the site of implantation of the device in the subject, or (iii) a combination thereof.

* * * * *

SEQUENCE LISTING

```
<160> NUMBER OF SEQ ID NOS: 15

<210> SEQ ID NO 1
<211> LENGTH: 3217
<212> TYPE: DNA
<213> ORGANISM: Homo sapiens

<400> SEQUENCE: 1
tccctcgccc ggaggcagag atgcgctggc gcatcaccgc caggagccca cagtgaaaga      60
ccatcggatg gaaggcgacg cccagaactc caggagaccg ctgtgggagg acgcgaggcc     120
aggtgacgaa taggccaggc gtgagttccc aaacagcctc ctcccttca agagagtaag     180 cttgggccac aggctgggac ggaagcagag gggcagacac gccaccaccc gcccggcctc     240
gaacctacgg cggcacagtt cagcggaggc ggcccagcgg tcctgtcccg cgcctgcgca     300
ctccaggccc cgcccgccc cgcgccctcc aggcccggcc cgccctccaa cctctgcgtg     360
cgcacagcct agagcccgcc tccgtgaaag actgccgggc gcatgcggtc ggggttgttc     420
actggctgtc cggggctccg cgcgcgtcgc cggcccagct ctgtcgctga cgggaggatc     480
tgaagccggc cgcaggtcaa agagtaaaat gaagtacatt ctggttactg gtggtgttat     540
atcaggaatt ggaaaaggaa tcattgccag cagtgtgggc acaatactca agtcatgtgg     600
tttacatgta acttcaatca aaattgaccc ctacattaac attgatgcag gaacattctc     660
tccttatgag catggtgagg tttttgtgct ggatgatggt ggggaagtag accttgacct     720
gggtaactat gagcggttcc ttgacatccg cctcaccaag gacaataatc tgaccactgg     780
aaagatatac cagtatgtca ttaacaagga acggaaagga gattacttgg ggaaaactgt     840
ccaagttgtc cctcatatca cagatgcaat ccaggagtgg gtgatgagac aggcgttaat     900
acctgtagat gaagatggcc tggaacctca agtgtgtgtt attgagcttg gtggaaccgt     960
gggggacata gaaagcatgc cctttattga ggccttccgt cagttccaat tcaaggtcaa    1020
```

```
aagagagaac ttttgtaaca tccacgtcag tctagttccc cagccaagtt caacagggga   1080
acagaagact aaacctaccc agaatagtgt tcgggaactt agaggacttg ggctttcccc   1140
agatctggtt gtatgcaggt gctcaaatcc acttgacaca tcagtgaagg agaaaatatc   1200
aatgttctgc catgttgagc ctgaacaagt gatctgtgtc cacgatgtct catccatcta   1260
ccgagtcccc ttgttgttag aggagcaagg ggttgtagat tatttcttc gaagacttga    1320 ccttcctatt gagaggcagc caagaaaaat gctgatgaaa tggaaagaga tggctgacag   1380
atatgatcgc ttgctggaga cctgctctat tgcccttgtg ggcaaataca cgaagttctc   1440
agactcctat gcctctgtca ttaaggctct ggagcattct gcactggcca tcaaccacaa   1500
attggaaatc aagtacatag attctgcgga cttggagccc atcacctcgc aagaagagcc   1560
cgtgcgctac cacgaagctt ggcagaagct ctgtagtgct catggagtgc tggttccagg   1620
aggatttggt gttcgaggaa cagaaggaaa atccaagca attgcctggg ctcggaatca    1680
gaaaaagcct ttttgggcg tgtgcttagg gatgcagttg gcagtggttg aattctcaag    1740
aaacgtgctg ggatggcaag atgccaattc tacagagttt gaccctacga ccagtcatcc   1800
cgtggtcgta gacatgccag aacacaaccc agggcagatg gcggaaccca tgaggctggg   1860
caagaggaga accctgttcc agaccaagaa ctcagtcatg aggaaactct atggagacgc   1920
agactacttg gaagagaggc accgccaccg atttgaggtg aatccagtct ggaaaaagtg   1980
tttggaagaa caaggcttga agtttgttgg ccaagatgtt gaaggagaga gaatggaaat   2040
tgtggagtta gaagatcatc ccttttttgt tggggttcag taccaccctg agttcctgtc   2100
caggcctatc aagccctccc caccatactt tggcctcctc ctggcctctg tggggcggct   2160
ctcacattac ctccagaaag gctgcaggct ctcacccagg gacacctata gtgacaggag   2220
tggaagcagc tcccctgact ctgaaatcac cgaactgaag tttccatcaa taaatcatga   2280
ctgatcttgt agcggatgat tcttcaagag acccttcaaa cttgggtaga gtttacagct   2340
ctgactttac actcggcttt ggagactttc tttaaattat gttttatta agattatttt     2400 attatgcgga aaggtatttg ggaaacttgt cacttgcatg tcccatcacg tgtactggct    2460
cctctgtggt gtctgcctgt tgcgtgacac tctccttgca gttcttgagt tgcggcagaa   2520
catcgcgatg ggaaccgatg gtgggtgggg ctgcagagtg ccccatcggt caccttgttt    2580
ctcaactacc tcgcatcatt gcagatgcta gcgcgttgcc tgtcgctttc ccttggatac   2640
ctagaccgtt ataaagtgtg ccacatggac ttaccgagca tggagagagg atttagcta   2700 ggatttgaac acttggtgct gggaacctca gggtattgct tgccactaag ccatgaaacc   2760
agagacaaaa tctctatact gccctgagtt gggggaatt ctcagtgcca actgtggctg    2820
gtcctcattc aaagggacgg tcagtttggt gtcaacatga acaccaaga tgtctgtctc    2880 tgaagcgtga ttttaaaatc cccatgcctg tggctgcgct tcctatttct agggctggga   2940
aacactcctt gcatcaaggg gtcacttaca gaacaaagaa tcttttgggg gaaacttcct   3000
ctaaaaccct ctcatatata gacagctttg actggagggt ccatttttct tccaggatgg   3060
tgttactgca gttgaaaggg caatatgaag ttactttctt aatgtgacct agcaataggc   3120
atagctacgt ggcactatat tctggccaga ctcgatgtgt actctaactt aagaaataaa   3180
tcagtaaggc agaacaagaa aaaaaaaaaa aaaaaaa                             3217

<210> SEQ ID NO 2
<211> LENGTH: 591
<212> TYPE: PRT
```

<213> ORGANISM: Homo sapiens

<400> SEQUENCE: 2

```
Met Lys Tyr Ile Leu Val Thr Gly Gly Val Ile Ser Gly Ile Gly Lys
1               5                   10                  15
Gly Ile Ile Ala Ser Ser Val Gly Thr Ile Leu Lys Ser Cys Gly Leu
            20                  25                  30
His Val Thr Ser Ile Lys Ile Asp Pro Tyr Ile Asn Ile Asp Ala Gly
        35                  40                  45
Thr Phe Ser Pro Tyr Glu His Gly Glu Val Phe Val Leu Asp Asp Gly
    50                  55                  60
Gly Glu Val Asp Leu Asp Leu Gly Asn Tyr Glu Arg Phe Leu Asp Ile
65                  70                  75                  80
Arg Leu Thr Lys Asp Asn Asn Leu Thr Thr Gly Lys Ile Tyr Gln Tyr
                85                  90                  95
Val Ile Asn Lys Glu Arg Lys Gly Asp Tyr Leu Gly Lys Thr Val Gln
            100                 105                 110
Val Val Pro His Ile Thr Asp Ala Ile Gln Glu Trp Val Met Arg Gln
        115                 120                 125
Ala Leu Ile Pro Val Asp Glu Asp Gly Leu Glu Pro Gln Val Cys Val
    130                 135                 140
Ile Glu Leu Gly Gly Thr Val Gly Asp Ile Glu Ser Met Pro Phe Ile
145                 150                 155                 160
Glu Ala Phe Arg Gln Phe Gln Phe Lys Val Lys Arg Glu Asn Phe Cys
                165                 170                 175
Asn Ile His Val Ser Leu Val Pro Gln Pro Ser Ser Thr Gly Glu Gln
            180                 185                 190
Lys Thr Lys Pro Thr Gln Asn Ser Val Arg Glu Leu Arg Gly Leu Gly
        195                 200                 205
Leu Ser Pro Asp Leu Val Val Cys Arg Cys Ser Asn Pro Leu Asp Thr
    210                 215                 220
Ser Val Lys Glu Lys Ile Ser Met Phe Cys His Val Glu Pro Glu Gln
225                 230                 235                 240
Val Ile Cys Val His Asp Val Ser Ser Ile Tyr Arg Val Pro Leu Leu
                245                 250                 255
Leu Glu Glu Gln Gly Val Val Asp Tyr Phe Leu Arg Arg Leu Asp Leu
            260                 265                 270
Pro Ile Glu Arg Gln Pro Arg Lys Met Leu Met Lys Trp Lys Glu Met
        275                 280                 285
Ala Asp Arg Tyr Asp Arg Leu Leu Glu Thr Cys Ser Ile Ala Leu Val
    290                 295                 300
Gly Lys Tyr Thr Lys Phe Ser Asp Ser Tyr Ala Ser Val Ile Lys Ala
305                 310                 315                 320
Leu Glu His Ser Ala Leu Ala Ile Asn His Lys Leu Glu Ile Lys Tyr
                325                 330                 335
Ile Asp Ser Ala Asp Leu Glu Pro Ile Thr Ser Gln Glu Glu Pro Val
            340                 345                 350
Arg Tyr His Glu Ala Trp Gln Lys Leu Cys Ser Ala His Gly Val Leu
        355                 360                 365
Val Pro Gly Gly Phe Gly Val Arg Gly Thr Glu Gly Lys Ile Gln Ala
    370                 375                 380
Ile Ala Trp Ala Arg Asn Gln Lys Lys Pro Phe Leu Gly Val Cys Leu
385                 390                 395                 400
```

```
Gly Met Gln Leu Ala Val Val Glu Phe Ser Arg Asn Val Leu Gly Trp
            405                 410                 415

Gln Asp Ala Asn Ser Thr Glu Phe Asp Pro Thr Thr Ser His Pro Val
            420                 425                 430

Val Val Asp Met Pro Glu His Asn Pro Gly Gln Met Gly Gly Thr Met
            435                 440                 445

Arg Leu Gly Lys Arg Arg Thr Leu Phe Gln Thr Lys Asn Ser Val Met
    450                 455                 460

Arg Lys Leu Tyr Gly Asp Ala Asp Tyr Leu Glu Arg His Arg His
465                 470                 475                 480

Arg Phe Glu Val Asn Pro Val Trp Lys Lys Cys Leu Glu Gln Gly
            485                 490                 495

Leu Lys Phe Val Gly Gln Asp Val Glu Gly Arg Met Glu Ile Val
            500                 505                 510

Glu Leu Glu Asp His Pro Phe Phe Val Gly Val Gln Tyr His Pro Glu
            515                 520                 525

Phe Leu Ser Arg Pro Ile Lys Pro Ser Pro Tyr Phe Gly Leu Leu
            530                 535                 540

Leu Ala Ser Val Gly Arg Leu Ser His Tyr Leu Gln Lys Gly Cys Arg
545                 550                 555                 560

Leu Ser Pro Arg Asp Thr Tyr Ser Asp Arg Ser Gly Ser Ser Ser Pro
                565                 570                 575

Asp Ser Glu Ile Thr Glu Leu Lys Phe Pro Ser Ile Asn His Asp
                580                 585                 590

<210> SEQ ID NO 3
<211> LENGTH: 16
<212> TYPE: PRT
<213> ORGANISM: Artificial Sequence
<220> FEATURE:
<223> OTHER INFORMATION: Synthetic Peptide - protein tranduction domain
      -16 amino acid sequence derived from the third helix of
      Antennapedia

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 86
<212> TYPE: PRT
<213> ORGANISM: Human immunodeficiency virus

<400> SEQUENCE: 4

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Ala His Gln Asn Ser Glu Thr
    50                  55                  60

His Gln Ala Ser Leu Ser Lys Gln Pro Thr Ser Gln Pro Arg Gly Asp
65                  70                  75                  80

Pro Thr Gly Pro Lys Glu
                85

<210> SEQ ID NO 5
```

```
<211> LENGTH: 11
<212> TYPE: PRT
<213> ORGANISM: Artificial Sequence
<220> FEATURE:
<223> OTHER INFORMATION: Synthetic Peptide - TAT protein transduction
      domain

<400> SEQUENCE: 5

Tyr Gly Arg Lys Lys Arg Arg Gln Arg Arg Arg
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide - protein transduction
      domain - basic domain of TAT

<400> SEQUENCE: 6

Arg Lys Lys Arg Arg Gln Arg Arg Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide - protein tranduction domain

<400> SEQUENCE: 7

Arg Arg Arg Arg Arg Arg Arg
1               5

<210> SEQ ID NO 8
<211> LENGTH: 12
<212> TYPE: PRT
<213> ORGANISM: Artificial Sequence
<220> FEATURE:
<223> OTHER INFORMATION: Synthetic Peptide - protein transduction domain

<400> SEQUENCE: 8

Arg Arg Gln Arg Arg Thr Ser Lys Leu Met Lys Arg
1               5                   10

<210> SEQ ID NO 9
<211> LENGTH: 27
<212> TYPE: PRT
<213> ORGANISM: Artificial Sequence
<220> FEATURE:
<223> OTHER INFORMATION: Synthetic Peptide - Transportan protein
      transduction domain

<400> SEQUENCE: 9

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 10
<211> LENGTH: 29
<212> TYPE: PRT
<213> ORGANISM: Artificial Sequence
<220> FEATURE:
<223> OTHER INFORMATION: Synthetic Peptide - KALA protein transduction
      domain

<400> SEQUENCE: 10
```

```
Trp Glu Ala Lys Leu Ala Lys Ala Leu Ala Lys Ala Leu Ala Lys His
1               5                   10                  15

Leu Ala Lys Ala Leu Ala Lys Ala Leu Lys Cys Glu Ala
            20                  25

<210> SEQ ID NO 11
<211> LENGTH: 16
<212> TYPE: PRT
<213> ORGANISM: Artificial Sequence
<220> FEATURE:
<223> OTHER INFORMATION: Synthetic Peptide - protein transduction domain

<400> SEQUENCE: 11

Arg Gln Ile Lys Ile Trp Phe Gln Asn Arg Arg Met Lys Trp Lys Lys
1               5                   10                  15

<210> SEQ ID NO 12
<211> LENGTH: 81
<212> TYPE: DNA
<213> ORGANISM: Artificial Sequence
<220> FEATURE:
<223> OTHER INFORMATION: Synthetic Polynucleotide - shRNA sequence in
      viral vector - shCTPS1 top strand

<400> SEQUENCE: 12
gtcgcgctag agcactctgc attggccatt aattcaagag attaatggcc aatgcagagt     60
gctctagcgc ttttttccaa a                                               81

<210> SEQ ID NO 13
<211> LENGTH: 84
<212> TYPE: DNA
<213> ORGANISM: Artificial Sequence
<220> FEATURE:
<223> OTHER INFORMATION: Synthetic Polynucleotide - shRNA sequence in
      viral vector - shCTPS1 bottom strand

<400> SEQUENCE: 13
agcttttgga aaaaagcgct agagcactct gcattggcca ttaatctctt gaattaatgg     60
ccaatgcaga gtgctctagc gcga                                            84

<210> SEQ ID NO 14
<211> LENGTH: 84
<212> TYPE: DNA
<213> ORGANISM: Artificial Sequence
<220> FEATURE:
<223> OTHER INFORMATION: Synthetic Polynucleotide - shRNA sequence in
      viral vector - shNME2 top strand

<400> SEQUENCE: 14
cgcgtcgaga tccatctgtg gtttaagccc gaagatcaa gagatcttcg ggcttaaacc      60
acagatggat ctctttttc caaa                                             84

<210> SEQ ID NO 15
<211> LENGTH: 84
<212> TYPE: DNA
<213> ORGANISM: Artificial Sequence
<220> FEATURE:
<223> OTHER INFORMATION: Synthetic Polynucleotide - shRNA sequence in
      viral vector - shNME2 bottom strand
```

```
<400> SEQUENCE: 15
agcttttgga aaaaagagat ccatctgtgg tttaagcccg aagatctctt gaatcttcgg        60
gcttaaacca cagatggatc tcga                                              84
```